(12) United States Patent
Lindsey

(10) Patent No.: US 8,187,824 B2
(45) Date of Patent: *May 29, 2012

(54) PORPHYRINIC COMPOUNDS FOR USE IN FLOW CYTOMETRY

(75) Inventor: Jonathan S. Lindsey, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/095,423

(22) PCT Filed: Nov. 30, 2006

(86) PCT No.: PCT/US2006/045927
§ 371 (c)(1),
(2), (4) Date: Sep. 19, 2008

(87) PCT Pub. No.: WO2007/064841
PCT Pub. Date: Jun. 7, 2007

(65) Prior Publication Data
US 2009/0075295 A1   Mar. 19, 2009

Related U.S. Application Data

(60) Provisional application No. 60/740,896, filed on Nov. 30, 2005.

(51) Int. Cl.
*C12Q 1/02* (2006.01)
*G01N 33/53* (2006.01)

(52) U.S. Cl. .......... 435/7.23; 435/7.1; 435/7.2; 435/34; 540/145

(58) Field of Classification Search ............ 540/145; 437/7.23; 435/6, 7.1, 7.2, 34, 7.23
See application file for complete search history.

(56) References Cited

U.S. PATENT DOCUMENTS

| | | | |
|---|---|---|---|
| 5,135,717 A * | 8/1992 | Renzoni et al. | 422/61 |
| 5,173,504 A * | 12/1992 | Dougherty | 514/410 |
| 5,492,924 A * | 2/1996 | Gatt et al. | 514/410 |
| 5,648,485 A * | 7/1997 | Dolphin et al. | 540/474 |
| 6,212,093 B1 | 4/2001 | Lindsey | |
| 6,272,038 B1 | 8/2001 | Clausen et al. | |
| 6,559,374 B2 | 5/2003 | Lindsey et al. | |
| 6,596,935 B2 | 7/2003 | Lindsey et al. | |
| 6,777,402 B2 | 8/2004 | Nifantiev et al. | |
| 6,794,505 B1 * | 9/2004 | Robinson et al. | 540/145 |
| 6,867,310 B1 | 3/2005 | Buchwald et al. | |
| 6,916,982 B2 | 7/2005 | Loewe et al. | |
| 2004/0044197 A1 | 3/2004 | Pandey et al. | |
| 2004/0110731 A1 | 6/2004 | Chan et al. | |
| 2004/0202612 A1 | 10/2004 | Adair | |
| 2005/0137180 A1 | 6/2005 | Robinson et al. | |
| 2005/0277770 A1 | 12/2005 | Balakumar et al. | |
| 2007/0108438 A1 | 5/2007 | Lindsey et al. | |

FOREIGN PATENT DOCUMENTS

WO  WO 2007047925 A2  4/2007
WO  WO 2007064842 A2  6/2007

OTHER PUBLICATIONS

Sutton et al, Bioconjugate Chem., 2002, 13, 249-63.*
Kim HJ. De novo synthesis of stable bacteriochlorins, North Carolina State University—Thesis, Ph.D. [online]. Mar. 2005 [retrieved on May 29, 2008], pp. 1-149 www.lib.ncsu.edu/theses/available/etd-03242005-180313/unrestricted/etd.pdf.
Borbas K E et al. Bioconjugatable porphyrins bearing a compact swallowtail motif for water solubility (2006), vol. 17, pp. 638-653.
Borbas K E et al. A compact water-soluble porphyrin bearing an iodoacetamido bioconjugatable site. Organic & Biomolecular Chemistry (2008), vol. 6, pp. 187-194.
International Search Report and Written Opinion, PCT/US06/45927, mailed Jul. 1, 2008.

* cited by examiner

*Primary Examiner* — Shaojia Anna Jiang
*Assistant Examiner* — Ganapathy Krishnan
(74) *Attorney, Agent, or Firm* — Myers Bigel Sibley & Sajovec, P.A.

(57) ABSTRACT

The present invention provides a method of detecting (e.g., by flow cytometry) a target compound, cell or particle, wherein the target is labelled with a detectable luminescent compound. The method comprises utilizing as the detectable luminescent compound a compound comprising a porphyrinic macrocycle such as a porphyrin, chlorin, bacteriochlorin, or isobacteriochlorin. In particular embodiments, the detectable luminescent compound comprises a compound of the formula A-A'-Z—B'—B, wherein: A is a targeting group or member of a specific binding pair that specifically binds the detectable luminescent compound to the target compound, cell or particle; A' is a linker group or covalent bond; B' is a linker group or covalent bond; B is a water-soluble group; and Z is the porphyrinic macrocycle.

8 Claims, 3 Drawing Sheets

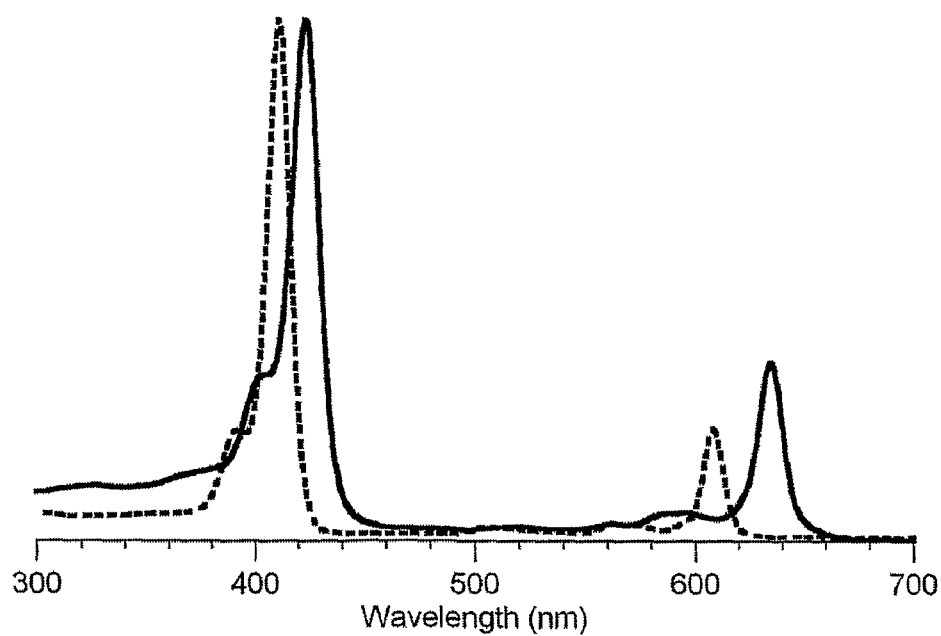
Figure 1. Absorption spectra of 13-acetylchlorin Zn-1 vs. the chlorin lacking the 13-acetyl group Zn-11 ($Q_y$ at 608 nm).
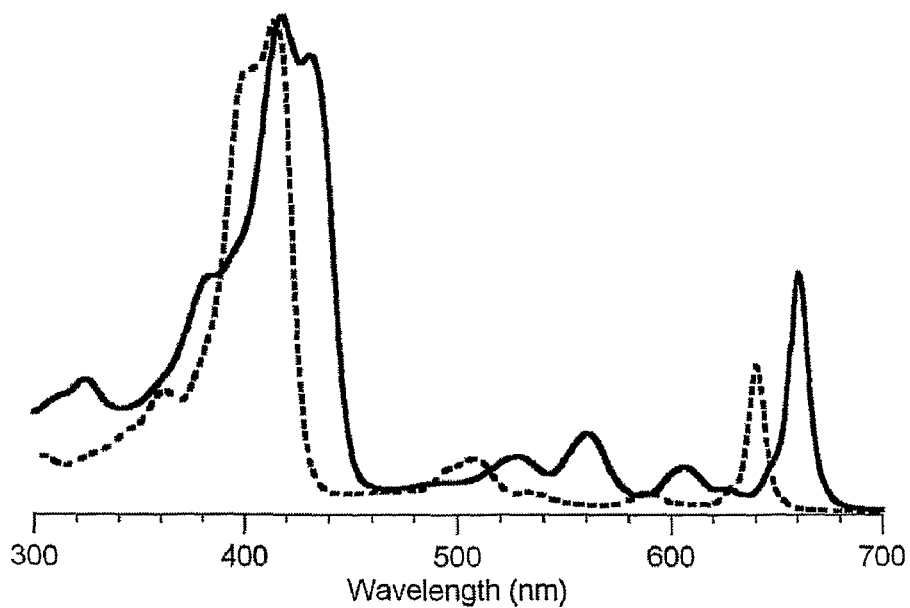
Figure 2. Absorption spectra of oxophorbine 2 vs. the chlorin lacking the $13^1$-oxo group 11.

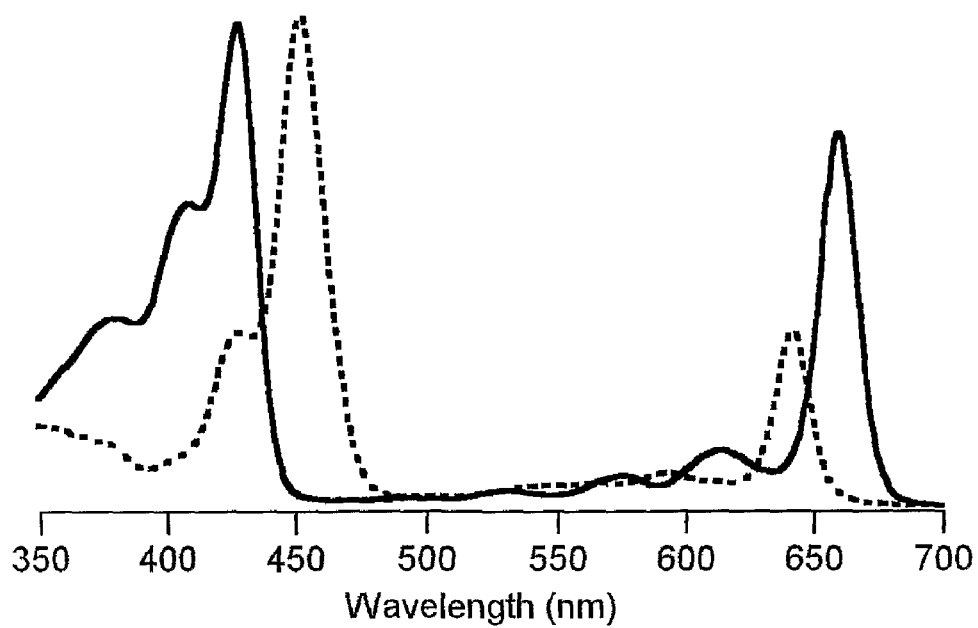
Figure 3. Absorption spectra of chlorophylls a and b.
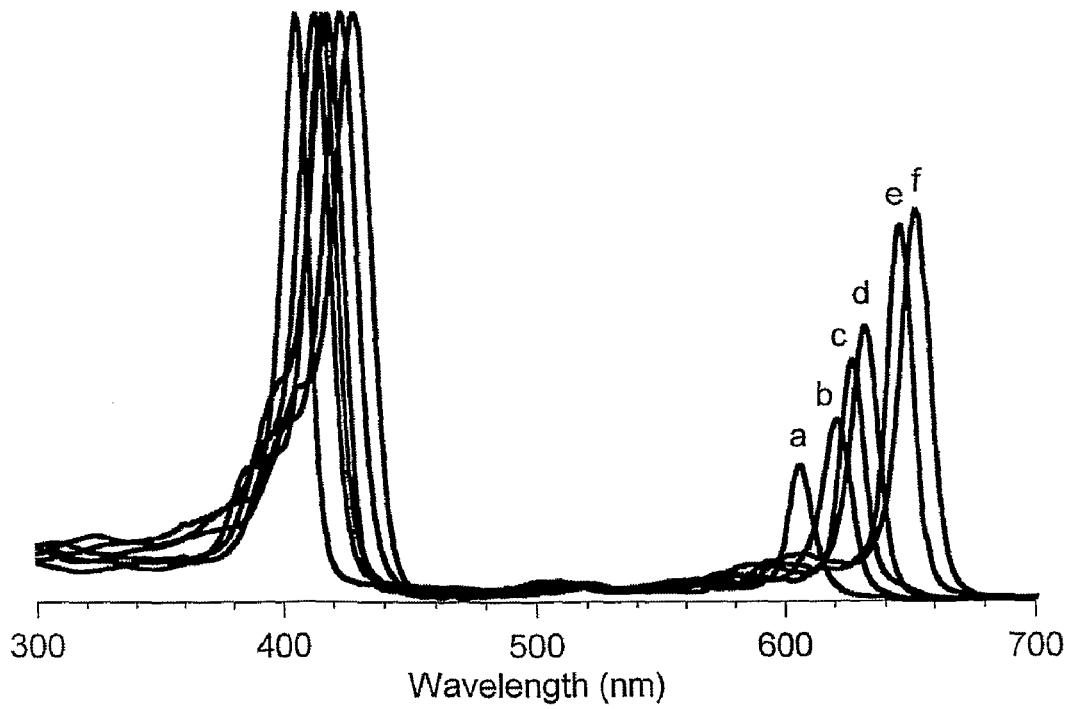
Figure 4. Absorption spectra in toluene at room temperature of a selection of zinc chlorins (10-mesityl family) bearing substituents at the 3- and/or 13-positions.

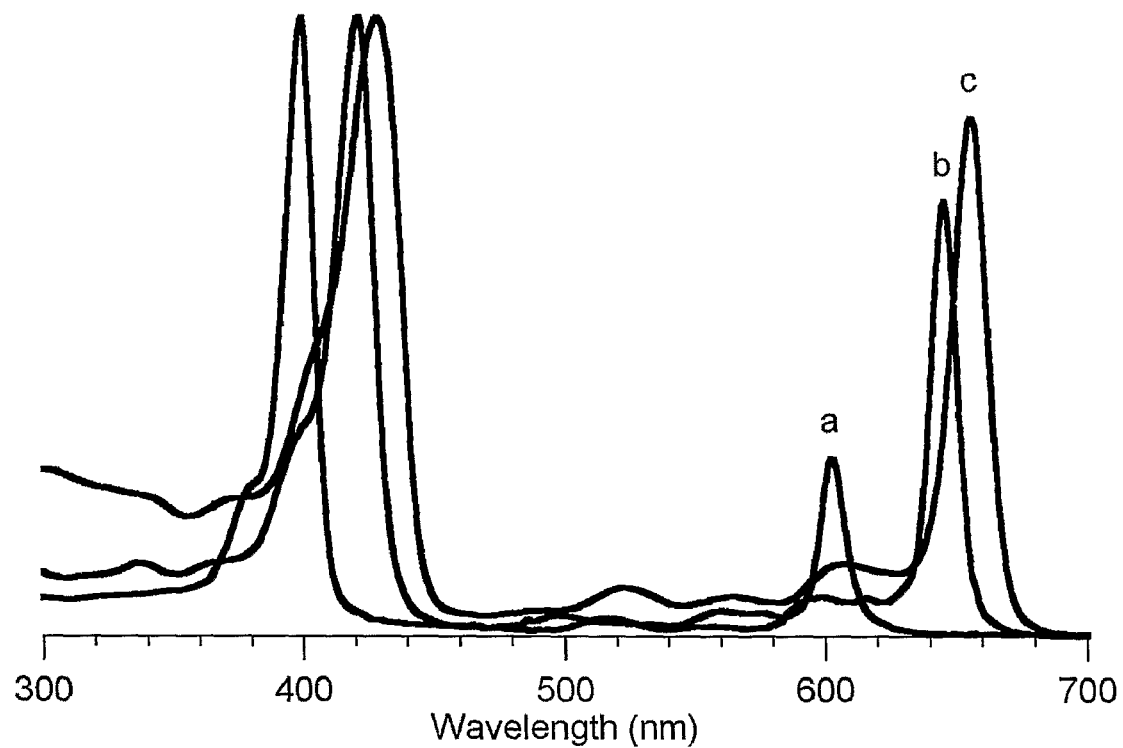
Figure 5. Absorption spectra in toluene at room temperature of zinc chlorins (10-unsubstituted family) bearing substituents at the 3,13-positions.

PORPHYRINIC COMPOUNDS FOR USE IN FLOW CYTOMETRY

RELATED APPLICATIONS

This application is a national phase application of PCT Application PCT/US2006/045927, filed Nov. 30, 2006, and published in English on Jun. 7, 2007, as International Publication No. WO 2007/064841, and which claims the benefit of United States Provisional Patent Application Ser. No. 60/740, 896, filed Nov. 30, 2005, the disclosure of each of which is incorporated by reference herein in its entirety.

This application is related to:

H. J. Kim and J. S. Lindsey, De Novo Synthesis of Bacteriochlorins, U.S. Provisional Patent Application No. 60/654, 270; Filed Feb. 18, 2005;

H.-J. Kim and J. S. Lindsey, De Novo Synthesis of Bacteriochlorins, U.S. Provisional Patent Application No. 60/720, 175, filed Sep. 23, 2005;

J. Lindsey, M. Taniguchi, A. Balaklumar, and D. Fan, Methods and Intermediates for the Synthesis of Porphyrins, U.S. patent application Ser. No. 11/193,562, filed Jul. 29, 2005;

K. E. Borbas and J. S. Lindsey, Swallowtail motifs for imparting water solubility to porphyrinic compounds, U.S. Provisional Patent Application Ser. No. 60/728,558, Filed Oct. 20, 2005; and Jonathan S. Lindsey, Joydev K. Laha, and Chinnasamy Muthiah, Synthesis of Chlorins and Phorbines with enhanced red spectral features, U.S. Provisional Patent Application Ser. No. 60/740,896, Filed Nov. 30, 2005.

GOVERNMENT FUNDING

This invention was made with Government support under Grant No. GM 36238 from the National Institutes of Health. The US Government has certain rights to this invention.

FIELD OF THE INVENTION

The present invention concerns flow cytometry and compounds useful as, among other things, detectable groups in flow cytometry.

BACKGROUND OF THE INVENTION

A large and growing number of applications require porphyrinic macrocycles that are water-soluble and are suited for conjugation in a variety of formats. The applications encompass flow cytometry, cellular and whole-organism imaging, sensing, photodynamic therapy, biomimetic catalysis, and radical scavenging. The success of these applications relies on a host of factors, including (1) significant solubility in aqueous saline solutions, thereby avoiding intermolecular aggregation (and excited-state quenching), (2) minimal non-specific binding to cellular components, (3) incorporation of a single reactive group for conjugation, thereby avoiding crosslinking and mixtures of products, and (4) robust synthesis affording ample quantities for experimentation.

SUMMARY OF THE INVENTION

A first aspect of the present invention is a method of detecting (e.g., by flow cytometry) a target compound, cell or particle, wherein the target is labelled with a detectable luminescent compound. The improvement comprises utilizing as the detectable luminescent compound a compound comprising a porphyrinic macrocycle.

In particular embodiments, the detectable luminescent compound comprises a compound of the formula A-A'-Z-B'—B, wherein: A is a targeting group or member of a specific binding pair that specifically binds said detectable luminescent compound to said target compound, cell or particle (that comprises, consists of or consists essentially of the corresponding member of the specific binding pair); A' is a linker group or covalent bond; B' is a linker group or covalent bond; B is a water-soluble group; and Z is the porphyrinic macrocycle.

In general, the detectable luminescent compound is excited by light at an excitation wavelength band and detected by emitted light at an emission wavelength band.

In some embodiments, the emission wavelength band has a full width at half maximum peak of not more than 30, 50, or 100 nanometers.

In general, in some embodiments, the excitation wavelength band has a peak between 350 and 900 nanometers; and the emission wavelength band has a peak between 550 and 1000 nanometers.

In some embodiments where the porphyrinic macrocycle is a porphyrin, the excitation wavelength band has a peak between 350 and 450 nanometers; and the emission wavelength band has a peak between 550 and 800 nanometers.

In some embodiments where the porphyrinic macrocycle is a bacteriochlorin, the excitation wavelength band has a peak between 350 and 450 nanometers and the emission wavelength band has a peak between 700 and 1000 nanometers.

In some embodiments where the porphyrinic macrocycle is a bacteriochlorin, the excitation wavelength band has a peak between 480 and 550 nanometers and the emission wavelength band has a peak between 700 and 1000 nanometers.

In some embodiments where the porphyrinic macrocycle is a bacteriochlorin, the excitation wavelength band has a peak between 720 and 740 nanometers, and the emission wavelength band has a peak between 725 and 780 nanometers.

In some embodiments where the porphyrinic macrocycle is a chlorin, the excitation wavelength band has a peak between 600 and 740 nanometers and the emission wavelength band has a peak between 610 and 800 nanometers.

In some embodiments where the porphyrinic macrocycle is a chlorin, the excitation wavelength band has a peak between 350 and 450 nanometers, and the emission wavelength band has a peak between 600 and 800 nanometers.

In some embodiments, where the detectable luminescent compound is excited by light at an excitation wavelength band and detected by emitted light at an emission wavelength band, the excitation wavelength band and the emission wavelength band each have peaks that are separated from one another by at least 50, 100 or 200 nanometers; and wherein the emission wavelength band has a full width at half maximum peak of not more than 50, 100, or 200 nanometers.

In some embodiments, where the detectable luminescent compound is excited by light at an excitation wavelength band and detected by emitted light at an emission wavelength band; the excitation wavelength band and the emission wavelength band each have peaks that are separated from one another by from 10 to 100 nanometers and wherein the emission wavelength band has a full width at half maximum peak of not more than 20, 25 or 30 nanometers.

The foregoing can be applied to the detection of single targets, or to the detection of multiple targets. For example, the present invention provides a method of detecting (e.g., by flow cytometry) and distinguishing (by different spectral and/ or lifetime characteristics) first and second target compounds, cells or particles, wherein the first target is labelled with a first detectable compound and the second target is labeled with a second detectable compound, the improvement comprising: utilizing a compound comprising a first porphyrinic macrocycle as the first detectable compound and a compound comprising a second porphyrinic macrocycle as the second detectable compound; wherein each of the first and second detectable compounds are excited at an excitation wavelength band; and wherein: (i) each of the first and second detectable compounds have a different emission wavelength band, the different emission wavelength bands characterized by peaks that are separated from one another by at least 5 or 10 nanometers; or (ii) the second compound has a lifetime at least 10, 20 or 30 percent greater than the first compound. As previously, the first and second detectable luminescent compounds, while differing from each other in structure and hence spectral properties (and/or lifetime) each comprise a compound of the formula A-A'-Z-B'—B, wherein: A is a targeting group that specifically binds the detectable compound to the target compound, cell or particle; A' is a linker group or covalent bond; B' is a linker group or covalent bond; B is a water-soluble group; and Z is the porphyrinic macrocycle. In general, both of the excitation wavelength bands have a peak between 350 and 900 nanometers; and both of the emission wavelength bands have a peak between 550 and 1000 nanometers.

In some embodiments, the different emission wavelength bands are characterized by peaks that are separated from one another by at least 50 or 100 nanometers.

In some embodiments, where the different emission wavelength bands are characterized by peaks that are separated from one another by 5 or 10 to 50 or 100 nanometers, each of the different emission wavelength bands have a full width at half maximum peak of not more than 10, 20, 30 or 50 nanometers.

In some preferred embodiments of the foregoing, the porphyrinic macrocycle (or macrocycles) is (or are) selected from the group consisting of porphyrins (including 17,18-didehydrophorbines), chlorins (including phorbines), bacteriochlorins (including bacteriophorbines), and isobacteriochlorins (including the isobacteriochlorins containing a fused "E" ring).

The foregoing and other objects and aspects of the invention are explained in greater detail in the specification set forth below.

BRIEF DESCRIPTION OF THE DRAWINGS

FIG. 1. Absorption spectra of 13-acetylchlorin Zn-1 ($Q_y$ at 632 nm) vs. the chlorin lacking the 13-acetyl group Zn-11 ($Q_y$ at 608 nm). The spectra were obtained in toluene at room temperature and are normalized at the B bands.

FIG. 2. Absorption spectra of oxophorbine 2 ($Q_y$ at 660 nm) vs. the chlorin lacking the $13^1$-oxo group 11 ($Q_y$ at 641 nm. The spectra were obtained in toluene at room temperature and are normalized at the B bands.

FIG. 3. Absorption spectra of chlorophylls a and b (in diethyl ether at room temperature). The $Q_y$ band in chlorophyll a or b appears at 662 or 644 nm, respectively.

FIG. 4. Absorption spectra in toluene at room temperature of a selection of zinc chlorins (10-mesityl family) bearing substituents at the 3- and/or 13-positions (normalized at the B bands). The chlorins (b-f) and their $Q_y$ bands include ZnC-$M^{10}$ (a) 606 nm; ZnC-$V^3M^{10}$ (b) 621 nm; ZnC-$E^3M^{10}$ (c) 627 nm; ZnC-$M^{10}A^{13}$ (d) 632 nm; ZnC-$E^3M^{10}E^{13}$ (e) 646 nm; and ZnC-$E^3M^{10}A^{13}$ (f) 652 nm. The B/$Q_y$ band intensity ratio decreases from 4.2 in ZnC-$M^{10}$ to 1.5 in ZnC-$E^3M^{10}A^{13}$.

FIG. 5. Absorption spectra in toluene at room temperature of zinc chlorins (10-unsubstituted family) bearing substituents at the 3,13-positions (normalized at the B bands). The chlorins (b, c) and their $Q_y$ bands include ZnC (a) 603 nm; ZnC-$E^3E^{13}$ (b) 645 nm; and ZnC-$E^3A^{13}$ (c) 655 nm. The B/$Q_y$ band intensity ratio decreases from 3.2 in ZnC to 1.2 in ZnC-$E^3A^{13}$.

DETAILED DESCRIPTION OF THE PREFERRED EMBODIMENTS

The disclosures of all United States Patent references cited herein are to be incorporated by reference herein as if fully set forth.

"Halo" as used herein refers to any suitable halogen, including —F, —Cl, —Br, and —I.

"Mercapto" as used herein refers to an —SH group.

"Azido" as used herein refers to an —$N_3$ group.

"Cyano" as used herein refers to a —CN group.

"Hydroxyl" as used herein refers to an —OH group.

"Nitro" as used herein refers to an —$NO_2$ group.

"Alkyl" as used herein alone or as part of another group, refers to a straight or branched chain hydrocarbon containing from 1 or 2 to 10, 20 or 50 carbon atoms (e.g., C1 to C4 alkyl; C4 to C10 alkyl; C11 to C50 alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Loweralkyl" as used herein, is a subset of alkyl, in some embodiments preferred, and refers to a straight or branched chain hydrocarbon group containing from 1 to 4 carbon atoms. Representative examples of loweralkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkylene" as used herein refers to a difunctional linear, branched or cyclic alkyl group, which may be substituted or unsubstituted, and where "alkyl" is as defined above.

"Alkenyl" as used herein alone or as part of another group, refers to a straight or branched chain hydrocarbon containing from 1 or 2 to 10, 20 or 50 carbon atoms (e.g., C1 to C4 alkenyl; C4 to C10 alkenyl; C11 to C50 alkenyl) (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadienyl, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkenylene" as used herein refers to a difunctional linear, branched or cyclic alkyl group, which may be substituted or unsubstituted, and where "alkenyl" is as defined above.

"Alkynyl" as used herein alone or as part of another group, refers to a straight or branched chain hydrocarbon containing from 1 or 20 to 10, 20 or 50 carbon atoms (e.g., C1 to C4 alkynyl; C4 to C10 alkynyl; C11 to C50 alkynyl) (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Alkynylene" as used herein refers to a difunctional linear, branched or cyclic alkynyl group, which may be substituted or unsubstituted, and where "alkynyl" is as defined above.

"Alkylidene chain" as used herein refers to a difunctional linear, branched, and/or cyclic organic group, which may be substituted or unsubstituted, which may be saturated or unsaturated, and which may optionally contain one, two or three heteroatoms selected from the group consisting of N, O, and S. Examples include but are not limited to alkylene, alkenylene, alkynylene, arylene, alkarylene, and aralkylene. See, e.g., U.S. Pat. No. 6,946,533. The alkylidene chain may contain any suitable number of carbon atoms (e.g., a C1 to C4; C4 to C10; C10 to C20; C20 to C50).

"Alkoxy" as used herein alone or as part of another group, refers to an alkyl or loweralkyl group, as defined herein, appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Acyl" as used herein alone or as part of another group refers to a —C(O)R radical, where R is any suitable substituent such as aryl, alkyl, alkenyl, alkynyl, cycloalkyl or other suitable substituent as described herein.

"Haloalkyl" as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Alkylthio" as used herein alone or as part of another group, refers to an alkyl group, as defined herein, appended to the parent molecular moiety through a thio moiety, as defined herein. Representative examples of alkylthio include, but are not limited to, methylthio, ethylthio, tert-butylthio, hexylthio, and the like.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino" as used herein means the radical —$NH_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —$NR_aR_b$, where $R_a$ and $R_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —$NR_aR_b$, where $R_a$ is an acyl group as defined herein and $R_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Formyl" as used herein refers to a —C(O)H group.

"Carboxylic acid" as used herein refers to a —C(O)OH group.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula S(O)(O)OH.

"Amide" as used herein alone or as part of another group refers to a —$C(O)NR_aR_b$ radical, where $R_a$ and $R_b$ are any suitable substituent such as H, alkyl, cycloalkyl, alkenyl, alkynyl or aryl.

"Sulfonamide" as used herein alone or as part of another group refers to a —$S(O)_2NR_aR_b$ radical, where $R_a$ and $R_b$ are any suitable substituent such as H, alkyl, cycloalkyl, alkenyl, alkynyl or aryl.

"Urea" as used herein alone or as part of another group refers to an —$N(R_c)C(O)NR_aR_b$ radical, where $R_a$, $R_b$ and $R_c$ are any suitable substituent such as H, alkyl, cycloalkyl, alkenyl, alkynyl or aryl.

"Alkoxyacylamino" as used herein alone or as part of another group refers to an —$N(R_a)C(O)OR_b$ radical, where $R_a$, $R_b$ are any suitable substituent such as H, alkyl, cycloalkyl, alkenyl, alkynyl or aryl.

"Aminoacyloxy" as used herein alone or as part of another group refers to an —$OC(O)NR_aR_b$ radical, where $R_a$ and $R_b$ are any suitable substituent such as H, alkyl, cycloalkyl, alkenyl, alkynyl or aryl.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3. Preferred heterocyclo groups include pyridyl and imidazolyl groups, these terms including the quaternized derivatives thereof, including but not limited to quaternary pyridyl and imidazolyl groups, examples of which include but are not limited to:

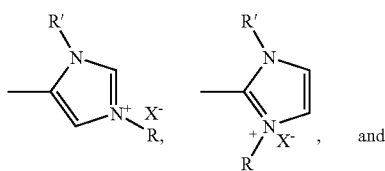

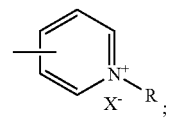

where R and R' are each a suitable substituent as described in connection with "alkyl" above, and particularly alkyl (such as methyl, ethyl or propyl), arylalkyl (such as benzyl), optionally substituted with hydroxy (—OH), phosphonic acid (—PO$_3$H$_2$) or sulfonic acid (—SO$_3$H), and X$^-$ is a counterion.

"Spiroalkyl" as used herein alone or as part of another group, refers to a straight or branched chain hydrocarbon, saturated or unsaturated, containing from 3 to 8 carbon atoms. Representative examples include, but are not limited to, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CHCHCH$_2$—, —CH$_2$CH$_2$CH$_2$CH$_2$CH$_2$CH$_2$—, etc. The term "spiroalkyl" is intended to include both substituted and unsubstituted "spiroalkyl" unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1 or 2.

"Aldehyde" as used herein refers to a group of the formula:

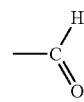

"Acetal" as used herein refers to a group of the formula:

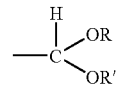

where R and R' are each suitable groups, e.g., groups independently selected from the group consisting of alkyl, aryl, alkylaryl, or where R and R' together form a group —R"— where R" is an alkylene (i.e., cycloalkyl). The acetal is preferably reasonably robust, and hence it is preferred that at least one, or more preferably both, of R and R' is not methyl, and it is particularly preferred that neither R nor R' is H.

"Bronsted acid" as used herein refers to a molecular entity (and corresponding chemical species) that is a proton donor to a base. Any suitable Bronsted acid may be used as a catalyst, with examples including but not limited to: trifluoroacetic acid, trichloroacetic acid, oxalic acid, taurine, malonic acid, formic acid, acetic acid, and NH$_4$Cl.

"Lewis acid" as used herein refers to a molecular entity (and corresponding chemical species) that is an electron-pair acceptor and therefore able to react with a Lewis base to form a Lewis adduct, by sharing the electron pair furnished by the Lewis base. Any suitable Lewis acid may be used as a catalyst, examples including compounds of the general formula $LnX_3$ where Ln is a lanthanide and X is halo such as Cl, Br, I, etc., triflate or OTf, etc., and with examples specific examples including but not limited to: $Yb(OTf)_3$, $IndCl_3$, $Sc(OTf)_3$, $MgBr_2$ and $CeCl_3$.

"Porphyrinic macrocycle" refers to a porphyrin or porphyrin derivative, and are discussed in greater detail below.

"Macrocyclic ligand" as used herein means a macrocyclic molecule of repeating units of carbon atoms and hetero atoms (e.g., O, S, or NH), separated by the carbon atoms (generally by at least two or three carbon atoms). Macrocyclic ligands exhibit a conformation with a so-called hole capable of trapping ions or molecules, particularly cations, by coordination with the electrons of the hetero atom (e.g., a lone pair of electrons on the oxygen atoms when the hetero atoms are oxygen). In general, the macrocyclic ring contains at least 9, 12 or 14 carbon atoms and hetero atoms (e.g., O, S, NH), each hetero atom in the ring being separated from adjoining hetero atoms in the ring by two or more carbon atoms. The macrocyclic ring may be substituted or unsubstituted, and may be fused to additional rings (e.g., 1 to 4 additional rings such as phenylene, naphthylene, phenanthrylene, and anthrylene rings). The macrocyclic ligand may be in the form of a substituent. See, e.g., U.S. Pat. No. 6,411,164 to Sibert.

"Crown ether" as used herein means a macrocyclic polyether whose structure exhibits a conformation with a so-called hole capable of trapping cations by coordination with a lone pair of electrons on the oxygen atoms (see generally McGraw-Hill Dictionary of Scientific and Technical Terms (3d ed. 1984)). Crown ethers are a species of macrocyclic ligand. The crown ether may be in the form of a substituent. See, e.g., U.S. Pat. No. 6,411,164 to Sibert.

"Polar group" as used herein refers to a group wherein the nuclei of the atoms covalently bound to each other to form the group do not share the electrons of the covalent bond(s) joining them equally; that is the electron cloud is denser about one atom than another. This results in one end of the covalent bond(s) being relatively negative and the other end relatively positive; i.e., there is a negative pole and a positive pole. Examples of polar groups include, without limitations, hydroxy, alkoxy, carboxy, nitro, cyano, amino (primary, secondary and tertiary), amido, ureido, sulfonamido, sulfinyl, sulfhydryl, silyl, S-sulfonamido, N-sulfonamido, C-carboxy, O-carboxy, C-amido, N-amido, sulfonyl, phosphono, morpholino, piperazinyl, tetrazolo, and the like. See, e.g., U.S. Pat. No. 6,878,733, as well as alcohol, thiol, polyethylene glycol, polyol (including sugar, aminosugar, uronic acid), sulfonamide, carboxamide, hydrazide, N-hydroxycarboxamide, urea, metal chelates (including macrocyclic ligand or crown ether metal chelates)

"Ionic group" as used herein includes anionic and cationic groups, and includes groups (sometimes referred to as "ionogenic" groups) that are uncharged in one form but can be easily converted to ionic groups (for example, by protonation or deprotonation in aqueous solution). Examples include but are not limited to carboxylate, sulfonate, phosphate, amine, N-oxide, and ammonium (including quaternized heterocyclic amines such as imidazolium and pyridinium as described above) groups. See, e.g., U.S. Pat. Nos. 6,478,863; 6,800,276; and 6,896,246. Additional examples include uronic acids, carboxylic acid, sulfonic acid, amine, and moieties such as guanidinium, phosphoric acid, phosphonic acid, phosphatidyl choline, phosphonium, borate, sulfate, etc. Note that compounds of the present invention can contain both an anionic group as one ionic substituent and a cationic group as another ionic substituent, with the compounds hence being zwitterionic. Note also that the compounds of the invention can contain more than one anionic or more than one cationic group.

"Protecting group" as used herein includes any suitable protecting group; "protected form" refers to a substituent in which an atom such as hydrogen has been removed and replaced with a corresponding protecting group. Protecting groups are known. See generally T. H. Greene and P. G. M. Wuts, *Protective Groups in Organic Synthesis,* 3rd edition, John Wiley & Sons, New York (1999). Examples include but are not limited to: hydroxy protecting groups (for producing the protected form of hydroxy); carboxy protecting groups (for producing the protected form of carboxylic acid); amino-protecting groups (for producing the protected form of amino); sulfhydryl protecting groups (for producing the protected form of sulfhydryl); etc. Particular examples include but are not limited to: benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, acetyl (Ac or $—C(O)CH_3$), benzoyl (Bn or $—C(O)C_6H_5$), and trimethylsilyl (TMS or $—Si(CH_3)_3$), and the like; formyl, acetyl, benzoyl, pivaloyl, t-butylacetyl, phenylsulfonyl, benzyl, t-butyloxycarbonyl (Boc), and benzyloxycarbonyl (Cbz) and the like; and hemithioacetals such as 1-ethoxyethyl and methoxymethyl, thioesters, or thiocarbonates and the like. See, e.g., U.S. Pat. Nos. 6,953,782; 6,951,946; 6,951,942; and 6,051,724.

"Treatment" as used herein means any manner in which one or more of the symptoms of a disease or disorder are ameliorated or otherwise beneficially altered. Treatment also encompasses any pharmaceutical use of the compositions herein, such as use for treating hyperproliferating tissue or neovascularization mediated diseases or disorders, or diseases or disorders in which hyperproliferating tissue or neovascularization is implicated. As used herein, amelioration of the symptoms of a particular disorder by administration of a particular compound or pharmaceutical composition refers to any lessening, whether permanent or temporary, lasting or transient that can be attributed to or associated with administration of the composition.

"Prodrug" as used herein is a compound that, upon in vivo administration, is metabolized by one or more steps or processes or otherwise converted to the biologically, pharmaceutically or therapeutically active form of the compound.

"Antibody" as used herein refers generally to immunoglobulins or fragments thereof that specifically bind to antigens to form immune complexes. The antibody may be whole immunoglobulin of any class, e.g., IgG, IgM, IgA, IgD, IgE, chimeric or hybrid antibodies with dual or multiple antigen or epitope specificities. It can be a polyclonal antibody, preferably an affinity-purified antibody from a human or an appropriate animal, e.g., a primate, goat, rabbit, mouse or the like.

Monoclonal antibodies are also suitable for use in the present invention, and are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility. Newer techniques for production of monoclonals can also be used, e.g., human monoclonals, interspecies monoclonals, chimeric (e.g., human/mouse) monoclonals, genetically engineered antibodies and the like.

"Irradiating" and "irradiation" as used herein includes exposing a subject to all wavelengths of light. Preferably, the irradiating wavelength is selected to match the wavelength(s) which excite the photosensitive compound. Preferably, the radiation wavelength matches the excitation wavelength of the photosensitive compound and has low absorption by the non-target tissues of the subject, including blood proteins.

"Biological materials" as used herein refers to both tissues (such as biopsy tissues) and cells, as well as biological fluids such as blood, urine, plasma, cerebrospinal fluid, mucus, sputum, etc.

Irradiation is further defined herein by its coherence (laser) or non-coherence (non-laser), as well as intensity, duration, and timing with respect to dosing using the photosensitizing compound. The intensity or fluence rate must be sufficient for the light to reach the target tissue. The duration or total fluence dose must be sufficient to photoactivate enough photosensitizing compound to act on the target tissue. Timing with respect to dosing with the photosensitizing compound is important, because 1) the administered photosensitizing compound requires some time to home in on target tissue and 2) the blood level of many photosensitizing compounds decreases with time. The radiation energy is provided by an energy source, such as a laser or cold cathode light source, that is external to the subject, or that is implanted in the subject, or that is introduced into a subject, such as by a catheter, optical fiber or by ingesting the light source in capsule or pill form (e.g., as disclosed in. U.S. Pat. No. 6,273,904 (2001)).

"Coupling agent" as used herein, refers to a reagent capable of coupling a photosensitizer to a targeting agent "Targeting agent" refers to a compound that homes in on or preferentially associates or binds to a particular tissue, receptor, infecting agent or other area of the body of the subject to be treated, such as a target tissue or target composition. Examples of a targeting agent include but are not limited to an antibody, a ligand, one member of a ligand-receptor binding pair, nucleic acids, proteins and peptides, and liposomal suspensions, including tissue-targeted liposomes.

"Specific binding pair" and "ligand-receptor binding pair" as used herein refers to two different molecules, where one of the molecules has an area on the surface or in a cavity which specifically attracts or binds to a particular spatial or polar organization of the other molecule, causing both molecules to have an affinity for each other. The members of the specific binding pair are referred to as ligand and receptor (antiligand). The terms ligand and receptor are intended to encompass the entire ligand or receptor or portions thereof sufficient for binding to occur between the ligand and the receptor. Examples of ligand-receptor binding pairs include, but are not limited to, hormones and hormone receptors, for example epidermal growth factor and epidermal growth factor receptor, tumor necrosis factor-.alpha. and tumor necrosis factor-receptor, and interferon and interferon receptor; avidin and biotin or antibiotin; antibody and antigen pairs; enzymes and substrates, drug and drug receptor; cell-surface antigen and lectin; two complementary nucleic acid strands; nucleic acid strands and complementary oligonucleotides; interleukin and interleukin receptor; and stimulating factors and their receptors, such as granulocyte-macrophage colony stimulating factor (GMCSD) and GMCSF receptor and macrophage colony stimulating factor (MCSF) and MCSF receptor.

"Linkers", or "linker groups" are aromatic or aliphatic groups (which may be substituted or unsubstituted and may optionally contain heteroatoms such as N, O, or S) that are utilized to couple a bioconjugatable group, cross-coupling group, surface attachment group, hydrophilic group or the like to the parent molecule. Examples include but are not limited to aryl, alkyl, heteroaryl, heteroalkyl (e.g., oligoethylene glycol), peptide, and polysaccharide linkers, etc.

"Water soluble group" as used herein generally includes substituents containing at least one ionic or polar group, coupled to the parent molecule directly or by means of an intervening linker. Examples include but are not limited to groups of the formula:

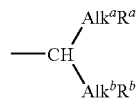

wherein $R_a$ and $R_b$ are each independently an ionic group or polar group, and $Alk^a$ and $Alk^b$ are each independently a C1-C50 alkylidene chain.

1. Active Compounds:

Active compounds of the present invention typically comprise a porphyrinic macrocycle, a water soluble group (e.g., an ionic or polar group) coupled, directly or indirectly, to the porphyrinic macrocycle, and a targeting group (e.g., a protein, peptide, nucleic acid, antibody, etc.) coupled, directly or indirectly, to the porphyrinic macrocycle.

Porphyrinic macrocycles are known. See, e.g., U.S. Pat. Nos. 6,946,552; 6,916,982; and 6,451,942. In general, "porphyrinic macrocycles" refers to a porphyrin or porphyrin derivative. Such derivatives include porphyrins with extra rings ortho-fused, or ortho-perifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral (meso-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g. phthalocyanines, porphyrazines, naphthalocyanines, subphthalocyanines, and porphyrin isomers). Preferred porphyrinic macrocycles comprise at least one 5-membered ring.

Water soluble groups and targeting groups can be directly or indirectly coupled to porphyrinic macrocyles in accordance with known techniques, or variations thereof which will be apparent to those skilled in the art given the disclosure herein. Illustrative examples are set forth in greater detail below.

An advantage of the active compounds of the present invention is that, as discussed in greater detail below, they can be readily "tuned" by the pattern of substituents thereon to alter the spectral properties thereof, and particularly the emission spectra. In some embodiments, active compounds that are substituted (or bear a substituent other than hydrogen) at one or more of the 3 and/or 13 (or where present the $13^1$ and/or $13^2$) positions, are preferred for carrying out the present invention.

A. Bacteriochlorins and Methods of Making.

As also noted in H. J. Kim and J. S. Lindsey, De Novo Synthesis of Bacteriochlorins, U.S. Provisional Patent Application No. 60/654,270; Filed Feb. 18, 2005 and H.-J. Kim and J. S. Lindsey, De Novo Synthesis of Bacteriochlorins, U.S. Provisional Patent Application No. 60/720,175, filed Sep. 23, 2005; an aspect of the present invention is a method of making a compound of Formula AI:

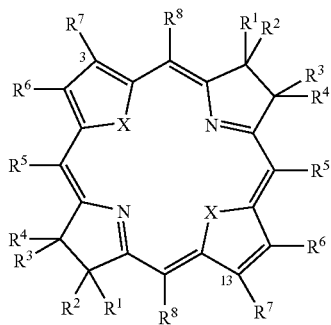

(AI)

wherein:

X is selected from the group consisting of Se, NH, $CH_2$, O and S;

$R^1$, $R^2$, $R^3$, $R^4$, $R^5$, $R^6$ $R^7$ and $R^8$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, linking groups, and surface attachment groups;

preferably subject to the proviso that neither $R^1$ nor $R^2$ is H; or neither $R^3$ nor $R^4$ is H;

or $R^1$ and $R^2$ together are =O (in which case preferably neither $R^3$ nor $R^4$ are H);

or $R^3$ and $R^4$ together form spiroalkyl, or in some embodiments $R^3$ and $R^4$ together are =O; and $R^8$ is H or as given above;

the method comprising self-condensing a compound (or condensing a pair of compounds) of Formula AII:

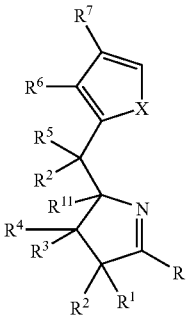

(AII)

in an organic solvent in the presence of an acid to produce the compound of Formula AI, wherein:

R is an acetal group;

X and $R^1$ to $R^7$ are as given above and $R^9$ is H; and $R^{11}$ and $R^{12}$ are each H; or $R^{11}$ and $R^{12}$ together form a covalent bond.

Optionally, $R^8$ is further substituted to replace H with additional substituents as described above in accordance with known techniques.

In some embodiments, $R^1$, $R^2$, $R^3$, and $R^4$ are preferably each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, alkoxy, carboxylic acid, hydroxyl, alkylthio, amino, alkylamino, arylalkylamino, disubstituted amino, acylamino, acyloxy, ester, In some embodiments, $R^1$, $R^2$, $R^3$, and $R^4$ are most preferably each independently selected from the group consisting of H and alkyl.

In some embodiments, preferably, $R^1$ and $R^2$ are each independently selected from the group consisting of H, alkyl, cycloalkyl, aryl, alkoxy, halo, mercapto, hydroxyl, nitro, acyl, alkoxy, alkylthio, amino, alkylamino, arylalkylamino, disubstituted amino, acylamino, acyloxy, amide, sulfonamide, urea, alkoxylacylamino, aminoacyloxy, and linking groups. Most preferably $R^1$ and $R^2$ are each independently selected from the group consisting of H, alkyl, aryl, alkoxy, halo, mercapto, cyano, hydroxyl, nitro, acyl, alkoxy, alkylthio, alkylamino, acyloxy, amide, and linking groups. In some embodiments $R^1$ and $R^2$ are preferably not H, alkyl or cycloalkyl ("cycloalkyl" including heterocyclo), particularly not alkyl or cycloalkyl, and most particularly one is not alkyl when the other is cycloalkyl.

In some embodiments, preferably, $R^3$ and $R^4$ are each independently selected from the group consisting of alkyl, alkenyl, alkynyl, cycloalkyl, cycloalkylalkyl, cycloalkylalkenyl, cycloalkylalkynyl, aryl, arylalkyl, arylalkenyl, arylalkynyl, and linking groups. Most preferably, $R^3$ and $R^4$ are each independently selected from the group consisting of alkyl, cycloalkyl, aryl, arylalkyl, and linking groups.

In some embodiments, preferably, $R^5$ is selected from the group consisting of H, alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, halo, cyano, nitro, acyl, alkoxy, alkylthio, amino, alkylamino, arylalkylamino, disubstituted amino, acylamino, acyloxy, amide, sulfonamide, urea, alkoxylacylamino, aminoacyloxy, and linking groups. Most preferably, $R^5$ is selected from the group consisting of H, alkyl, alkenyl, alkynyl, cycloalkyl, aryl, arylalkyl, arylalkenyl, arylalkynyl, alkoxy, halo, cyano, nitro, acyl, alkoxy, alkylthio, alkylamino, arylalkylamino, disubstituted amino, acylamino, acyloxy, amide, and linking groups.

In some embodiments $R^5$ is preferably not H or alkyl, and particularly not H.

In some embodiments, preferably, $R^6$ and $R^7$ are each independently selected from the group consisting of H, alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, halo, cyano, nitro, acyl, alkoxy, alkylthio, amino, alkylamino, arylalkylamino, disubstituted amino, acylamino, acyloxy, amide, sulfonamide, urea, alkoxylacylamino, aminoacyloxy, and linking groups. Most preferably, $R^6$ and $R^7$ are each independently selected from the group consisting of H, alkyl, alkenyl, alkynyl, cycloalkyl, aryl, arylalkyl, arylalkenyl, arylalkynyl, alkoxy, halo, cyano, nitro, acyl, alkoxy, alkylthio, alkylamino, arylalkylamino, disubstituted amino, acylamino, acyloxy, amide, and linking groups.

In some embodiments at least one or both $R^6$ is preferably neither H nor alkyl, and particularly not H.

In some embodiments at least one or both $R^7$ is preferably neither H nor alkyl, and particularly not methyl.

In some embodiments, preferably, $R^8$ is selected from the group consisting of H, alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, halo, cyano, nitro, acyl, alkoxy, alkylthio, amino, alkylamino, arylalkylamino, disubstituted amino, acylamino, acyloxy, amide, sulfonamide, urea, alkoxylacylamino, aminoacyloxy, and linking groups. Most preferably, $R^8$ is selected from the group consisting of H, alkyl, alkenyl, alkynyl, cycloalkyl, aryl, arylalkyl, arylalkenyl, arylalkynyl, alkoxy, halo, cyano, nitro, acyl, alkoxy, alkylthio, alkylamino, arylalkylamino, disubstituted amino, acylamino, acyloxy, amide, and linking groups.

In some embodiments $R^8$ is preferably not H or alkyl, and particularly not H.

In some embodiments compounds of Formula AI are subject to the proviso that, when X is NH: $R^1$ is not cycloalkyl; or $R^2$ is not methyl; or $R^5$ is not H; or $R^6$ is not H; or $R^7$ is not methyl.

Synthesis via acetal intermediates. Compounds of Formula AI are made from compounds of Formula AIIa or AIIb as shown below by treating the compounds of Formulas AIIa or AIIb with an acid in an organic solvent. The acid is not critical, with examples including but not limited to $BF_3$ etherate, $SnCl_4$, $InCl_3$, trifluoroacetic acid, and toluenesulfonic acid. The organic solvent is not critical with examples including but not limited to acetonitrile, methylene chloride, chloroform, tetrahydrofuran, chlorobenzene, ethanol, and combinations thereof. The reaction may be carried out at any suitable temperature, such as 0 to 100° C., and conveniently at room temperature, for any suitable time period, such as for a few minutes, 1 to 4 hours, or a day. The reaction mixture is preferably nonaqueous but need not be anhydrous, and may conveniently be carried out exposed to air. When compounds of Formula IIb are utilized the reaction mixture preferably includes an oxidizing agent such as air or DDQ.

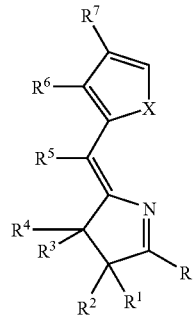

(AIIa)

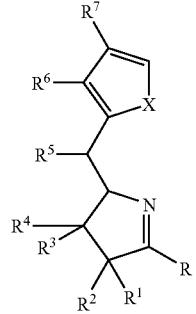

(AIIb)

in Formulas AIIa and AIIb, $R^1$ through $R^7$ are the same as given above in connection with Formula I, and R is acetal.

Compounds of Formulas AIIa and AIIb are made from compounds of Formula AIII:

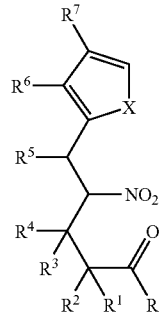

(AIII)

$R^1$ through $R^7$ are the same as given above in connection with Formula I, and R is acetal. In general, compounds of Formula IIa are produced by deprotonating a compound of Formula III (e.g., by treating with anhydrous sodium methoxide) to produce a nitronate anion intermediate, and then cyclizing the intermediate with a deoxygenating agent (e.g., by combining the intermediate with an aqueous buffered $TiCl_3$ solution) to produce the compound of Formula IIa. Reaction conditions are not critical and numerous variations will be apparent to those skilled in the art. In general, compounds of Formula IIb are produced by treating a compound of Formula III with a metal (e.g., zinc and acetic acid in ethanol) to produce an N-oxide intermediate, and then cyclizing the intermediate with a deoxygenating agent (eg., Ti(0), Zn, NaOH/methanol; Zn, aqueous $NH_4Cl$/THF; $FeSO_4$, aqueous $NH_4Cl$/$CH_3CN$; Mg or Fe, $AcONH_4$/methanol; $Ph_3P$/toluene; S/toluene; $NaN_3$/toluene; Zn, NaI, $Me_3SiCl$/$CH_3CN$; etc.) to produce the compound of Formula IIb. Again reaction conditions are not critical and numerous variations will be apparent to those skilled in the art.

Synthesis via aldehyde intermediates. Compounds of Formula AI are made from compounds of Formula AIIa or AIIb as shown above, where R is an aldehyde, by treating the compounds of Formulas AIIa or AIIb with an acid in an organic solvent in like manner as described above. Compounds of Formula AIIa or AIIb where R is an aldehyde are made by oxidizing a corresponding compound of Formula AV:

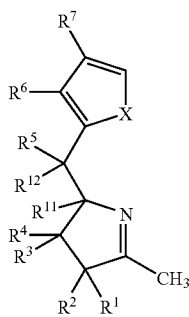

(AV)

in an organic solvent in the presence of an oxidizing agent to produce the compound of Formula AII. Any suitable solvent can be used, particularly ethereal solvents such as 1,4-dioxane, tetrahydrofuran, diethyl ether and dimethoxyethane. The reaction conditions are not critical and the reaction may be carried out at any suitable temperature, for example 0 to 100° C., preferably room temperature, for any suitable time, typically one to two hours. $SeO_2$ is currently preferred as the oxidizing agent, but any suitable oxidizing agent may be used. In general, when relatively powerful oxidizing agents are employed with alkyl groups that are activated by the presence of a π bond (allylic), the alkyl group can be oxidized to the aldehyde or ketone. The most common reagents for these transformations are selenium dioxide ($SeO_2$), chromium trioxide ($CrO_3$), chromyl chloride ($CrO_2Cl_2$), and $Pb(OAc)_4$. In addition, t-BuOOH/CuI oxidizes the allylic carbon of alkenyl conjugated ketones (Organic Synthesis, $2^{nd}$ Ed; Smith, M. B.; McGraw-Hill Higher Education: 2002; 272-279) and can also be used as oxidizing agents herein. A variety of chromium reagents have been used for allylic oxidations ((a) Dauben, W. G.; Lorber, M.; Fullerton, D. S. *J. Org. Chem.* 1969, 34, 3587-3592. (b) Fullerton, D. S.; Chen, C. M. *Synth. Commun.* 1976, 6, 217-220. (c) Salmond, W. G.; Barta, M. A.; Havens, J. L. *J. Org. Chem.* 1978, 43, 2057-2059. (d) Parish, E. J.; Chitrakorn, S.; Wei, T.-Y. *Synth. Commun.* 1986, 16, 1371-1375. (e) Parish, E. J.; Wei, T.-Y. *Synth. Commun.* 1987, 17, 1227-1233. (f) Marshall, C. W.; Ray, R. E.; Laos, I.; Riegel, B. *J. Am. Chem. Soc.* 1975, 79, 6308-6313. (g) Amann, A.; Ourisson, G.; Luu, B. *Synthesis* 1987, 1002-1005. (h) Bora, U.; Chaudhuri, M. K.; Dey, D.; Kalita, D.; Kharmawphlang, W.; Mandal, G. C. *Tetrahedron* 2001, 57, 2445-2448) and can also be used as oxidizing agents herein. Examples include $CrO_3$-pyridine complex, $CrO_3$ and 3,5-dimethylpyrazole, pyridinium chlorochromate (PCC), pyridinium dichromate (PDC), sodium chromate, sodium dichromate in acetic acid, pyridinium fluorochromate, and 3,5-dimethylpyrazolium fluorochromate (VI). The 5-methyl group of a pyrrole-2-ester was oxidized by ceric ammonium nitrate ((a) Huggins, M. T.; Lightner, D. A. *Tetrahedron* 2000, 56, 1797-1810. (b) Tipton, A. K.; Lightner, D. A.; McDonagh, A. F. *J. Org. Chem.* 2001, 66, 1832-1838) and this can also be used as an oxidizing agent herein.

Compounds of Formula AI may be produced wherein $R^8$ is H by the methods described above, and then $R^8$ brominated in accordance with known techniques and further substituents added at position $R^8$ in accordance with known techniques. Likewise other substituents can be added at positions $R^1$ through $R^7$ by substitution (e.g., by bromination or formylation) in accordance with known techniques.

B. "Swallowtail" Compounds and Methods of Making.

As also noted in K. E. Borbas and J. S. Lindsey, Swallowtail motifs for imparting water solubility to porphyrinic compounds, U.S. Provisional Patent Application Ser. No. 60/728,558, Filed Oct. 20, 2005, active compounds of the invention include compounds of Formula BI:

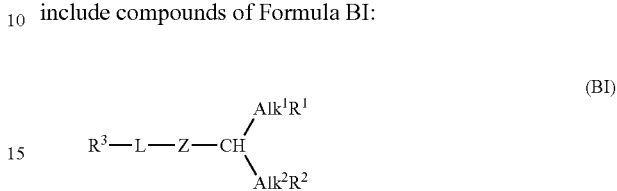

(BI)

wherein:

$Alk^1$ and $Alk^2$ are each independently a C1-C50 alkylidene chain;

Z is a porphyrinic macrocycle;

L is a linking group or is absent;

$R^1$ is an ionic group or polar group;

$R^1$ is an ionic group, polar group, bioconjugatable group, or targeting group;

$R^3$ is present or absent and when present is a halo group, bioconjugatable group, or targeting group, or a salt thereof.

Specific examples of the foregoing include, but are not limited to:

(a) porphyrins of Formula BIa:

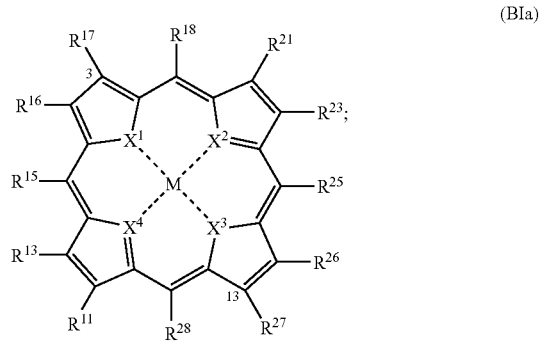

(BIa)

(b) chlorins of Formula BIb:

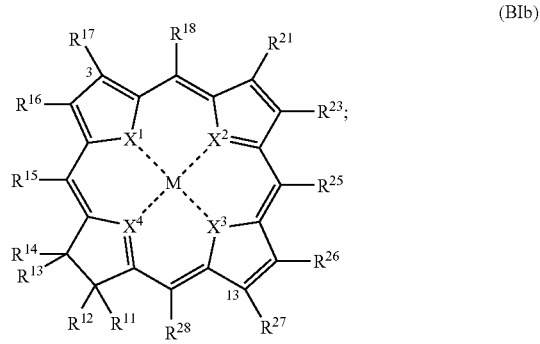

(BIb)

(c) bacteriochlorins of Formula BIc

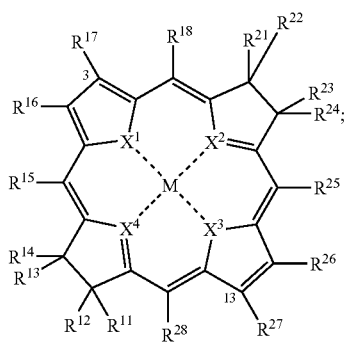

wherein:
M is a metal or is absent;
X is selected from the group consisting of Se, NH, $CH_2$, O and S;
$R^{11}$, $R^{12}$, $R^{13}$, $R^{14}$, $R^{15}$, $R^{16}$, $R^{17}$, $R^{18}$, $R^{21}$, $R^{22}$, $R^{23}$, $R^{24}$, $R^{25}$, $R^{26}$, $R^{27}$, and $R^{28}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, and groups of Formula BII:

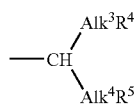

wherein $R^4$ and $R^5$ are each independently an ionic group or polar group, and $Alk^3$ and $Alk^4$ are each independently a C1-C50 alkylidene chain;
wherein each of $R^{11}$ and $R^{12}$, or $R^{21}$ and $R^{22}$, can together form =O;
and wherein each of $R^{13}$ and $R^{14}$, or $R^{23}$ and $R^{24}$, can together form spiroalkyl;
subject to the proviso that at least one of $R^{11}$, $R^{12}$, $R^{13}$, $R^{14}$, $R^{15}$, $R^{16}$, $R^{17}$, $R^{18}$, $R^{21}$, $R^{22}$, $R^{23}$, $R^{24}$, $R^{25}$, $R^{26}$, $R^{27}$, and $R^{28}$ is a bond to L and at least one thereof is a bond to said CH group of Formula BI;
and salts thereof.

In the case of bacteriochlorins of Formula BIc and V, $X^2$ and $X^4$ are preferably both N.

In the case of bacteriochlorins of Formula BIc, in some embodiments neither $R^{11}$ nor $R^{12}$ is H; in some embodiments neither $R^{13}$ nor $R^{14}$ is H; in some embodiments neither $R^{21}$ nor $R^{22}$ is H; in some embodiments neither $R^{23}$ nor $R^{24}$ is H; and in some embodiments all combinations thereof are not H.

In some embodiments of the foregoing, one of $R^{15}$, $R^{18}$, $R^{25}$ and $R^{28}$ is a bond to said CH group of Formula BI. In preferred embodiments such compounds are porphyrins of formula Ia or chlorins of formula BIb.

In some embodiments of the foregoing:
$R^{15}$ is a bond to L and $R^{25}$ is a bond to said CH group of Formula BI;
$R^{25}$ is a bond to L and $R^{15}$ is a bond to said CH group of Formula BI;
$R^{18}$ is a bond to L and $R^{28}$ is a bond to said CH group of Formula BI; or
$R^{28}$ is a bond to L and $R^{18}$ is a bond to said CH group of Formula BI.

In preferred embodiments such compounds are porphyrins of formula BIa or chlorins of formula BIb.

In some embodiments of the foregoing:
$R^{15}$ is a bond to L and $R^{18}$ is a bond to said CH group of Formula BI;
$R^{18}$ is a bond to L and $R^{25}$ is a bond to said CH group of Formula BI;
$R^{25}$ is a bond to L and $R^{28}$ is a bond to said CH group of Formula BI; or
$R^{28}$ is a bond to L and $R^{15}$ is a bond to said CH group of Formula BI.

In preferred embodiments such compounds are porphyrins of formula BIa or chlorins of formula BIb.

In some embodiments of the foregoing, one of $R^{11}$, $R^{12}$, $R^{13}$, $R^{14}$, $R^{16}$, $R^{17}$, $R^{21}$, $R^{22}$, $R^{23}$, $R^{24}$, $R^{26}$, or $R^{27}$ is a bond to said CH group of Formula BI. In preferred embodiments such compounds are bacteriochlorins of Formula BIc.

In some embodiments of the foregoing, one of $R^{11}$, $R^{12}$, $R^{13}$, $R^{14}$, $R^{16}$, or $R^{17}$ is a bond to L, and one of $R^{21}$, $R^{22}$, $R^{23}$, $R^{24}$, $R^{26}$, or $R^{27}$ is a bond to said CH group of Formula BI. In preferred embodiments such compounds are bacteriochlorins of formula BIc.

In some embodiments of the foregoing, one of $R^{16}$, $R^{17}$, $R^{26}$, or $R^{27}$ is a bond to said CH group of Formula BI. In preferred embodiments such compounds re bacteriochlorins of formula BIc.

In some embodiments of the foregoing:
$R^{16}$ is a bond to L and $R^{26}$ is a bond to said CH group of Formula BI;
$R^{26}$ is a bond to L and $R^{16}$ is a bond to said CH group of Formula BI;
$R^{17}$ is a bond to L and $R^{27}$ is a bond to said CH group of Formula BI; or
$R^{27}$ is a bond to L and $R^{17}$ is a bond to said CH group of Formula BI.

In preferred embodiments such compounds are bacteriochlorins of formula BIc.

Another aspect of the present invention is chlorins of Formula BVa and bacteriochlorins of Formula BVb:

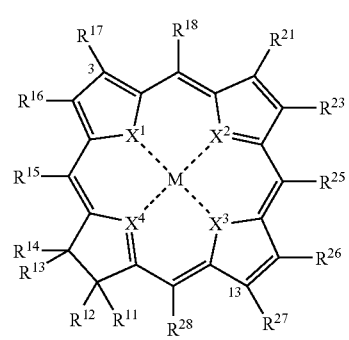

-continued

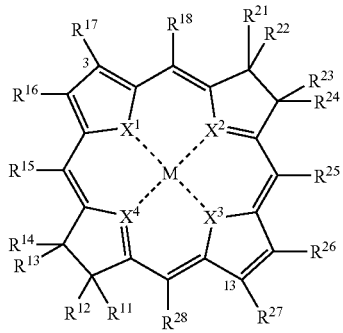

(BVb)

wherein:

M is a metal or is absent;

X is selected from the group consisting of Se, NH, $CH_2$, O and S;

$R^{13}$ is $Alk^1 R^1$ wherein $Alk^1$ is a C1-C50 alkylidene chain, and $R^1$ is an ionic group, polar group, bioconjugatable group, or targeting group;

$R^{14}$ is $Alk^2 R^2$ wherein $Alk^2$ is a C1-C50 alkylidene chain, and $R^2$ is an ionic group, polar group, bioconjugatable group, or targeting group;

$R^{11}$, $R^{12}$, $R^{15}$, $R^{16}$, $R^{17}$, $R^{18}$, $R^{21}$, $R^{22}$, $R^{23}$, $R^{24}$, $R^{25}$, $R^{26}$, $R^{27}$, and $R^{28}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxyacylamino, aminoacyloxy, linking groups, surface attachment groups, and groups of Formula II:

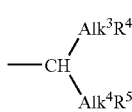

(II)

wherein $R^4$ and $R^5$ are each independently an ionic group or polar group, and $Alk^3$ and $Alk^4$ are each independently a C1-C50 alkylidene chain;

and wherein each of $R^{11}$ and $R^{12}$, or $R^{21}$ and $R^{22}$, can together form =O;

or $R^{23}$ and $R^{24}$ can together form spiroalkyl;

or $R^{23}$ is $Alk^{40} R^{41}$ wherein $Alk^{41}$ is an alkylidene chain, and $R^{41}$ is an ionic group, polar group, bioconjugatable group, or targeting group;

or $R^{24}$ is $Alk^{42} R^{42}$ wherein $Alk^{42}$ is an alkylidene chain, and $R^{42}$ is an ionic group, polar group, bioconjugatable group or targeting group;

or a salt thereof.

In some embodiments, when the compound is a bacteriochlorin of Formula Vb, $R^{23}$ and $R^{24}$ are preferably not both H.

In some embodiments, $R^1$ is an ionic group or polar group, and $R^2$ is a bioconjugatable group or targeting group.

In some embodiments, $R^1$ and $R^2$ are both independently selected ionic groups or polar groups, and one, or both, of $R^{41}$ and $R^{42}$ are independently selected bioconjugatable or targeting groups.

Compounds of Formulas BI (including BIa, BIb, and BIc) and Formula BV can be made by the methods described herein or variations thereof that will be apparent to persons skilled in the art based upon the present disclosure.

Porphyrins and Chlorins. Compounds of Formula BI, particularly porphyrins of Formula BIa and chlorins of Formula BIb, can be produced by reacting a dipyrromethane of Formula BIV with a suitable aldehyde, or dipyrromethane-dicarbinol, in accordance with known techniques.

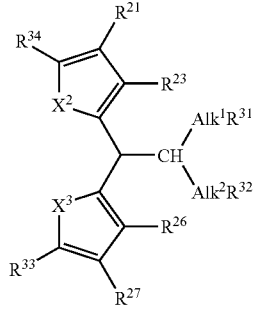

(BIV)

wherein:

$R^{31}$ and $R^{32}$ are each independently halo, —$XR^{35}$ where X is O, S, COO or NH and $R^{35}$ is H or a protecting group; or an ionic group, polar group, bioconjugatable group, or targeting group (in protected or unprotected form);

$R^{21}$, $R^{23}$, $R^{26}$, and $R^{27}$ are as given above; and $R^{33}$ and $R^{34}$ are H, aldehyde, or N,N-dialkylaminomethyl. Once the core ring is formed, the protecting groups (and optionally the oxygen covalently bonded thereto) can be removed and replaced with suitable polar, ionic, bioconjugatable or targeting groups in accordance with known techniques.

Compounds of Formula BIV are produced by reacting an aldehyde or acetal of Formula BIII

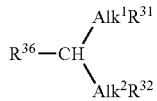

(BIII)

wherein $R^{31}$ and $R^{32}$ are as given above (e.g., in protected form) and $R^{36}$ is an aldehyde or acetal, with pyrrole (e.g., at least one pyrrole, each of which may be substituted or unsubstituted, and which together are preferably provided in excess) in a (preferably non-aqueous) reaction system (or "mixture") in the presence of a catalyst to form a dipyrromethane, quenching the reaction system by adding a base, separating the catalyst from the reaction system (e.g., by gravity or filtration) and then separating the pyrrole from the non-aqueous reaction system to produce a dipyrromethane of Formula IV as an intermediate. The one or more pyrroles may be unsubstituted or substituted 1, 2, 3 or 4 times with independently selected substituents of the same type as set forth in connection with $R^{21}$ and $R^{23}$, and $R^{26}$ and $R^{27}$, above. The reaction can be carried out in analogous manner to that described in J. Lindsey, S. Dhanalekshmi, J. Laha, and M. Taniguchi, Scalable Synthesis of Dipyrromethanes, US Patent Application No. 20050038262.

The amount of the compound of Formula BIII in the reaction system will vary depending upon the particular aldehyde or acetal used, but in general the molar ratio of the pyrrole to the compound of Formula BIII is 250:1 to 5,000:1. Stated differently, in general the amount of compound of Formula BIII is from 0.05 or 0.5 to 1 or 5 percent by weight of the system, or more, and the amount of pyrrole in the system is generally from 95 or 98 to 99 or 99.9 percent by weight of the system, or more. The catalyst may be a Bronsted acid or a Lewis acid, and the amount of catalyst in the system is, in general, from 0.01 or 0.1 to 0.5 or 1 percent by weight of the system, or more. Stated otherwise, the molar amount of acid is generally about 0.01 to 100 times the molar amount of aldehyde or acetal in the system. Preferably the system contains not more than 5 or 10 percent by weight water as noted above, and more preferably the system is non-aqueous. The next step of the method involves (b) reacting the compound of Formula BIII with the pyrrole in the reaction system to form the dipyrromethane therein. The reaction temperature is not critical, but in general may be from −20 or 0 to 100° C., or more, and is preferably room temperature. The pressure of the system during the reaction is not critical, but is conveniently ambient pressure. The reaction may be carried out for any suitable time, typically up to 24 hours, and preferably up to one hour. After the reaction step, the method involves (c) quenching the reaction system by adding a base thereto. The base is preferably added without simultaneously adding an organic solvent or water to the reaction system, and in a preferred embodiment the reaction system hence remains non-aqueous during quenching. In general, at least 1 equivalent of base per acid catalyst, up to 10 equivalents of base per acid catalyst, is added. The base may conveniently be added as a pure or neat substance (which may be a liquid or dry powder), a slurry in pyrrole, etc. The method then involves (d) separating the catalyst from the (preferably non-aqueous) reaction system, preferably by a filtration technique (such as suction filtration or pressure filtration) or a gravity technique (such as centrifugation or settling, e.g., with subsequent decanting); and then (e) separating the pyrrole from the (preferably non-aqueous) reaction system to produce the compound of Formula BIV a residual (e.g., by pumping off or evaporating the pyrrole).

Chlorins and Bacteriochlorins. Compounds of Formula BIc, BVa and BVb can be made by self-condensing a compound, condensing a pair of compounds, or condensing a compound of Formula BXII as a Western half with an appropriate Eastern half:

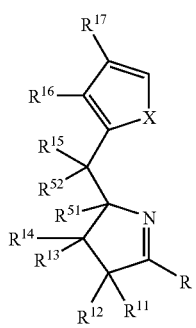

(BXII)

in an organic solvent in the presence of an acid to produce the compound of Formula BIc or BV, wherein:

R is an aldehyde or acetal group (for bacteriochlorins) or methyl (for chlorins);

X and $R^{11}$ to $R^{17}$ are as given above; and $R^{51}$ and $R^{52}$ are each H; or $R^{51}$ and $R^{52}$ together form a covalent bond.

Optionally, $R^{18}$ and $R^{28}$ in Formulas BIc and BVa, BVb (H by this synthesis) is further substituted to replace H with additional substituents as described above in accordance with known techniques.

Compounds of Formula BI are made from compounds of Formula BXII when R is acetal by treating the compounds with an acid in an organic solvent. The acid is not critical, with examples including but not limited to $BF_3$ etherate, $SnCl_4$, $InCl_3$, trifluoroacetic acid, and toluenesulfonic acid. The organic solvent is not critical with examples including but not limited to acetonitrile, methylene chloride, chloroform, tetrahydrofuran, chlorobenzene, ethanol, and combinations thereof. The reaction may be carried out at any suitable temperature, such as 0 to 100° C., and conveniently at room temperature, for any suitable time period, such as for a few minutes, 1 to 4 hours, or a day. The reaction mixture is preferably nonaqueous but need not be anhydrous, and may conveniently be carried out exposed to air. When $R^{51}$ and $R^{52}$ are both H the reaction mixture preferably includes an oxidizing agent such as air or DDQ.

Compounds of Formulas BXII are made from compounds of Formula BXIII:

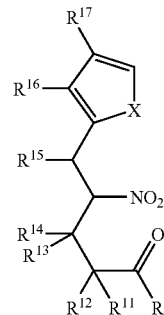

(BXIII)

$R^{11}$ through $R^{17}$ are the same as given above in connection with Formula BI, and R is acetal. In general, compounds of Formula BXII are produced by deprotonating a compound of Formula BXIII (e.g., by treating with anhydrous sodium methoxide) to produce a nitronate anion intermediate, and then cyclizing the intermediate with a deoxygenating agent (e.g., by combining the intermediate with an aqueous buffered $TiCl_3$ solution) to produce the compound of Formula BXII. Reaction conditions are not critical and numerous variations will be apparent to those skilled in the art. In general, compounds of Formula BXII are produced by treating a compound of Formula BXII with a metal (e.g., zinc and acetic acid in ethanol) to produce an N-oxide intermediate, and then cyclizing the intermediate with a deoxygenating agent (eg., Ti(0), Zn, NaOH/methanol; Zn, aqueous $NH_4Cl/$ THF; $FeSO_4$, aqueous $NH_4Cl/CH_3CN$; Mg or Fe, $AcONH_4/$ methanol; $Ph_3P$/toluene; S/toluene; $NaN_3$/toluene; Zn, NaI, $Me_3SiCl/CH_3CN$; etc.) to produce the compound of Formula BXII. Again reaction conditions are not critical and numerous variations will be apparent to those skilled in the art.

Compounds of Formula BIc or BVa, BVb are made from compounds of Formula BXII, where R is an aldehyde, by treating the compounds of Formula BXII with an acid in an organic solvent in like manner as described above. Compounds of Formula BXII where R is an aldehyde are made by oxidizing a corresponding compound of Formula BXV:

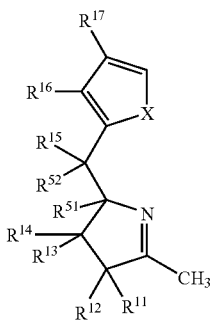

(BXV)

in an organic solvent in the presence of an oxidizing agent to produce the compound of Formula BXII. Any suitable solvent can be used, particularly ethereal solvents such as 1,4-dioxane, tetrahydrofuran, diethyl ether and dimethoxyethane. The reaction conditions are not critical and the reaction may be carried out at any suitable temperature, for example 0 to 100° C., preferably room temperature, for any suitable time, typically one to two hours. SeO$_2$ is currently preferred as the oxidizing agent, but any suitable oxidizing agent may be used. In general, when relatively powerful oxidizing agents are employed with alkyl groups that are activated by the presence of a π bond (allylic), the alkyl group can be oxidized to the aldehyde or ketone. The most common reagents for these transformations are selenium dioxide (SeO$_2$), chromium trioxide (CrO$_3$), chromyl chloride (CrO$_2$Cl$_2$), and Pb(OAc)$_4$. In addition, t-BuOOH/CuI oxidizes the allylic carbon of alkenyl conjugated ketones (Organic Synthesis, 2$^{nd}$ Ed; Smith, M. B.; McGraw-Hill Higher Education: 2002; 272-279) and can also be used as oxidizing agents herein. A variety of chromium reagents have been used for allylic oxidations ((a) Dauben, W. G.; Lorber, M.; Fullerton, D. S. J. Org. Chem. 1969, 34, 3587-3592. (b) Fullerton, D. S.; Chen, C. M. Synth. Commun. 1976, 6, 217-220. (c) Salmond, W. G.; Barta, M. A.; Havens, J. L. J. Org. Chem. 1978, 43, 2057-2059. (d) Parish, E. J.; Chitrakorn, S.; Wei, T.-Y. Synth. Commun. 1986, 16, 1371-1375. (e) Parish, E. J.; Wei, T.-Y. Synth. Commun. 1987, 17, 1227-1233. (f) Marshall, C. W.; Ray, R. E.; Laos, I.; Riegel, B. J. Am. Chem. Soc. 1975, 79, 6308-6313. (g) Amann, A.; Ourisson, G.; Luu, B. Synthesis 1987, 1002-1005. (h) Bora, U.; Chaudhuri, M. K.; Dey, D.; Kalita, D.; Kharmawphlang, W.; Mandal, G. C. Tetrahedron 2001, 57, 2445-2448) and can also be used as oxidizing agents herein. Examples include CrO$_3$-pyridine complex, CrO$_3$ and 3,5-dimethylpyrazole, pyridinium chlorochromate (PCC), pyridinium dichromate (PDC), sodium chromate, sodium dichromate in acetic acid, pyridinium fluorochromate, and 3,5-dimethylpyrazolium fluorochromate (VI). The 5-methyl group of a pyrrole-2-ester was oxidized by ceric ammonium nitrate ((a) Huggins, M. T.; Lightner, D. A. Tetrahedron 2000, 56, 1797-1810. (b) Tipton, A. K.; Lightner, D. A.; McDonagh, A. F. J. Org. Chem. 2001, 66, 1832-1838) and this can also be used as an oxidizing agent herein.

Compounds of Formula BIc and BVa, BVb may be produced wherein R$^{18}$ and R$^{28}$ are H by the methods described above, and then R$^8$ brominated in accordance with known techniques and further substituents added at position R$^{18}$ and R$^{28}$ in accordance with known techniques. Likewise other substituents can be added at positions R$^{11}$ through R$^{17}$ (or R$^{21}$ through R$^{27}$) by substitution (e.g., by bromination or formylation) in accordance with known techniques.

Chlorins and bacteriochlorins bearing polar/ionic-terminated dialkyl groups also can be prepared by reaction of compounds of Formula BXII where R$^{13}$ and R$^{14}$ constitute the polar/ionic terminated dimethyl groups. In this regard, it should be noted that substituents other than geminal dialkyl in the pyrroline ring have been introduced in chlorin chemistry (see the spiroalkyl-chlorins in Taniguchi, M., et al., J. Org. Chem. 2002, 67, 7329-7342). A similar route is suitable for introduction of polar/ionic-terminated groups at the R$^{13}$ and R$^{14}$ positions.

The synthesis of the requisite precursor of Formula BXII is shown in the synthetic scheme below. The starting compound 2-(2-nitroethyl)pyrrole undergoes Michael addition with an α,β-unsaturated ketone (BXVI), where R$^x$ and R$^y$ constitute the alkylidene chains terminated with polar or ionic or bioconjugatable or targeting groups, which may be in protected form. Compounds of formula BXVI are available by Witting condensation of dimethyl (2-oxopropyl)phosphonate and the ketone R$^x$C(O)R$^y$. The product of the Michael addition is the nitro-hexanone pyrrole (BXIII). For the preparation of chlorins via a tetrahydrodipyrrin, compound BXIII undergoes reductive cyclization to give the N-oxide (BXV-oxide), which upon deoxygenation affords the desired 1-methyl-2,3,4,5-tetrahydrodipyrrin BXV. Compound XV serves as the Western half in chlorin syntheses. For the preparation of chlorins via a dihydrodipyrrin, compound BXIII undergoes reductive cyclization to give desired 1-methyl-2,3-dihydrodipyrrin compound BXV. Compound BXV serves as the Western half in chlorin syntheses.

For the preparation of bacteriochlorins via a dihydrodipyrrin, compound BXIII undergoes reductive cyclization to give compound XV; where R=acetal, BXV undergoes self-condensation to afford the corresponding bacteriochlorin. Alternatively, where R=methyl, BXV can be treated to conditions for oxidation of the terminal methyl group, affording dihydrodipyrrin-aldehyde BXII. Compound BXII also undergoes self-condensation to give the corresponding bacteriochlorin.

Examples of the foregoing may be carried out as shown in the Scheme below:

Synthetic Scheme

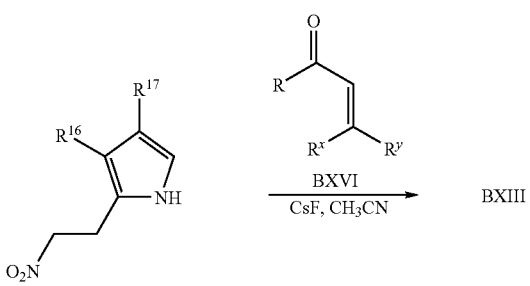

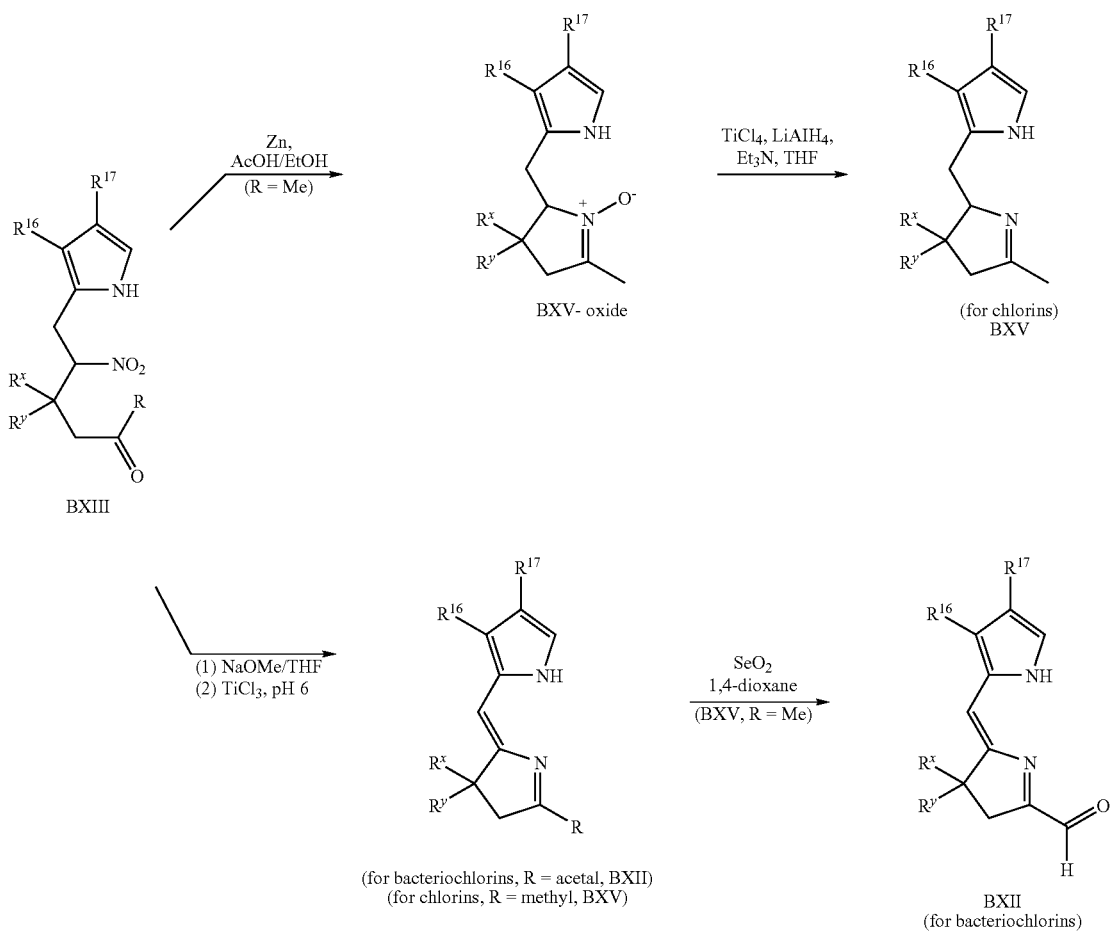

A dipyrromethane of Formula BIV can be converted to an Eastern half for use in chlorin synthesis. The conversion entails 1-acylation followed by 9-bromination. The acylation is best achieved by treatment of the Eastern half with a Grignard reagent (EtMgBr or mesityl-MgBr) followed by a 2-pyridyl thioate (Mukaiyama reagent) as described by Rao, P. D. et al., *J. Org. Chem.* 2000, 65, 1084-1092. Such 1-acyldipyrromethanes can be isolated through the use of a dialkylboron complexation method (Muthukumaran, K. et al., *J. Org. Chem.* 2004, 69, 5354-5364.). The bromination is best achieved with N-bromosuccinimide at −78° C. as described by Taniguchi, M. et al., *J. Org. Chem.* 2001, 66, 7342-7354. The conditions for converting dipyrromethane of Formula IV to an Eastern half are rather mild, and consequently, are tolerant to a broad range of substituents in the swallowtail motif.

C. Trans Porphyrins and Related Compounds.

As also noted in J. Lindsey, M. Taniguchi, A. Balakumar, and D. Fan, Methods and Intermediates for the Synthesis of Porphyrins, U.S. patent application Ser. No. 11/193,562, the present invention provides porphyrins, and a method of making porphyrins, of Formula CI:

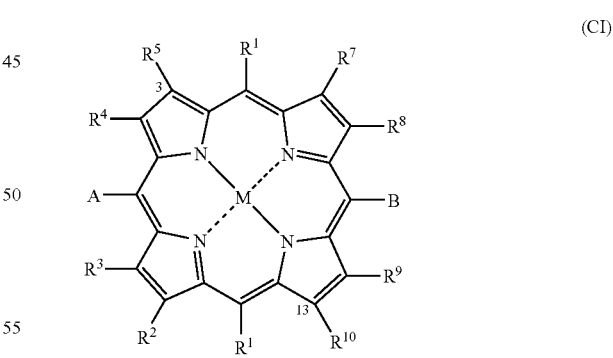

(CI)

wherein:

A and B are each independently selected from the group consisting of H, alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, halo, mercapto, azido, cyano, hydroxyl, nitro, acyl, alkoxy, alkylthio, amino, alkylamino, arylalkylamino, disubstituted amino, acylamino, acyloxy, amide, sulfonamide, urea, alkoxylacylamino, aminoacyloxy, hydrophilic groups, surface attachment groups, cross-coupling groups and bioconjugatable groups (with A preferably aryl, including aromatic hydrophilic groups, aromatic surface attachment groups, aromatic cross-coupling groups, and aromatic bioconjugatable groups);

R$^1$ is selected from the group consisting of H, alkyl and aryl (preferably H);

R$^2$, R$^3$, R$^4$, R$^5$, R$^7$, R$^8$, R$^9$, and R$^{10}$ are each independently selected from the group consisting of H, halo, loweralkoxy, and loweralkylthio; and M is a metal or a pair of hydrogen atoms; said method comprising:

(a) condensing (i) a bis(imino)dipyrromethane of Formula CII:

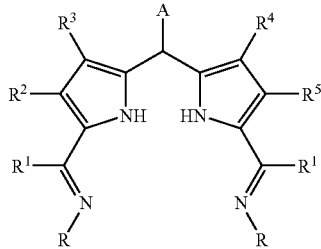

(CII)

wherein:
R is alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, or acyl; and
A, R$^1$, R$^2$, R$^3$, R$^4$, and R$^5$ are as given above, with (ii) a dipyrromethane of Formula CIII:

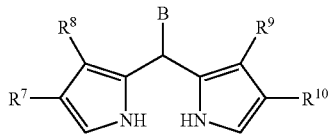

(CIII)

wherein B, R$^7$, R$^8$, R$^9$ and R$^{10}$ are as given above, in a polar or nonpolar, protic or aprotic organic solvent containing a metal salt to produce a reaction product; then (b) optionally oxidizing said reaction product with an oxidizing agent; and then (c) optionally demetallating said reaction product to produce the porphyrin of Formula CI. The reaction conditions are not critical and any suitable solvent can be used, including but not limited to methanol, ethanol, propanol, isopropanol, chloroform, tetrahydrofuran, dichloromethane, toluene, and mixtures thereof. The reaction can be carried out at any convenient temperature such as between 0 and 100° C. Any suitable metal salt can be used, including but not limited to zinc, palladium, copper, nickel and cobalt salts (which then provides the metal M for the compound of Formula CI). For some substituents no external oxidizing agent is required and oxidation is achieved by oxygen in ambient air. When an oxidizing agent is required any suitable oxidizing agent can be used, such as oxygen or a quinone oxidizing agent such as dichlorodicyanobenzoquinone (DDQ), p-chloranil, and o-chloranil. The demetallating step can be carried out in accordance with known techniques by treating or mixing the metallated compound with any suitable acid (e.g., acetic acid, trifluoroacetic acid, hydrochloric acid, sulfuric acid, etc.).

In some embodiments A is preferably an aromatic, or aryl, group, including aromatic hydrophilic groups, aromatic surface attachment groups, aromatic cross-coupling groups, or aromatic bioconjugatable group (for example, an aryl-containing linker group substituted one or more times with an alkene, alkyne, alcohol, thiol, selenyl, phosphono, carboxylic acid, formyl, halo or amine group).

In some embodiments, B is preferably a hydrophilic group, surface attachment group, cross-coupling group, or bioconjugatable group (e.g., an alkene, alkyne, alcohol, thiol, selenyl, phosphono, carboxylic acid, formyl, halo or amine group, coupled directly to the parent molecule or by means of an intervening linker group).

In some embodiments, A is a bioconjugatable group or targeting group and B is a hydrophilic or water soluble group as given above; or A is a hydrophilic group or water soluble group and B is a bioconjugatable group or water soluble group as given above.

The present invention also provides a method of making a compound of Formula CII:

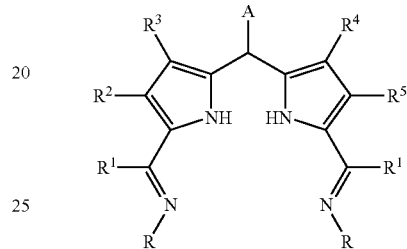

(CII)

wherein:
R, is alkyl, alkenyl, alkynyl, cycloalkyl, cycloalkylalkyl, cycloalkylalkenyl, cycloalkylalkynyl, aryl, arylalkyl, arylalkenyl, arylalkynyl, alkoxy, or acyl;

R$^1$ is H, alkyl or aryl, preferably H;

R$^2$, R$^3$, R$^4$, and R$^5$ are each independently selected from the group consisting of H, halo, loweralkoxy, and loweralkylthio; and A is as given above, preferably aryl.

The method comprises reacting a dipyrromethane of Formula CIV:

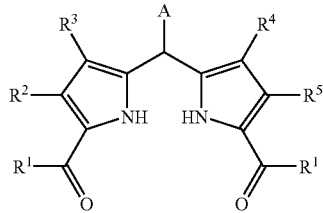

(CIV)

wherein A, R$^1$, R$^2$, R$^3$, R$^4$ and R$^5$ are as given above, with a compound of Formula CV:

R—NH$_2$ (CV)

wherein R is as given above in an organic solvent to produce said compound of Formula CII. The reaction conditions are not critical and can be carried out in any suitable organic solvent (such as described above), neat if desired, at any convenient temperature such as 0 to 100° C. The compound of Formula V is preferably included in a stoichiometric amount, preferably in excess, for example five, ten or twenty times excess. Suitable solvents include but are not limited to methylene chloride, chloroform, tetrahydrofuran, nitromethane, toluene, acetonitrile, methanol, ethanol, and mixtures thereof.

Compounds of Formula CIV and Formula CV can be made in accordance with known techniques for the synthesis of dipyrromethanes and amines, or variations thereof that will be apparent to persons skilled in the art.

D. Phorbines and Related Compounds.

Particular embodiments of porphyrins, chlorins, bacteriochlorins, and isobacteriochlorin porphyrinic macrocycle compounds useful for carrying out the present invention include compounds of general Formula DI and DI':

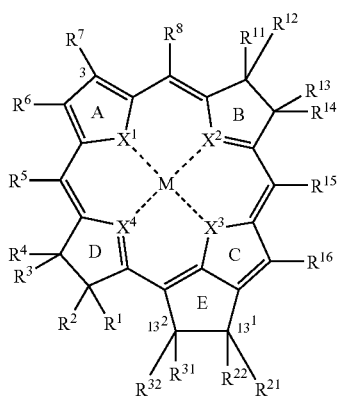

(DI)

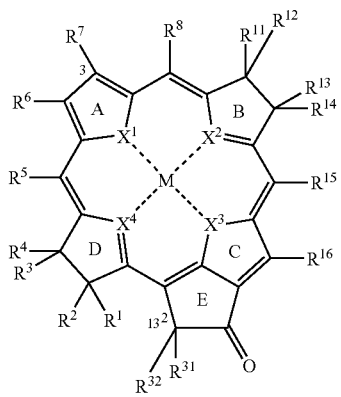

(DI')

with particular embodiments of the foregoing including: (a) 17,18-didehydrophorbines (a particular embodiment of a porphyrin) of Formula DIa and DIa':

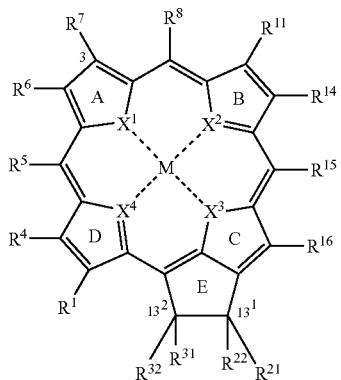

(DIa)

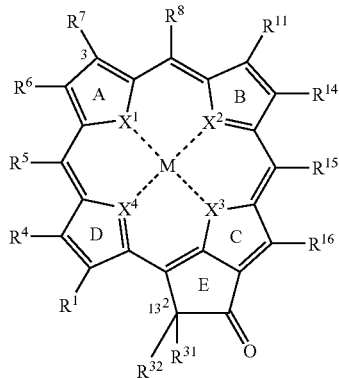

(DIa')

(b) phorbines (a particular embodiment of a chlorin) of Formula DIb and DIb':

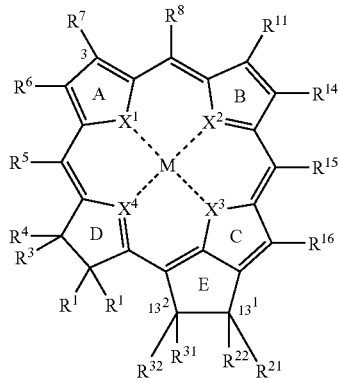

(DIb)

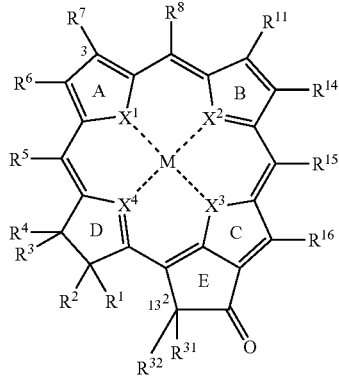

(DIb')

(c) bacteriophorbines (a particular embodiment of a bacteriochlorin) of Formula DIc and DIc':

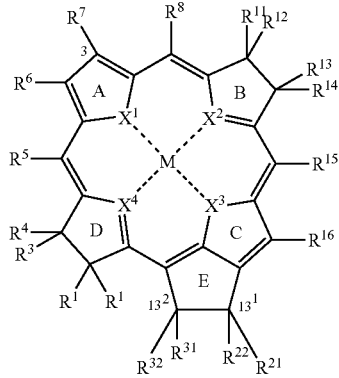

(DIc)

-continued

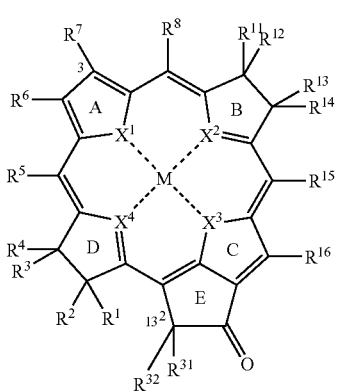

(DIc')

and (d) opp-chlorins (a particular embodiment of a chlorin), or opp-phorbines (a particular embodiment of a phorbine), of Formula DId and DId':

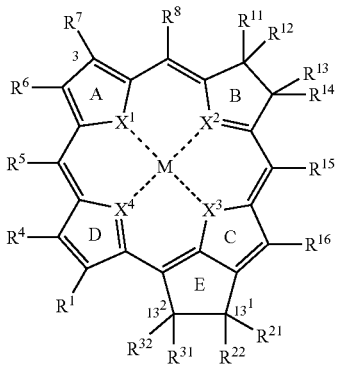

(DId)

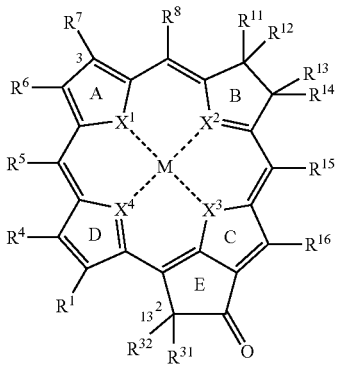

(DId')

wherein:
M is a metal or is absent;
$X^1$, $X^2$, $X^3$ and $X^4$ are each independently selected from the group consisting of Se, NH, $CH_2$, O and S;
$R^1$, $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, $R^{21}$, $R^{22}$, $R^{31}$ and $R^{32}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, linking groups, surface attachment groups, bioconjugatable groups, targeting groups, and water soluble groups;
wherein each pair of $R^1$ and $R^2$, $R^{11}$ and $R^{12}$, $R^{21}$ and $R^{22}$, or $R^{31}$ and $R^{32}$, can together form =O;
wherein each of $R^1$ and $R^2$, $R^3$ and $R^4$, $R^{11}$ and $R^{12}$, or $R^{13}$ and $R^{14}$, can together form spiroalkyl;
wherein $R^2$ and $R^3$ can together form a double bond; and
wherein $R^{12}$ and $R^{13}$ can together form a double bond;
or a salt thereof.

Some embodiments are subject to the proviso that: (i) neither $R^1$ nor $R^2$ is H; or neither $R^3$ nor $R^4$ is H; or neither $R^{11}$ nor $R^{12}$ is H; or neither $R^{13}$ nor $R^{14}$ is H.

In some embodiments, $R^1$ and $R^2$ are both independently selected from the group consisting of alkyl, alkenyl, alkynyl, cycloalkyl, cycloalkylalkyl, cycloalkylalkenyl, cycloalkylalkynyl, aryl, arylalkyl, arylalkenyl, arylalkynyl, and linking groups; or
$R^3$ and $R^4$ are both independently selected from the group consisting of alkyl, alkenyl, alkynyl, cycloalkyl, cycloalkylalkyl, cycloalkylalkenyl, cycloalkylalkynyl, aryl, arylalkyl, arylalkenyl, arylalkynyl, and linking groups; or
$R^{11}$ and $R^{12}$ are both independently selected from the group consisting of alkyl, alkenyl, alkynyl, cycloalkyl, cycloalkylalkyl, cycloalkylalkenyl, cycloalkylalkynyl, aryl, arylalkyl, arylalkenyl, arylalkynyl, and linking groups; or
$R^{13}$ and $R^{14}$ are both independently selected from the group consisting of alkyl, alkenyl, alkynyl, cycloalkyl, cycloalkylalkyl, cycloalkylalkenyl, cycloalkylalkynyl, aryl, arylalkyl, arylalkenyl, arylalkynyl, and linking groups.

In some embodiments, $R^1$ and $R^2$ are both independently selected from the group consisting of alkyl, cycloalkyl, aryl, arylalkyl, and linking groups; or
$R^3$ and $R^4$ are both independently selected from the group consisting of alkyl, cycloalkyl, aryl, arylalkyl, and linking groups; or
$R^{11}$ and $R^{12}$ are both independently selected from the group consisting of alkyl, cycloalkyl, aryl, arylalkyl, and linking groups; or
$R^{13}$ and $R^{14}$ are both independently selected from the group consisting of alkyl, cycloalkyl, aryl, arylalkyl, and linking groups.

In some embodiments of the foregoing, at least one or two of $R^1$, $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, $R^{17}$, $R^{18}$, $R^{21}$, $R^{22}$, $R^{31}$ and $R^{32}$ is, or are, independently selected bioconjugatable groups, targeting groups, surface attachment groups, or water soluble groups.

In some embodiments of the foregoing, at least one of $R^1$, $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, $R^{17}$, $R^{18}$, $R^{21}$, $R^{22}$, $R^{23}$, $R^{31}$ and $R^{32}$ is a bioconjugatable group or targeting group, and at least one other thereof is a water soluble group.

In some embodiments of the foregoing, one of $R^3$ and $R^4$ can be a water soluble group, and the other of $R^3$ and $R^4$ can be a bioconjugatable group or targeting group.

In some embodiments of the foregoing, one of $R^{13}$ and $R^{14}$ can be a water soluble group, and the other of $R^{13}$ and $R^{14}$ can be a bioconjugatable group or targeting group.

In some embodiments, such as some of the chlorins of Formulas DIb, DIb', and some of the bacteriochlorins of Formulas DIc, DIc', neither $R^1$ nor $R^2$ is H.

In some embodiments, such as some of the chlorins of Formulas DIb, DIb', and some of the bacteriochlorins of Formulas DIc, DIc', neither $R^3$ nor $R^4$ is H.

In some embodiments, such as some of the chlorins of Formulas DIb, DIb', and some of the bacteriochlorins of Formulas DIc, DIc', none of $R^1$, $R^2$, $R^3$ and $R^4$ is H.

In some embodiments, such as some of the bacterochlorins Formulas DIc, DIc', and some of the opp-chlorins of Formulas DId, DId', neither $R^{11}$ nor $R^{12}$ is H.

In some embodiments, such as some bacterochlorins Formula DIc, DIc', and some of the opp-chlorins of Formulas DId, DId', neither $R^{13}$ nor $R^{14}$ is H.

In some embodiments, such as some of the bacterochlorins Formula DIc, DIc', and some of the opp-chlorins of Formulas DId, DId', none of $R^{11}$, $R^{12}$, $R^{13}$ and $R^{14}$ is H.

In general, compounds of Formula DI as described above may be produced by (a) providing a compound of Formula DII:

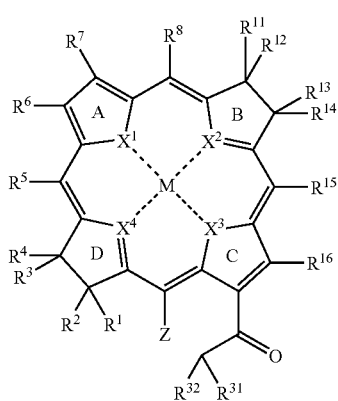

(DII)

wherein: Z is H or halo (such as bromo); and M, $X^1$, $X^2$, $X^3$, $X^4$, $R^1$, $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, $R^{31}$ and 32 are as given above;

(b) cyclizing said compound of Formula DII, typically by an intramolecular alpha arylation, to produce a cyclized product (that is, including the "E" ring as shown in DI); and (c) optionally deoxygenating the cyclized product; and then (d) optionally metalating the cyclized product to produce the compound of Formula DI. In some embodiments, $R^{31}$ and $R^{32}$ are each independently H, alkyl, or aryl; or one of $R^{31}$ and $R^{32}$ is H and the other is cyano; or one of $R^{31}$ and $R^{32}$ is H and the other is ester.

The cyclizing step is generally carried out in an organic solvent, optionally including water, by any suitable technique as discussed further below. For example, the cyclizing step may be carried out with a palladium catalyst in the presence of a base.

As also discussed further below, the compound of Formula DII may be produced by halogenating a compound of Formula DIII:

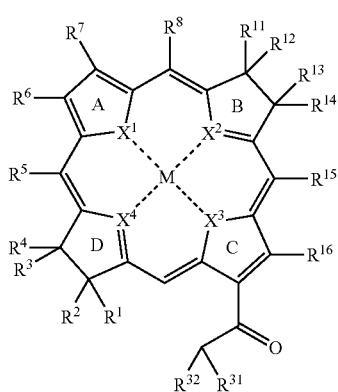

(DIII)

wherein M, $X^1$, $X^2$, $X^3$, $X^4$, $R^1$, $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, $R^{31}$ and $R^{32}$ are as given above. The compound of Formula DIII can be produced in accordance with known techniques or variations thereof which will be apparent to those skilled in the art based upon the present disclosure.

Intramolecular α-arylation ⁻(Pd-coupling): The intermolecular and intramolecular α-arylation of certain ketones with a halo group (e.g., Cl, Br, I) present at a suitable position for is known.

The intramolecular cyclization step of the present invention can be carried out in like manner, or variations thereof that will be apparent to those skilled in the art in view of the present disclosure.

In general the reaction involves a palladium catalyst and a base. Suitable palladium-catalysts include, but are not limited to, $Pd_2(dba)_3$/BINAP, $Pd_2(dba)_3$/Tol-BINAP, $Pd(OAc)_2$, $Pd_2(dba)_3$, $Pd_2(dba)_3$/2-(dicyclohexylphosphino)-biphenyl, $Pd(OAc)_2$/2-(dicyclohexylphosphino)-biphenyl, $Pd(OAc)_2$/2-(di-t-butylphosphino)-2'-methylbiphenyl, $Pd(dba)_2$/DTPE, $Pd(dba)_2$/DPPF, $Pd(OAc)_2$/Xantphos, $Pd(OAc)_2$/n-butylbis(1-adamantyl)-phosphine, $Pd(dba)_2$/n-butylbis(1-adamantyl)-phosphine, $Pd(OAc)_2$/$PPh_3$, $Pd(OAc)_2$/(4-$XC_6H_4)_3P$, $Pd_2(dba)_3$/Xantphos, $Pd(OAc)_2$/2-(Dicyclohexylphosphino)-2'-methylbiphenyl, $Pd(OAc)_2$/DPPP, $PdCl_2(Ph_3P)_2$, $PdCl_2$-[(o-Tol)$_3$]$_2$, $Pd(Ph_3P)_4$, $Pd(OAc)_2$/P(t-Bu)$_3$, $Pd_2(dba)_3$/$CHCl_3$/BINAP, and combinations thereof.

Suitable bases include, but are not limited to, t-BuONa, $NaN(SiMe_3)_2$, $KN(SiMe_3)_2$, $Cs_2CO_3$, $K_2CO_3$, $K_3PO_4$, diisopropylamine, NaH, NaOH, t-BuOK, TBAF, and combinations thereof.

Any suitable organic solvent, including polar and nonpolar, and protic or aprotic solvents, may be used for the reaction, optionally including water, with examples including but not limited to THF, toluene, benzene, xylene, DMF, dioxane, DMSO, 1-Butyl-3-methylimidazolium tetrafluoroborate, and combinations thereof. The reaction may be carried out at any suitable temperature, typically from 20 or 40° C. up to 140° C., or more.

See, e.g., Muratake, H. et al., *Tetrahedron Lett.* 1997, 38, 7577-7580; Muratake, H.; Natsume, M. *Tetrahedron Lett.* 1997, 38, 7581-7582; Muratake, H.; Nakai, H. *Tetrahedron Lett.* 1999, 40, 2355-2358; Muratake, H. et al., *Tetrahedron* 2004, 60, 11783-11803; Sole, D. et al., *Adv. Synth. Catal.* 2001, 343, 439-442; Sole, D. et al., *J. Am. Chem. Soc.* 2003, 125, 1587-1594; Sole, D. et al., *Chem. Commun.* 2001, 1888-1889; Sole, D. et al., *Org. Lett.* 2000, 2, 2225-2228; Ciufolini, M. A. et al., *J. Org. Chem.* 1988, 53, 4151-4153; Honda, T.; Sakamaki, Y. *Tetrahedron Lett.* 2005, 46, 6823-6825; See also, Palucki, M.; Buchwald, S. L. *J. Am. Soc. Chem.* 1997, 119, 11108-11109; Fox, J. M. et al., *J. Am. Soc. Chem.* 2000, 122, 1360-1370; Hamann, B. C.; Hartwig, J. F. *J. Am. Soc. Chem.* 1997, 119, 12382-12383; Carril, M. et al., *Org. Lett.* 2005, 22, 4787-4789; Ehrentraut, A. et al., *Adv. Synth. Catal.* 2002, 344, 209-217; Satoh, T. et al., *J. Organomet. Chem.* 2002, 653, 161-166; Wills, M. C. et al., *Angew. Chem. Int. Ed.* 2005, 44, 403-406; Diedrichs, N. et al., *Eur. J. Org. Chem.* 2005, 1731-1735; Mo, J. et al., *Tetrahedron* 2005, 61, 9902-9907; Singh, R.; Nolan, S. P. *J. Organomet. Chem.* 2005, 690, 5832-5840; Kosugi, M. et al., *J. Chem. Soc., Chem. Commun.* 1983, 344-345; Kuwajima, I.; Urabe, H. *J. Am. Soc. Chem.* 1982, 104, 6831-6833.

An efficient reaction condition was reported for the direct arylation of ketones by the use of aryl chlorides in the presence of the carbene-palladium catalyst [($Pd(OAc)_2$/N,N'-(2,6-diisopropyl phenyl) imidazole-2-ylidene] (Singh, R.; Nolan, S. P. *J. Organomet. Chem.* 2005, 690, 5832-5840), and the cyclizing step of the present invention can be carried out in like manner. Alternatively, the reaction of tributyltin enolates, prepared either from tributyltin methoxide and enol acetates or from silyl enol ethers and $Bu_3SnF$, in the presence of $PdCl_2[P(o-tolyl)_3]_2$ is reported to give α-arylated ketones (Kuwajima, I.; Urabe, H. *J. Am. Soc. Chem.* 1982, 104, 6831-6833), and the cyclizing step of the present invention can be carried out in like manner.

Photodriven nucleophilic aromatic substitution reaction: The α-arylation of ketones (intermolecular or intramolecular) has been studied by photostimulated nucleophilic aromatic substitution reaction of enolate anion with aryl halides, and the cyclizing step of the present invention can be carried out in like manner. The reaction is generally carried out in the presence of a base (suitable examples including but not limited to t-BuOK, $KNH_2$, $NaNH_2$, K, Na, Li, KH, $Ag_2O$, and mixtures thereof) in an organic solvent (suitable examples including but not limited to (liquid ammonia, THF, DME, ether, DMF, DMSO, benzene are commonly used solvents).

Still another approach for the intramolecular α-arylation of ketones involves the reaction of silyl enol ethers with the PET-generated arene radical cations.

See, e.g., Rossi, R. A.; Bunnett, J. F. *J. Org. Chem.* 1973, 38, 3020-3025; Bunnett, J. F.; Sundberg, J. E. *J. Org. Chem.* 1976, 41, 1702-1706; Komin, A. P.; Wolfe, J. F. *J. Org. Chem.* 1977, 42, 2481-2486; Moon, M. P.; Wolfe, J. F. *J. Org. Chem.* 1979, 44, 4081-4085; Sominelhack, M. F.; Bargar, T. M. *J. Org. Chem.* 1977, 42, 1481-1482; Semmelheck, M. F.; Bargar, T. *J. Am. Soc. Chem.* 1980, 102, 7765-7774; Pandey, G.; Karthikeyan, M.; Murugan, A. *J. Org. Chem.* 1998, 63, 2867-2872.

Other methods for α-arylation: A number of alternative routes have also been reported for the α-arylation of ketones, and the cyclizing step of the present invention can be carried out in like manner. For example:

(i) A nucleophilic aromatic substitution via Ni(II) catalyzed reaction of aryl halides with ketones has been reported (See, e.g., Semmelhack, M. F.; Stauffer, R. D.; Rogerson, T. D. *Tetrahedron Lett.* 1973, 4519-4522).

(ii) An alternative approach for the intramolecular α-arylation without halo substituents has been achieved with Mn(III) catalyst (See, e.g., Snider, B. B.; Cole, B. M. *J. Org. Chem.* 1995, 60, 5376-5377).

(iii) The electroreductive intramolcular cyclization of a carbonyl group to an activated carbon-carbon double bond has been described (no aryl halide is involved here) (See, e.g., Kise, N.; Suzumoto. T.; Shono, T. *J. Org. Chem.* 1994, 59, 1407-1413).

(iv) The electrophilic aromatic substitution of β-keto sulfoxides or tris(phenylthio)methane derivatives in the presence of an acid is known to give α-arylated ketones (no aryl halide is involved here) (See, e.g., Oikawa, Y.; Yonemitsu, O. *Tetrahedron* 1974, 30, 2653-2660; Oikawa, Y.; Yonemitsu, O. *J. Org. Chem.* 1976, 41, 1118-1124; Tamura, Y. et al., *Tetrahedron Lett.* 1981, 22, 81-84; Bin Manas, A. R.; Smith, R. A. J. *Tetrahedron* 1987, 43, 1856-1856).

In a particular embodiment, our synthetic route for installing the isocyclic ring entails four steps in addition to those required for macrocycle formation. The route is illustrated for chlorins in Scheme Z, with substituents omitted for clarity.

Step 1: introduction of a halogen, preferably a bromine atom, at the 8-position of an Eastern half precursor to the chlorin (not shown). (Note that the Eastern half ordinarily incorporates a bromine atom at the 9-position for macrocycle formation; hence, the Eastern half used herein contains two bromine substituents.) The chlorin macrocycle is then formed in the usual way, affording the corresponding 13-bromo-chlorin ($Br^{13}$-chlorin).

Step 2: Pd coupling with tributyl(ethoxyvinyl)tin, which upon acidic workup affords the corresponding 13-acetyl-chlorin ($Ac^{13}$-chlorin).

Step 3: Halogenation of the chlorin, which occurs preferentially at the 15-position, affording the 13-acetyl-15-halo-chlorin ($Ac^{13}X^{15}$-chlorin). Bromination is preferred. Note that the sites flanking the reduced, pyrroline ring are more reactive than any other sites in the macrocycle. The preference for 15-versus 20-substitution stems from steric hindrance imparted by the geminal dimethyl group at the 18-position.

Step 4: Intramolecular α-arylation via Pd coupling, which creates a carbon-carbon bond between the methyl group of the acetyl moiety, and the meso ($C^{15}$) carbon, yielding the $13^1$-oxophorbine.

An analogous approach is employed for synthesis of porphyrins or bacterichlorins bearing an isocyclic ring. A β-halo-dipyrromethane or dihydrodipyrrin precursor is prepared and employed to give the corresponding 13-halo-porphyrin or bacteriochlorin. The remaining steps 2-4 proceed as shown for the chlorin.

The keto group can be deoxygenated to give the phorbine (not shown). Typical methods of deoxygenation include (1) $TFA/NaBH_4$, or (2) reduction with $LiAlH_4$ (Abraham et al., *J. Chem. Soc. Perkin Trans.* 2, 1993, 1047-1059), or (3) reduction with $LiAlH_4$, tosylation, and reduction with $LiAlH_4$. Abraham et al. found that a chlorophyll analogue underwent deoxygenation upon treatment with $LiAlH_4$. A wide variety of other methods are known for deoxygenation of ketones.

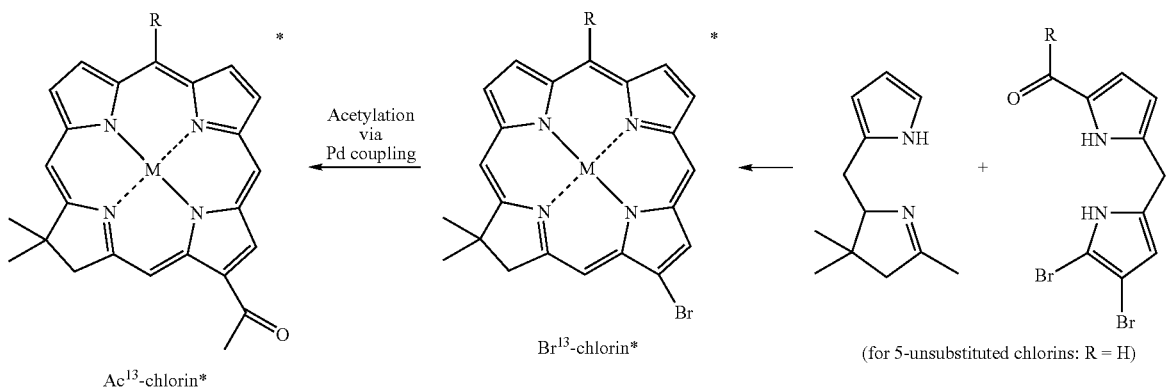

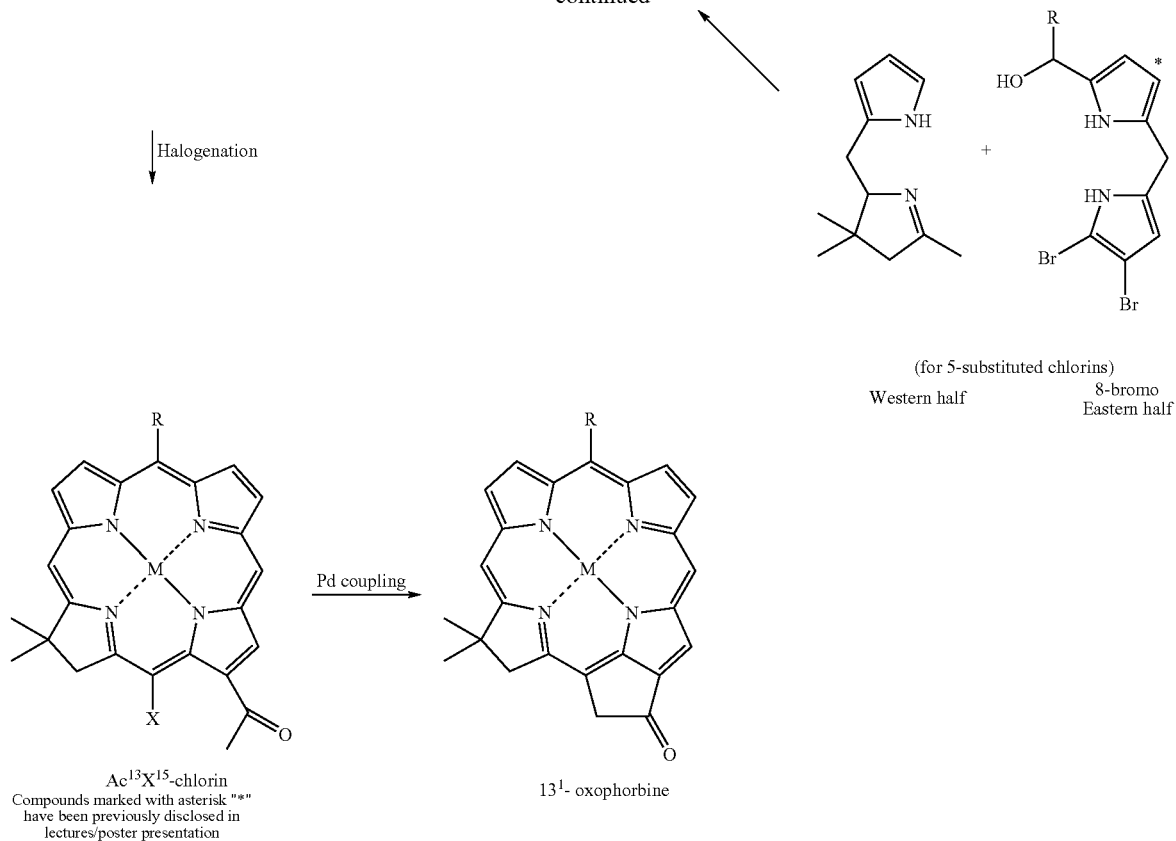

(for 5-substituted chlorins)
Western half
8-bromo Eastern half

Ac¹³X¹⁵-chlorin
Compounds marked with asterisk "*" have been previously disclosed in lectures/poster presentation 13¹-oxophorbine E. Metalation, Linking Groups, and Further Substitutions.

Porphyrinic compounds as described above may be metalated with any suitable metal in accordance with known techniques. See, e.g., U.S. Pat. No. 6,208,553. Suitable metals include but are not limited to Pd(II), Pt(II), Mg(II), Zn(II), Al(III), Ga(III), In(III), Sn(IV), Cu(II) (less preferred), Ni(II), and Au(III). Where the metal is trivalent or tetravalent a counterion is included as necessary in accordance with known techniques.

Linking groups for conjugates. Linking groups are included in compounds of the invention to provide a reactive site for conjugation so that the compounds may be coupled to or conjugated to other groups such as proteins, peptides, targeting agents such as antibodies, polymers, particles such as nanoparticles, organic, polymeric or inorganic beads, other solid support surfaces, etc., to form additional active compounds of the invention. In general each group is attached to a linking group including a linker which can be aryl, alkyl, heteroaryl, heteroalkyl (e.g., oligoethylene glycol), peptide, polysaccharide, etc. The linking group may be simply a reactive attachment group or moiety (e.g., —R' where R' is a reactive group such as bromo), or may comprise a combination of an intervening group coupled to a reactive group (e.g., —R"R', where R' is a reactive group and R" is an intervening group such as a hydrophilic group).

For bioconjugation purposes, the choice of water-solubilizing group(s) and conjugation groups is made so as to achieve orthogonal coupling. For example, if a carboxylic acid is used for water solubility, an aldehyde might be used for bioconjugation (via reductive amination with an amino-substituted biomolecule). If a carboxylic acid is used for bioconjugation (via carbodiimide-activation and coupling with an amino-substituted biomolecule), then a complementary group can be used for water solubility (e.g., sulfonic acid, guanidinium, pyridinium). Bioconjugatable groups include amines (including amine derivatives) such as isocyanates, isothiocyanates, iodoacetamides, azides, diazonium salts, etc., acids or acid derivatives such as N-hydroxysuccinimide esters (more generally, active esters derived from carboxylic acids; e.g., p-nitrophenyl ester), acid hydrazides, etc., and other linking groups such as aldehydes, sulfonyl chlorides, sulfonyl hydrazides, epoxides, hydroxyl groups, thiol groups, maleimides, aziridines, acryloyls, halo groups, biotin, 2-Iminobiotin, etc. Linking groups such as the foregoing are known and described in U.S. Pat. Nos. 6,728,129; 6,657,884; 6,212,093; and 6,208,553.

Conjugates. Other groups can be attached to the active compounds to form a conjugate by means of a linking group to tune or adjust the solubility properties of the active compounds, including hydrophobic groups, hydrophilic groups, polar groups, or amphipathic groups. The polar groups include carboxylic acid, sulfonic acid, guanidinium, carbohydrate, hydroxy, amino acid, pyridinium, imidazolium, etc. Such groups can be attached to substituents that are linear or branched alkyl (e.g., swallowtail), aryl, heteroaryl, heteroalkyl (e.g., oligoethylene glycol), peptide, polysaccharide, etc. Targeting groups such as antibodies, proteins, peptides, and nucleic acids may be attached by means of the linking group. Particles such as nanoparticles, glass beads, etc. may be attached by means of the linking group. Where such additional compounds are attached to form a conjugate that may be attached directly to the active compound or attached by means of an intervening group such as a hydrophilic group, depending upon the particular linking group employed (as noted above).

Hydrophilic groups. Compounds of the present invention may include hydrophilic groups coupled at the linking sites noted above, e.g., covalently coupled thereto, to facilitate delivery thereof, or improve stability, in accordance with known techniques (e.g., to the N-terminus of the peptide). Suitable hydrophilic groups are typically polyols or polyalkylene oxide groups, including straight and branched-chain polyols, with particularly examples including but not limited to poly(propylene glycol), polyethylene-polypropylene glycol or poly(ethylene glycol). The hydrophilic groups may have a number average molecular weight of 20,000 to 40,000 or 60,000. Suitable hydrophilic groups and the manner of coupling thereof are known and described in, for example, U.S. Pat. Nos. 4,179,337; 5,681,811; 6,524,570; 6,656,906; 6,716,811; and 6,720,306. For example, compounds can be pegylated using a single 40,000 molecular weight polyethylene glycol moiety that is attached to the compound by means of a linking group.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Active compounds of the invention can be provided as pharmaceutically acceptable salts. Such salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

Ligands. In another embodiment, the disclosed compounds may be targeted to specific target tissues or target compositions using ligands specific for the target tissue or target composition, for example, using ligands or ligand-receptor pairs such as antibodies and antigens. Antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg, U.S. Pat. Nos. 4,331,647; 4,348,376; 4,361,544; 4,468,457; 4,444,744; 4,818,709 and 4,624,846. Antibodies against an antigen, e.g., a gastrointestinal, lung, breast, prostate, ovarian, testicular, brain or lymphatic tumor, a sarcoma or a melanoma, can be used.

A wide variety of monoclonal antibodies against infectious disease agents have been developed, and are summarized in a review by Polin, in Eur. J. Clin. Microbiol., 3(5): 387-398 (1984), showing ready availability. These include monoclonal antibodies (MAbs) against pathogens and their antigens such as the following: Anti-bacterial Mabs such as those against *Streptococcus agalactiae, Legionella pneumophilia, Streptococcus pyogenes, Esherichia coli, Neisseria gonorrhosae, Neisseria meningitidis, Pneumococcus, Hemophilis influenzae* B, *Treponema pallidum*, Lyme disease, spirochetes, *Pseudomonas aeruginosa, Mycobacterium leprae, Brucella abortus, Mycobacterium tuberculosis*, Tetanus toxin, Anti-protozoan Mabs such as those against *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Mesocestoides corti, Emeria tenella, Onchocerca volvulus, Leishmania tropica, Trichinella spiralis, Theileria parva, Taenia hydatigena, Taenia ovis, Taenia saginata*, Anti-viral MAbs such as those against HIV-1, -2, and -3, Hepatitis A, B, C, D, Rabies virus, Influenza virus, Cytomegalovirus, Herpes simplex I and II, Human serum parvo-like virus, Respiratory syncytial virus, Varicella-Zoster virus, Hepatitis B virus, Measles virus, Adenovirus, Human T-cell leukemia viruses, Epstein-Barr virus, Mumps virus, Sindbis virus, Mouse mammary tumor virus, Feline leukemia virus, Lymphocytic choriomeningitis virus, Wart virus, Blue tongue virus, Sendai virus, Reo virus, Polio virus, Dengue virus, Rubella virus, Murine leukemia virus, Antimycoplasmal MAbs such as those against *Acholeplasma laidlawii, Mycoplasma arthritidis, M. hyorhinis, M. orale, M. arginini, M. pneumonia*; etc.

Suitable MAbs have been developed against most of the micro-organisms (bacteria, viruses, protozoa, other parasites) responsible for the majority of infections in humans, and many have been used previously for in vitro diagnostic purposes. These antibodies, and newer MAbs that can be generated by conventional methods, are appropriate for use as target agents with the compounds provided herein.

MAbs against malaria parasites can be directed against the sporozoite, merozoite, schizont and gametocyte stages. Monoclonal antibodies have been generated against sporozoites (circumsporozoite antigen), and have been shown to neutralize sporozoites in vitro and in rodents (N. Yoshida et al., Science 207: 71-73 (1980)). Monoclonal antibodies to *T. gondii*, the protozoan parasite involved in toxoplasmosis have been developed (Kasper et al., J. Immunol. 129: 1694-1699 (1982). MAbs have been developed against schistosomular surface antigens and have been found to act against schistosomulae in vivo or in vitro (Simpson et al., Parasitology 83: 163-177 (1981); Smith et al., Parasitology 84: 83-91 (1982); Gryzch et al., J. Immunol. 129: 2739-2743 (1982); Zodda et al., J. Immunol. 129: 2326-2328 (1982); Dissous et al., J. Immunol. 129: 2232-2234 (1982).

It should be noted that mixtures of antibodies and immunoglobulin classes can be used, as can hybrid antibodies. Multispecific, including bispecific and hybrid, antibodies and antibody fragments are especially preferred in the methods of the present invention for detecting and treating target tissue and are comprised of at least two different substantially monospecific antibodies or antibody fragments, wherein at least two of said antibodies or antibody fragments specifically bind to at least two different antigens produced or associated with the targeted lesion or at least two different epitopes or molecules of a marker substance produced or associated with the target tissue. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., Immunol. Today 5: 299 (1984).

Antibody fragments useful in the present invention include $F(ab')_2$, $F(ab)_2$, Fab', Fab, Fv and the like including hybrid fragments. Preferred fragments are Fab', $F(ab')_2$, Fab, and $F(ab)_2$. Also useful are any subfragments retaining the hypervariable, antigen-binding region of an immunoglobulin and having a size similar to or smaller than a Fab' fragment. This will include genetically engineered and/or recombinant proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of $F(ab')_2$ fragments, which themselves may be made by pepsin digestion of intact immunoglobulin. Fab antibody fragments may be made by papain digestion of intact immunoglobulin, under reducing conditions, or by cleavage of $F(ab)_2$ fragments which result from careful papain digestion of whole immunoglobulin.

A ligand or one member of a ligand-receptor binding pair can be conjugated to the compounds provided herein for targeting the compounds to specific target tissues or target compositions. Examples of ligand-receptor binding pairs are set out in U.S. Pat. Nos. 4,374,925 and 3,817,837, the teachings of which are incorporated herein by reference.

Conjugation to ligands. Many compounds that can serve as targets for ligand-receptor binding pairs, and more specifically, antibodies, have been identified, and the techniques to construct conjugates of such ligands with photosensitizers are well known to those of ordinary skill in this art. For example, Rakestraw et al. teaches conjugating Sn(IV) chlorin e via covalent bonds to monoclonal antibodies using a modified dextran carrier (Rakestraw, S. L., Tompkins, R. D., and Yarmush, M. L., Proc. Nad. Acad. Sci. USA 87: 4217-4221 (1990). The compounds disclosed herein can also be conjugated to a ligand, such as an antibody, by using a coupling agent. Any bond which is capable of linking the components such that they are stable under physiological conditions for the time needed for administration and treatment is suitable, but covalent linkages are preferred. The link between two components may be direct, e.g., where a photosensitizer is linked directly to a targeting agent, or indirect, e.g., where a photosensitizer is linked to an intermediate and that intermediate being linked to the targeting agent.

A coupling agent should function under conditions of temperature, pH, salt, solvent system, and other reactants that substantially retain the chemical stability of the photosensitizer, the backbone (if present), and the targeting agent. Coupling agents should link component moieties stably, but such that there is only minimal or no denaturation or deactivation of the photosensitizer or the targeting agent. Many coupling agents react with an amine and a carboxylate, to form an amide, or an alcohol and a carboxylate to form an ester. Coupling agents are known in the art (see, e.g., M. Bodansky, "Principles of Peptide Synthesis", 2nd ed., and T. Greene and P. Wuts, "Protective Groups in Organic Synthesis," 2nd Ed, 1991, John Wiley, NY).

The conjugates of the compounds provided herein with ligands such as antibodies can be prepared by coupling the compound to targeting moieties by cleaving the ester on the "d" ring and coupling the compound via peptide linkages to the antibody through an N terminus, or by other methods known in the art. A variety of coupling agents, including cross-linking agents, can be used for covalent conjugation. Examples of cross-linking agents include N,N'-dicyclohexylcarbodiimide (DCC), N-succinimidyl-5-acetyl-thioacetate (SATA), N-succinimidyl-3-(2-pyridyldithio)propionate (SPDP), ortho-phenylene-dimaleimide (o-PDM), and sulfo-succinimidyl 4-(N-maleimido-methyl)-cyclohexane-1-carboxylate (sulfo-SMCC). See, e.g., Karpovsky et al. J. Exp. Med. 160:1686 (1984); and Liu, M A et al., Proc. Natl. Acad. Sci. USA 82: 8648 (1985). Other methods include those described by Brennan et al. Science 229: 81-83 (1985) and Glennie et al., J. Immunol. 139: 2367-2375 (1987). A large number of coupling agents for peptides and proteins, along with buffers, solvents, and methods of use, are described in the Pierce Chemical Co. catalog, pages O-90 to O-110 (1995, Pierce Chemical Co., 3747 N. Meridian Rd., Rockford Ill., 61105, U.S.A.), which catalog is hereby incorporated by reference.

For example, DCC is a useful coupling agent that can be used to promote coupling of the alcohol NHS to chlorin $e_6$ in DMSO forming an activated ester which can be cross-linked to polylysine. DCC is a carboxy-reactive cross-linker commonly used as a coupling agent in peptide synthesis, and has a molecular weight of 206.32. Another useful cross-linking agent is SPDP, a heterobifunctional cross-linker for use with primary amines and sulfhydryl groups. SPDP has a molecular weight of 312.4, a spacer arm length of 6.8 angstroms, is reactive to NHS-esters and pyridyldithio groups, and produces cleavable cross-linking such that, upon further reaction, the agent is eliminated so the photosensitizer can be linked directly to a backbone or targeting agent. Other useful conjugating agents are SATA for introduction of blocked SH groups for two-step cross-linking, which is deblocked with hydroxylamine-HCl, and sulfo-SMCC, reactive towards amines and sulfhydryls. Other cross-linking and coupling agents are also available from Pierce Chemical Co. Additional compounds and processes, particularly those involving a Schiff base as an intermediate, for conjugation of proteins to other proteins or to other compositions, for example to reporter groups or to chelators for metal ion labeling of a protein, are disclosed in EPO 243,929 A2 (published Nov. 4, 1987).

Photosensitizers which contain carboxyl groups can be joined to lysine ε-amino groups in the target polypeptides either by preformed reactive esters (such as N-hydroxy succinimide ester) or esters conjugated in situ by a carbodiimide-mediated reaction. The same applies to photosensitizers which contain sulfonic acid groups, which can be transformed to sulfonyl chlorides which react with amino groups. Photosensitizers which have carboxyl groups can be joined to amino groups on the polypeptide by an in situ carbodiimide method. Photosensitizers can also be attached to hydroxyl groups, of serine or threonine residues or to sulfhydryl groups of cysteine residues.

Methods of joining components of a conjugate, e.g., coupling polyamino acid chains bearing photosensitizers to antibacterial polypeptides, can use heterobifunctional cross linking reagents. These agents bind a functional group in one chain and to a different functional group in the second chain. These functional groups typically are amino, carboxyl, sulfhydryl, and aldehyde. There are many permutations of appropriate moieties which will react with these groups and with differently formulated structures, to conjugate them together. See the Pierce Catalog, and Merrifield, R. B. et al., Ciba Found Symp. 186: 5-20 (1994).

The compounds or pharmaceutically acceptable derivatives thereof may be packaged as articles of manufacture containing packaging material, a compound or pharmaceutically acceptable derivative thereof provided herein, which is effective for modulating the activity of hyperproliferating tissue or neovascularization, or for treatment, prevention or amelioration of one or more symptoms of hyperproliferating tissue or neovascularization mediated diseases or disorders, or diseases or disorders in which hyperproliferating tissue or neovascularization activity, is implicated, within the packaging material, and a label that indicates that the compound or composition, or pharmaceutically acceptable derivative thereof, is used for modulating the activity of hyperproliferating tissue or neovascularization, or for treatment, prevention or amelioration of one or more symptoms of hyperproliferating tissue or neovascularization mediated diseases or disorders, or diseases or disorders in which hyperproliferating tissue or neovascularization is implicated.

Detection Techniques.

Active compounds of the present invention can be detected by any suitable technique, including but not limited to flow cytometry, fluorescence spectroscopy, with a multi-well fluorescent plate scanner, scanning cytometry, fluorescent or immunofluorescent microscopy, laser scanning cytometry, bright field base image analysis, capillary volumetry, manual cell analysis and automated cell analysis. See, e.g., U.S. Pat. Nos. 5,314,805; 6,551,788 and 6,623,982.

Flow cytometry. Flow cytometry is known and described in, for example, U.S. Pat. Nos. 2,656,508; 2,869,078; 3,271,671; 5,915,925; 6,248,590; 6,524,860; 6,589,792; 6,604,435; and 6,890,487. In some embodiments the particle being detected, such as a cell, is labelled with a luminescent compound such as a phosphor or fluorophore for detection. Labelling can be carried out by any suitable technique such as coupling the luminescent compound to another compound such as an antibody which in turn specifically binds to the particle or cell, by uptake or internalization of the luminescent compound into the cell or particle, by non-specific adsorption of the luminescent compound to the cell or particle, etc. The active compounds described herein are useful in flow cytometry as such luminescent compounds, which flow cytometry techniques (including fluorescent activated cell sorting or FACS) may be carried out in accordance with known techniques or variations thereof which will be apparent to those skilled in the art based upon the instant disclosure.

The choice of particular porphyrin compounds as markers in diagnostic applications requires consideration of a variety of factors. The useful brightness of a dye depends on issues including (1) fundamental photophysical parameters (the product of the molar absorption coefficient at the wavelength of illumination ($\lambda_{exc}$) and the fluorescence quantum yield of non-aggregated species; the separation of absorption and emission bands; photostability, etc.), (2) the photon flux at the sample (which depends on wavelength and absorption by any interfering species), and (3) the concentration of non-aggregated absorber at the site of illumination (which depends on solubility and targeting efficacy).

In addition to brightness, consideration also is given to sensitivity and selectivity over background or other emitting species. Such considerations are especially important in multicolor applications, where more than one dye marker may be employed yet spectral and/or lifetime discrimination is essential.

Another practical factor concerns the industry-installed base of diagnostic instruments, which may have certain excitation sources and detectors. There are commercial advantages of dyes with superior chemical and conjugating attributes yet have spectral features that match the installed base of diagnostic instrumentation.

In many instances, a sizable spacing between the absorption band (for excitation) and the emission band (for detection) is desired, so as to avoid interference from light scattering by the sample.

In many instances, relatively sharp absorption and emission bands are desired, so that a large number of dye markers can be used in a given spectral region.

Porphyrinic macrocycles have a number of very attractive spectral attributes. Porphyrins exhibit absorption bands representing the transitions from the ground state to the first excited singlet state (Q band), and the second excited singlet state (B band). The B band(s) lie in the near-UV region. The Q band(s) lie in the visible or near-IR (NIR) region. Regardless of wavelength of excitation, the dominant emission occurs from the first excited singlet state. Accordingly, excitation in the near-UV results in emission in the red or NIR regions. By exploitation of the intrinsic photophysical features of porphyrinic macrocycles, a large spacing between absorption and emission can be achieved. Several examples are provided below:

(1) a trans-AB-porphyrin can be illuminated at ~405 nm (B band, $\epsilon_{405\ nm} \geq 200{,}000$ or $300{,}000\ M^{-1}cm^{-1}$) with emission in the 590-650 nm region ($\Phi_f$~0.03- or 0.15). Although the emission is relatively weak by comparison with that of many popular dyes, the product of absorption and emission, which underlies brightness, is substantial; moreover, the large spacing between excitation and emission ensures discrimination against light scattering.

(2) a bacteriochlorin can be illuminated in the B band (360-430 nm, $\epsilon \sim 100{,}000\ M^{-1}cm^{-1}$) with emission in the 750 nm region ($\Phi_f \sim 0.15$). Although the emission is relatively weak by comparison with that of many popular dyes, the product of absorption and emission, which underlies brightness, is substantial; moreover, the large spacing between excitation and emission ensures discrimination against light scattering.

(3) a bacteriochlorin can be illuminated in the $Q_x$ band at $\sim 500$-$520$ nm ($\epsilon \sim 20{,}000\ M^{-1}cm^{-1}$) with emission in the 750 nm region ($\Phi_f \_ 0.15$). The large spacing between excitation and emission ensures discrimination against light scattering.

(4) a bacteriochlorin can be illuminated in the $Q_y$ band ($\sim 735\ \mu m$, $\epsilon_{735\ nm} \sim 120{,}000\ M^{-1}cm^{-1}$) with emission in the 745 nm region ($\Phi_f \sim 0.15$). An attractive feature of this approach lies in the use of NIR excitation, which affords deep penetration into a sample without interference with naturally absorbing pigments (e.g., heme). The relatively sharp spectral bands ($\leq 25$ nm fwhm) greatly facilitate this application.

(5) a series of chlorins can be prepared with systematic gradation of absorption and emission bands; such chlorins are ideal for use in multicolor applications. The systematic gradation in spectral attributes can be achieved by use of auxochromic groups and variation of the centrally coordinated metal. The absorption and emission bands are relatively sharp ($<25$ nm fwhm); and the absorption bands can be tuned from $\sim 600$-$700$ nm and the emission bands can be tuned from $\sim 610$-$750$ nm. Accordingly, a handful of such chlorins can be used in a single multicolor application. Excitation of a set of such chlorins can be achieved with broad-band illumination (of all chlorins) in the blue region (exciting into the second excited singlet state), thereby avoiding scattered light upon detection of the specific emission band of each chlorin. Alternatively, discrete frequencies can be used in the red region to preferentially illuminate a given chlorin, with selective detection of the emission of a given chlorin.

(6) similarly, a series of bacteriochlorins can be prepared with systematic gradation of absorption and emission bands for use in multicolor applications. The absorption and emission bands are relatively sharp ($<25$ nm fwhm); and the absorption bands can be tuned from $\sim 720$-$850$ nm and the emission bands can be tuned from $\sim 730$-$900$ nm. Accordingly, a handful of such bacteriochlorins can be used in a single multicolor application. Excitation of a set of such bacteriochlorins can be achieved with broad-band illumination (of all bacteriochlorins) in the B bands or the $Q_x$ bands, thereby avoiding scattered light upon detection of the specific emission band of each chlorin. Alternatively, discrete frequencies can be used in the NIR region to preferentially illuminate a given bacteriochlorin, with selective detection of the emission of a given bacteriochlorin.

The present invention is explained in greater detail in the following non-limiting Examples.

Example 1

Installation of the Isocyclic Ring on Chlorins

We have been working to develop synthetic methods for preparing chlorins that can be used in diverse applications.[16-18] The synthesis of chlorins bearing a 5-substituent (alkyl or aryl) rely upon condensation of a 1-bromo-dipyrromethane-9-carbinol (Eastern half) and a 2,3,4,5-tetrahydro-1,3,3-trimethyldipyrrin (Western half).[17] Chlorins lacking a 5-substituent can be prepared by condensation of a 1-bromo-dipyrromethane-9-carboxaldehyde (Eastern half) and a 2,3,4,5-tetrahydro-1,3,3-trimethyldipyrrin (Western half).[18] Each chlorin incorporates a geminal dimethyl moiety in the reduced, pyrroline ring, thereby locking-in the hydrogenation level of the tetrapyrrole macrocycle at the dihydroporphyrin (i.e., chlorin) stage. These routes have enabled rational introduction of substituents at every peripheral site with the exception of the 7-position.[16-22] Given the difficulties of installing an isocyclic ring on the chlorin macrocycle, we previously investigated the effects of other, more accessible substituents that might afford enhanced red absorption spectral features. In this regard, 3-vinyl, 3-ethynyl, 13-ethynyl, and 13-acetyl groups were investigated and found to have pronounced effects on the spectral properties of the chlorin macrocycle.[22]

Results and Discussion

I. Synthesis. In the previous paper,[22] we prepared an 8,9-dibromo derivative of a 1-formyldipyrromethane (Eastern half), which upon acid-catalyzed condensation with a tetrahydrodipyrrin Western half followed by metal-mediated oxidative cyclization afforded the corresponding 13-bromo-chlorin. Pd-mediated coupling of the latter with tributyl(1-ethoxyvinyl)tin and subsequent acidic workup gave the 13-acetylchlorin. We employed a similar strategy here, but with use of an Eastern half bearing a 1-carbinol group. The resulting chlorin incorporates two meso substituents in addition to the 13-acetyl group.

Chlorin Precursors. An 8,9-dibromo derivative of a 1-acyldipyrromethane was prepared as shown in Scheme 2. Treatment of 5-mesityldipyrromethane (3)[23] with 3.0 molar equiv of EtMgBr at room temperature followed by Mukaiyama reagent 4[24] at $-78°$ C. gave the 1-acyldipyrromethane 5 in 73% yield. This route is superior to a prior acylation of 3 with p-toluoyl chloride that afforded 5 in 37% yield.[17] Treatment of 5 with 2.2 molar equiv of NBS at $-78°$ C. gave the dibromo-product 6 along with several side products. Compound 6, although quite labile, was handled effectively by workup without heating and by avoiding adverse solvents (ethyl acetate, chlorinated hydrocarbons). In so doing, workup including column chromatography afforded 6 in 57% yield.

Scheme 2

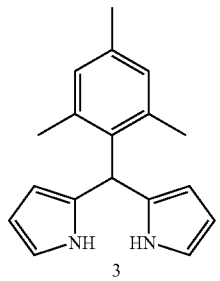

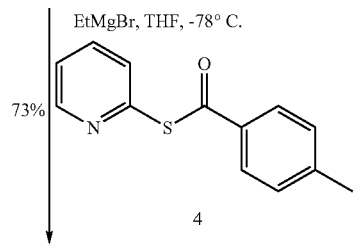

EtMgBr, THF, -78° C.

73%

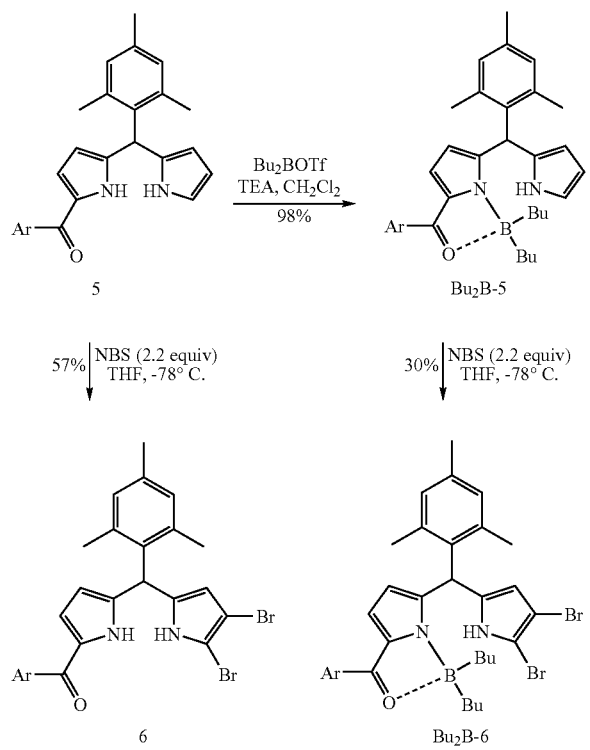

The regiochemistry of the 1,2-dibromo-substitution pattern in 6 was established by NMR spectroscopy ($^1$H-$^1$H 2D-COSY and 1D-NOE experiments). The regioselective formation of dibromo-product 6 can be explained in part by the fact that the α-acylpyrrole ring is deactivated, whereupon substitution takes place exclusively in the non-deactivated pyrrole ring at the vicinal α- and β-positions. The purified compound 6 decomposed almost completely within 8-10 hours in solution even at 0° C., but was stable as a powdered solid upon storage at −10° C. for 1-2 days. Compound 6 decomposed several times during NMR measurements (regardless of solvent such as CDCl$_3$, C$_6$D$_6$ or THF-d$_8$) or attempted crystallization. The corresponding dibutylboron complex[25] of the 1-acyldipyrromethane 5 (BBu$_2$-5) was prepared and converted to the 8,9-dibromo product (BBu$_2$-6) but no significant increase in stability was achieved. It should be noted that the synthesis of the 1-acyl-8,9-dibromodipyrromethane was inspired by the occurrence and demonstrated synthesis of analogous polyhalogenated pyrroles from marine organisms.[26] However, in most such pyrroles, the halogens and the acyl group are located in the same pyrrole, which must be considerably stabilized by the acyl group.

Chlorin Formation. Although we were concerned that the limited stability of 6 might prevent conversion to the chlorin, we proceeded with the synthesis (Scheme 3).

Reduction of 6 with NaBH$_4$ at room temperature for 3 h gave the corresponding dipyrromethane-1-carbinol (Eastern half). The completion of reduction can be monitored by TLC analysis (hexanes/ethyl acetate=3/1). The resulting dipyrromethane-monocarbinol is quite labile but was handled effectively in the same manner as for 6. The crude product was condensed with Western half 7 under the standard conditions of TFA catalysis. The putative tetrahydrobilene-a formed in situ was subjected to metal-catalyzed oxidative cyclization in the presence of air. After the formation of tetrahydrobilene a, 2,2,6,6-tetramethylpiperidine was added slowly at 0° C. followed by Zn(OAc)$_2$ and AgOTf. The resulting mixture was refluxed for 18 h exposed to air. In this manner, the zinc chelate of the 13-bromochlorin (Zn-8) was isolated in 14% yield from the dibromo derivative 6.

Scheme 3

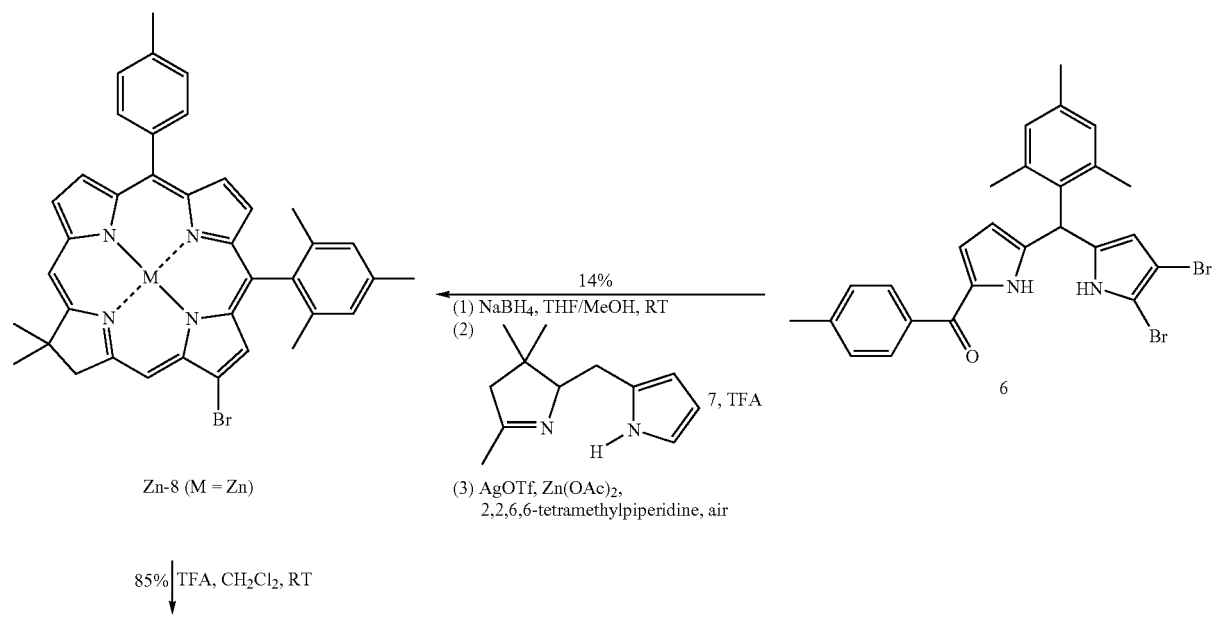

8 (M = H, H)

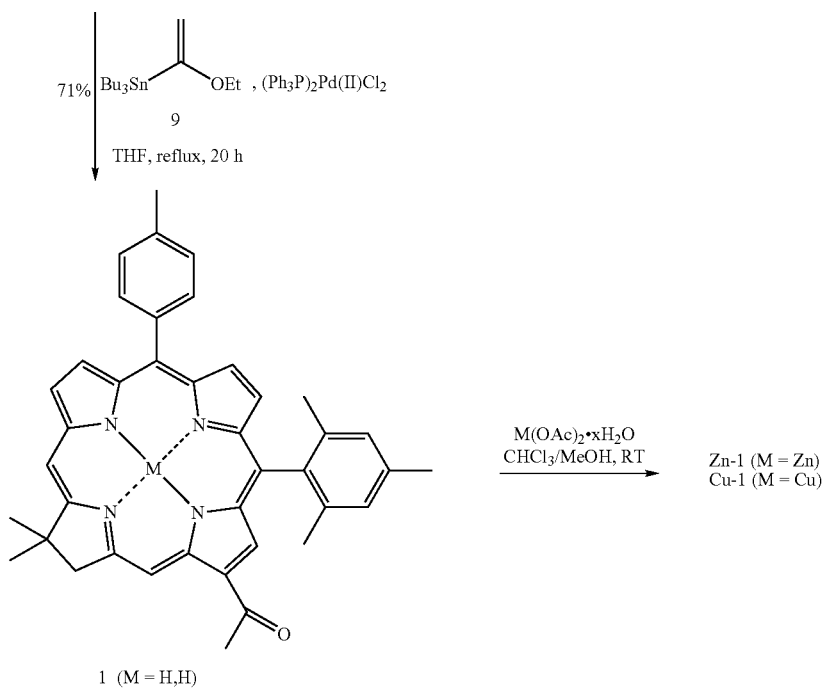

1 (M = H,H)

The conversion of the 13-bromochlorin Zn-8 to the 13-acetylchlorin is shown in Scheme 3. A limited amount of optimization proved necessary. Thus, heating a reaction mixture of Zn-8 (10 mM), tributyl(1-ethoxyvinyl)tin (9)[27] (12 mM) and 10 mol % of (PPh$_3$)$_2$PdCl$_2$ at 85° C. in toluene for 20 h followed by hydrolysis of the reaction mixture with 10% aqueous HCl gave 1 in 7% yield along with the recovery of free base 13-bromo chlorin 8 (~55% yield). Changing the solvent from toluene to THF and heating the reaction mixture at 55° C. for 20 h gave little improvement (17%). A somewhat better result was observed when the mixture of Zn-8 (20 mM), 9 (40 mM) and 20 mol % of (PPh$_3$)$_2$PdCl$_2$ was heated at 55° C. in THF for 36 h, whereupon 1 was isolated in 29% yield along with the recovery of free-base 13-bromo chlorin 8 (~22%). The synthesis of 1 was further improved by carrying out the palladium coupling using free base chlorin 8. Thus, demetalation of Zn-8 with TFA in CH$_2$Cl$_2$ at room temperature gave free-base 13-bromochlorin 8 in 85% yield. The coupling of 8 (10 mM) and 9 (20 mM) was carried out in the presence of 10 mol % of (PPh$_3$)$_2$PdCl$_2$ in THF for 20 h. Hydrolysis of the reaction mixture with 10% aqueous HCl and standard workup gave 13-acetylchlorin 1 in 71% yield. Compound 1 was characterized by absorption and fluorescence spectroscopy, $^1$H NMR spectroscopy, LD-MS and FAB-MS analyses. The free-base 13-acetylchlorin 1 was metalated with Zn(OAc)$_{2-2}$H$_2$O or Cu(OAc)$_2$.H$_2$O to obtain Zn-1 or Cu-1, respectively. The X-ray structure of Cu-1 confirmed the presence of the acetyl group at the 13-position of the chlorin macrocycle (not shown).

Isocyclic Ring Installation. The installation of the isocyclic ring on free-base 13-acetylchlorin 1 was envisaged by the intramolecular ring closure of the 13-acetyl group to the 15-position of the chlorin macrocycle. The α-arylation of aliphatic ketones is well known and has been carried out on a wide variety of aryl substrates. Such reactions have been carried out recently using (PPh$_3$)$_2$PdCl$_2$ in the presence of Cs$_2$CO$_3$ in THF at reflux.[28] The successful intramolecular ring closure of the 13-acetyl group to the 15-position of the chlorin macrocycle requires a bromo substituent at the 15-position. Recently, the selective halogenation of chlorins at the 15-position followed by palladium coupling reactions enabled introduction of 15-aryl substituents.[21] Treatment of 1 with 1 equiv of NBS at room temperature for 2 h gave the 15-bromochlorin 10 in 73% yield. Treatment of the crude 15-bromochlorin with (PPh$_3$)$_2$PdCl$_2$ in the presence of Cs$_2$CO$_3$ in THF at reflux resulted in intramolecular cyclization to form phorbine 2 in 44% overall yield from 1 (Scheme 4). Phorbine 2 was characterized by absorption and fluorescence spectroscopy, IR and $^1$H NMR spectroscopy, LD-MS, and FAB-MS analysis.

A novel feature of this ring-closure process with regards to the α-arylation of aliphatic ketones is that the product is ortho-perifused rather than merely ortho-fused. The simplicity of this transformation makes this route quite attractive as a means of installing the isocyclic ring. For perspective, it should be mentioned that Smith and coworkers subjected a porphyrin bearing substituents at all β-positions except position 13 to mercuration followed by palladium coupling with methyl acrylate, affording the 13-acrylate porphyrin.[29] This early approach for derivatizing the 13-position is suited for porphyrinic molecules bearing a single β-unsubstituted site. By contrast, the route described herein builds in the requisite functionality at the dipyrromethane stage, enabling derivatization of a chlorin macrocycle containing a defined pattern of substitution with many unsubstituted β-sites.

Scheme 4

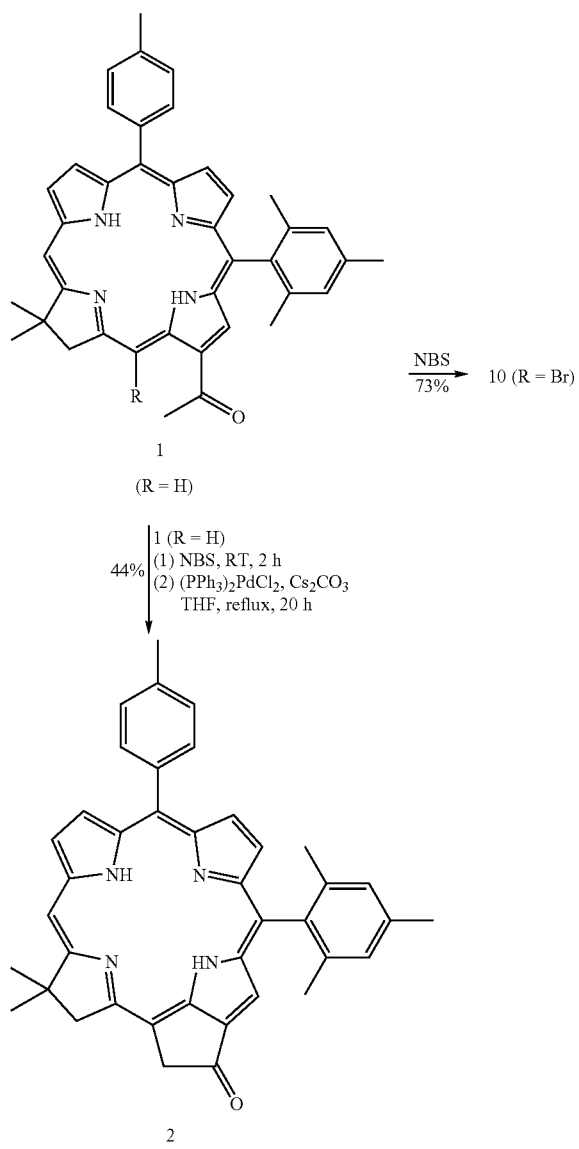

Chart 3

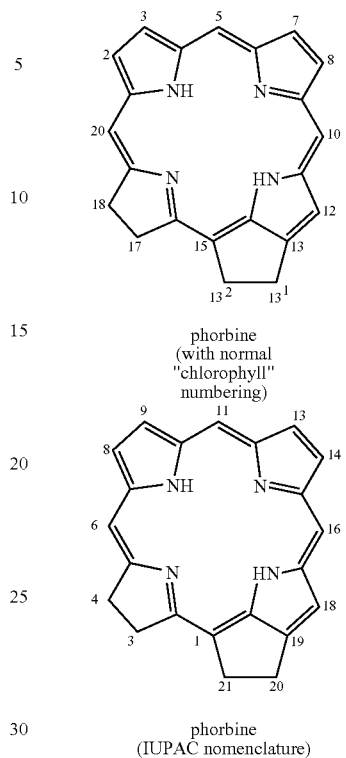

phorbine
(with normal "chlorophyll" numbering)

phorbine
(IUPAC nomenclature)

II. Nomenclature. The nomenclature for chlorophyll-like compounds understandably relies very heavily on trivial names for derivatives and degradation products of chlorophyll. The ring system for phorbine, which is recognized by IUPAC, provides a versatile parent hydrocarbon for naming chlorins containing an isocyclic ring, including those described herein. However, the IUPAC definition for phorbine adheres to a numbering system that is at odds with the universally accepted numbering system for porphyrins and chlorins.[30] We have adopted the phorbine ring system shown as the parent hydrocarbon for naming purposes, but with use of the more reasonable chlorophyll-derived numbering system (Chart 3). Alternatively, the chlorin containing an isocyclic ring can be named as a derivative of a porphyrin while again maintaining the chlorophyll-derived numbering system. Thus, compound 2 is a $13^1$-oxophorbine, or, alternatively, a $13^1,13^2,17,18$-tetrahydro-$13^1$-oxocyclopenta[m,n]porphine.

III. Spectral Properties.

IR Spectroscopy. IR spectroscopy can provide valuable information about the conjugation of the 13-keto group with the chlorin macrocycle. 13-Acetylchlorin 1 exhibits a carbonyl stretch ($v_{max}$) at 1728 cm$^{-1}$ (KBr), whereas that of phorbine 2 appears at 1701 cm$^{-1}$ (KBr). For comparison, the carbonyl stretch of analogous compounds includes 3-acetyl-2-methylpyrrole (1639 cm$^{-1}$),[31] acetophenone (1683 cm$^{-1}$), pheophytin a (1705 cm$^{-1}$),[32] methyl pheophorbide a (1703 cm$^{-1}$),[32] and methyl pyropheophorbide a (1695 cm$^{-1}$).[32] A reasonable interpretation is that the keto group in simple aromatic compounds is more conjugated with the aromatic nucleus, and has greater single-bond character, compared to that of the synthetic or naturally occurring phorbines (i.e., 2 and the chlorophyll derivatives). Not surprisingly, the keto group in 13-acetylchlorin 1 is less conjugated than that in phorbine 2.

Absorption Spectra. The spectral properties of interest in the chlorins include the position of the long-wavelength $Q_y$ transition, the intensity of the $Q_y$ transition, and the fluorescence quantum yield of the chlorin. The intensity of the $Q_y$ transition can be assessed by the measured molar absorption coefficient; however, comparisons of such values are somewhat unreliable given the experimental variability encountered upon handling small quantities of materials. A better comparison is achieved by examination of the ratio of the intensities of the B and $Q_y$ bands for a given compound (B/$Q_y$ ratio), which is determined simply by absorption spectroscopy without requiring determination of the molar absorption coefficient. For a wide variety of applications, bathochromic and hyperchromic shifts of the $Q_y$ band are desired (i.e., shifted to longer wavelength and intensified), thereby affording strong absorption in the deep-red region.

The spectral properties of the chlorins are listed in Table 1. Appropriate benchmark compounds include the zinc or free base chlorins (11, Zn-11)[16] lacking any 13-substituent (Chart 4), the zinc-chelated analogues of chlorophyll a or b,[33] and chlorophyll a.[34]

Chart 4

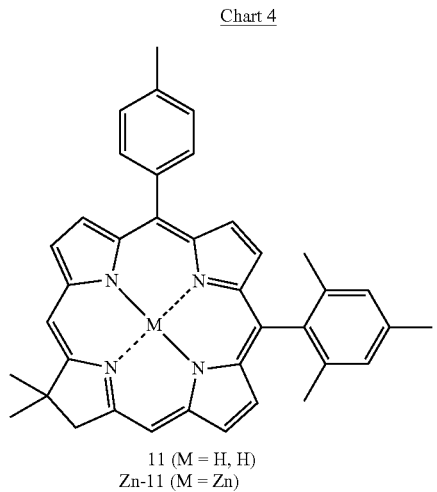

11 (M = H, H)
Zn-11 (M = Zn)

Comparison of the data for Zn-1 and Zn-11 show that introduction of the 13-acetyl substituent redshifts the $Q_y$ band by 27 nm and increases the $Q_y$ band intensity. The latter can be assessed either by comparison of molar absorption coefficients (log $\epsilon$=4.75 vs. 4.64) or by comparison of the B/$Q_y$ band ratios (2.9 vs. 4.2).

The spectra of Zn-1 and Zn-11 are shown in FIG. 1. Similar observations are also found in the corresponding free base chlorins.

The enhancement in intensity and wavelength of the $Q_y$ band in 13-acetylchlorins is explained as follows. The acetyl group at 13-position can adopt a planar conformation and thus conjugate with the π-electrons of the macrocycle. The crystal structure of Cu-1 shows the near co-planarity of the acetyl group with the chlorin macrocycle in the solid state. It has been shown that the acetyl group of 13-acetylporphyrins in an unhindered β-pyrrolic position can adopt a planar conformation and thus conjugate with the π-electron of the macrocycle.[35] However, the carbonyl group is pointed toward the 15-position rather than toward the 12-position (as in chlorophylls). While the presence of the acetyl group in the synthetic 13-acetylchlorins significantly changes the wavelength and intensity of the $Q_y$ band, the absorption properties of Zn-1 do not completely mimic those of chlorophyll. For example, Zn-1 absorbs at 424 and 635 nm whereas chlorophyll a absorbs at 430 and 662 nm. Moreover, the B/$Q_y$ band intensity ratio (2.9) in Zn-1 is much greater than that (1.3) of chlorophyll a. The spectra described above were recorded in solution, where the 13-acetyl group is expected to have considerable conformational freedom of rotation versus that of the carbonyl group in the isocyclic ring of chlorophylls.

TABLE 1

Absorption Properties of Chlorins[a]

| chlorins | $\lambda_{max}$ (nm), B | $\lambda_{max}$ (nm), $Q_y$ | log $\epsilon$ (M$^{-1}$cm$^{-1}$) ($Q_y$ band) | B/$Q_y$ intensity ratio |
|---|---|---|---|---|
| chlorophyll a[b] | 430 | 662 | 4.93 | 1.3 |
| Zn-chlorophyll a[c] | 423 | 653 | — | 1.4 |
| Zn-chlorophyll b[c] | 446 | 634 | — | 2.9 |
| Zn-1 | 424 | 635 | 4.75 | 2.9 |
| Cu-1 | 420 | 631 | 4.69 | 3.1 |
| Zn-11 | 412 | 608 | 4.64 | 4.2 |
| Zn-8 | 414 | 616 | 4.65 | 4.0 |
| pheophytin a[d] | 408 | 667 | 5.12 | 2.1 |
| 1 | 422 | 661 | 4.67 | 2.3 |
| 11 | 414 | 641 | 4.45 | 3.1 |
| 2 | 417 | 660 | — | 2.5 |

[a]In toluene at room temperature unless noted otherwise.
[b]Ref 34 (in diethyl ether).
[c]Ref 33 (in diethyl ether).
[d]Ref 36 (in diethyl ether).

The presence of the isocyclic ring in free base phorbine 2 redshifts the $Q_y$ band by 19 nm and affords a relative increase in intensity of the $Q_y$ band, by comparison with the benchmark chlorin 11. The spectra of 2 and 11 are shown in FIG. 2. The $Q_y$ position of phorbine 2 (660 nm) closely resembles that of pheophytin a (667 nm),[36] the free base analogue of chlorophyll a.

Fluorescence Properties. The free-base 13-acetylchlorin 1 exhibits a strong $Q_y$(0,0) fluorescence band at approximately 668 nm and a weak emission feature with two discernible maxima (~711 and 744 nm). The zinc chelate Zn-1 has a dominant fluorescence band at around 641 nm and a broad weak band in the region 670-720 nm. The fluorescence quantum yield ($\Phi_f$) of free-base chlorin 1 is 0.23, while that of Zn-1 is 0.24. These data are to be compared with those of 2 (0.29) and Zn-11 (0.065).[16]

Conclusions. A new route has been developed for installing the isocyclic ring on tetrapyrrole macrocycles. The route entails preparation of a 13-acetylchlorin, which undergoes bromination at the 15-position followed by a Pd-mediated α-arylation procedure. The α-arylation procedure proceeds under mild conditions. The presence of a keto group at the 13-position significantly redshifts the absorption maximum and affords a relative increase in the intensity of the $Q_y$ band. The ability to install the isocyclic ring opens up a number of possible applications ranging from use in artificial photosynthesis to photomedicine.

Experimental Section

General. $^1$H NMR (400 MHz) and $^{13}$C NMR (75 MHz) spectra were collected at room temperature in CDCl$_3$. Absorption spectra were obtained in toluene at room temperature. Chlorins were analyzed by laser desorption mass spectrometry (LD-MS) in the absence of a matrix. Fast atom bombardment mass spectrometry (FAB-MS) data are reported for the molecule ion or protonated molecule ion. Melting points are uncorrected. All commercially available materials were used as received. All palladium-coupling reactions were carried out using standard Schlenk-line techniques.

The chlorin-forming reaction was performed during a single day starting from the preparation of the 8,9-dibromo-1-formyldipyrromethane. The condensation of an Eastern half and the Western half was carried out at room temperature under argon. The condensation reaction mixture was quenched with ice-cold aqueous NaHCO$_3$. An ice-cold solution of the crude product in CH$_3$CN was treated with 2,2,6,6-tetramethylpiperidine (TMP) followed by Zn(OAc)$_2$ and AgOTf. The reaction mixture was stirred at room temperature for 10-15 min before set it to gentle reflux.

Fluorescence Spectroscopy. The fluorescence spectra and fluorescence quantum yields reported herein were collected in toluene at room temperature. Measurements of fluorescence quantum yield ($\Phi_f$) were carried out using chlorin Zn-11 ($\Phi_f$=0.065) as a standard.[16]

Noncommercial Compounds. Compounds 3,[23] 4,[24] 5,[24] and 7[17] were prepared following literature procedures.

13-Acetyl-17,18-dihydro-10-mesityl-18,18-dimethyl-5-p-tolylporphyrin (1). Following a procedure for Stille coupling on aromatic compounds,[27] a mixture of 8 (75 mg, 0.12 mmol), 9 (80 μL, 0.24 mmol) and (PPh$_3$)$_2$PdCl$_2$ (9.0 mg, 0.013 mmol) was refluxed in THF (12 mL) for 20 h in a Schlenk line. The reaction mixture was treated with 10% aqueous HCl (4 mL) at room temperature for 2 h. CH$_2$Cl$_2$ was added and the organic layer was separated. The organic layer was washed with saturated aqueous NaHCO$_3$, water, and brine. The organic layer was dried (Na$_2$SO$_4$), concentrated and chromatographed [silica, CH$_2$Cl$_2$/hexanes (1:1)], affording a purple solid (50 mg, 71%): $^1$H NMR δ –0.98 (brs, 2H), 1.86 (s, 6H), 2.02 (s, 6H), 2.61 (s, 3H), 2.66 (s, 3H), 3.05 (s, 3H), 4.56 (s, 2H), 7.24 (s, 2H), 7.50 (d, J=7.8 Hz, 2H), 7.96 (d, J=7.8 Hz, 2H), 8.23 (d, J=4.4 Hz, 1H), 8.31 (d, J=4.4 Hz, 1H), 8.68 (d, J=4.4 Hz, 1H), 8.69 (s, 1H), 8.70 (d, J=4.4 Hz, 1H), 8.86 (s, 1H), 9.98 (s, 1H); LD-MS obsd 590.8; FAB-MS obsd 590.3052, calcd 590.3046 (C$_{40}$H$_{38}$N$_4$O); $\lambda_{abs}$ 422, 661 (log ε=4.67) nm, $\lambda_{em}$ 668, 711, 714 nm ($\Phi_f$=0.23).

Zn(II)-13-Acetyl-17,18-dihydro-10-mesityl-18,18-dimethyl-5-p-tolylporphyrin (Zn-1). A solution of 1 (20 mg, 0.034 mmol) in CHCl$_3$ (2.8 mL) was treated with a solution of Zn(OAc)$_2 \cdot$2H$_2$O (75 mg, 0.34 mmol) in methanol (0.7 mL). The reaction mixture was stirred at room temperature for 16 h. CH$_2$Cl$_2$ was added and the reaction mixture was washed with water and brine. The organic layer was dried (Na$_2$SO$_4$). The crude mixture was concentrated and chromatographed (silica, CH$_2$Cl$_2$), affording a green solid (18 mg, 81%): $^1$H NMR δ 1.84 (s, 6H), 1.98 (s, 6H), 2.58 (s, 3H), 2.64 (s, 3H), 2.87 (s, 3H), 4.46 (s, 2H), 7.20 (s, 2H), 7.46 (d, J=8.2 Hz, 2H), 7.89 (d, J=8.2 Hz, 2H), 8.16 (d, J=4.4 Hz, 1H), 8.24 (d, J=4.4 Hz, 1H), 8.44 (s, 1H), 8.57 (d, J=4.4 Hz, 1H), 8.58 (d, J=4.4 Hz, 1H), 8.81 (s, 1H), 9.64 (s, 1H); LD-MS obsd 654.5; FAB-MS obsd 652.2238, calcd 652.2181 (C$_{40}$H$_{36}$N$_4$OZn); $\lambda_{abs}$ 424, 635 (log ε=4.75) nm, $\lambda_{em}$ 641, 670-720 nm ($\Phi_f$=0.24).

Cu(II)-13-Acetyl-17,18-dihydro-10-mesityl-18,18-dimethyl-5-p-tolylporphyrin (Cu-1). A solution of 1 (19 mg, 0.032 mmol) in CHCl$_3$ (3.2 mL) was treated with a solution of Cu(OAc)$_2 \cdot$H$_2$O (65 mg, 0.32 mmol) in methanol (0.8 mL) at room temperature for 16 h. The reaction mixture was washed with water and brine. The organic layer was dried (Na$_2$SO$_4$), concentrated and chromatographed [silica, CH$_2$Cl$_2$/hexanes (1:1)], affording a purple solid (17 mg, 81%): LD-MS obsd 651.7; FAB-MS obsd 651.2235, calcd 651.2285 (C$_{40}$H$_{36}$N$_4$OCu); $\lambda_{abs}$ 420, 631 (log ε=4.69) nm.

18,18-Dimethyl-10-mesityl-13$^1$-oxo-5-p-tolylphorbine (2). Following a procedure for α-arylation of aliphatic ketones,[28] a solution of 1 (18 mg, 0.030 mmol) in THF (15 mL) was treated with NBS (5.5 mg, 0.030 mmol) at room temperature for 2 h. CH$_2$Cl$_2$ was added. The mixture was washed with aqueous NaHCO$_3$. The organic layer was dried (Na$_2$SO$_4$) and concentrated. The crude mixture was used in the next step. Thus, a mixture of the crude solid, Cs$_2$CO$_3$ (50 mg, 0.15 mmol), and (PPh$_3$)$_2$PdCl$_2$ (4.0 mg, 6.0 μmol) was refluxed in THF (2 mL) for 20 h in a Schlenk line. CH$_2$Cl$_2$ was added. The reaction mixture was washed with water and brine. The organic layer was dried (Na$_2$SO$_4$), concentrated and chromatographed [silica, CH$_2$Cl$_2$/hexanes (3:1)], affording a purple solid (8.0 mg, 44%): $^1$H NMR δ –1.25 (brs, 2H), 1.88 (s, 6H), 2.02 (s, 6H), 2.57 (s, 3H), 2.65 (s, 3H), 4.27 (s, 2H), 5.12 (s, 2H), 7.20 (s, 2H), 7.49 (d, J=7.8 Hz, 2H), 7.93 (d, J=7.8 Hz, 2H), 8.22 (d, J=4.4 Hz, 1H), 8.28 (d, J=4.4 Hz, 1H), 8.53 (s, 1H), 8.58 (s, 1H), 8.62 (d, J=4.4 Hz, 1H), 8.70 (d, J=4.4 Hz, 1H); LD-MS obsd 588.3; FAB-MS obsd 588.2900, calcd 588.2889 (C$_{40}$H$_{36}$N$_4$O); $\lambda_{abs}$ 417, 430, 529, 561, 660 nm.

5-Mesityl-1-(4-methylbenzoyl)dipyrromethane (5). Following a reported procedure,[24] a solution of EtMgBr (30.0 mL, 30.0 mmol, 1.0 M solution in THF) was added dropwise to a solution of 3 (2.64 g, 10.0 mmol) in dry THF (50 mL) over a 5 min period. The solution was stirred at room temperature for 30 min. The solution was cooled to –78° C. and then a solution of 4 (2.75 g, 12.0 mmol) in dry THF (20 mL) was added dropwise. The mixture was stirred for 3 h at –78° C. Saturated aqueous NH$_4$Cl was added. The mixture was extracted with CH$_2$Cl$_2$. The organic phase was dried (Na$_2$SO$_4$), concentrated and chromatographed [silica, hexanes/CH$_2$Cl$_2$/ethyl acetate (7:2:1)], affording a pale yellow solid (2.80 g, 73%): mp 74-75° C. [lit.[13] 75-77° C.]; $^1$H NMR δ 2.10 (s, 6H), 2.30 (s, 3H), 2.43 (s, 3H), 5.96 (s, 1H), 6.12 (m, 2H), 6.22 (m, 1H), 6.68 (s, 1H), 6.83 (m, 1H), 6.90 (s, 2H), 7.26 (d, J=7.5 Hz, 2H), 7.77 (d, J=7.5 Hz, 2H), 7.85 (brs, 1H), 9.23 (brs, 1H); $^{13}$C NMR δ 20.6, 20.7, 21.5, 38.6, 107.1, 108.9, 109.9, 116.8, 120.1, 128.9, 129.1, 129.9, 130.5, 133.1, 135.7, 137.2, 137.4, 140.4, 142.1, 183.9; Anal. Calcd for C$_{26}$H$_{26}$N$_2$O: C, 81.64; H, 6.85; N, 7.32. Found: C, 81.49; H, 7.01; N, 7.01.

Note: Some amount (~10%) of the starting 5-mesityldipyrromethane was recovered in this reaction.

10-(Dibutylboryl)-5-mesityl-1-p-toluoyldipyrromethane (Bu$_2$B-5). Following a general procedure,[25] a solution of 5 (230 mg, 0.600 mmol) in CH$_2$Cl$_2$ (3.2 mL) was treated with TEA (0.200 mL, 1.44 mmol) followed by Bu$_2$BOTf (1.20 mL, 1.20 mmol) in hexanes. After 2 h, the mixture was passed through a pad of silica (2×8 cm) eluting with CH$_2$Cl$_2$. The fast moving yellow fractions were collected and concentrated, affording an orange oil (300 mg, 98%): $^1$H NMR δ 0.36-0.52 (m, 2H), 0.61 (t, J=7.2 Hz, 3H), 0.78 (t, J=7.2 Hz, 3H), 0.82-0.98 (m, 4H), 1.16-1.22 (m, 6H), 2.18 (s, 6H), 2.26 (s, 3H), 2.47 (s, 3H), 5.86 (s, 1H), 5.88 (m, 1H), 6.19 (m, 1H), 6.42 (d, J=4.1 Hz, 1H), 6.83 (m, 1H), 6.91 (s, 2H), 7.19 (d, J=4.1 Hz, 1H), 7.37 (d, J=8.1 Hz, 2H), 7.82 (br s, 1H), 8.10 (d, J=8.1 Hz, 2H); $^{13}$C NMR δ 14.3, 14.5, 20.9, 21.7, 22.1, 26.1, 26.3, 27.3, 27.5, 40.0, 107.9, 108.8, 116.7, 122.0, 128.1, 129.9, 130.0, 130.4, 130.6, 135.2, 136.8, 137.3, 145.2, 151.5, 176.0; Anal. Calcd for C$_{34}$H$_{43}$BN$_2$O: C, 80.62; H, 8.56; N, 8.56. Found: C, 81.22; H, 9.83; N, 8.54. FAB-MS obsd 506.3458, calcd 506.3468 (C$_{34}$H$_{43}$BrN$_2$O).

Note: Compound Bu$_2$B-5 decomposes partially at room temperature.

8,9-Dibromo-5-mesityl-1-(4-methylbenzoyl)dipyrromethane (6). Following a procedure for 8,9-dibromination of 1-acyldipyrromethanes,[22] a solution of 5 (573 mg, 1.50 mmol) in dry THF (15 mL) at –78° C. under argon was treated portionwise with NBS (587 mg, 3.30 mmol). The reaction mixture was stirred for 1 h at –78° C. Hexanes was added to the reaction mixture at –20° C. The reaction mixture was then allowed to warm to 0° C. The organic layer was washed with ice-cold water, dried (K$_2$CO$_3$) and concentrated without heating in a water-bath at ambient temperature. The resulting brown solid was purified by column chromatography [silica, hexanes/CH$_2$Cl$_2$/ethyl acetate (7:2:1)], affording a yellow solid (0.465 g, 57%): mp 120-122° C. (dec); $^1$H NMR δ 2.08 (s, 6H), 2.30 (s, 3H), 2.42 (s, 3H), 5.81 (s, 1H), 6.05 (d, J=3.3 Hz, 1H), 6.12 (dd, J=4.2, 3.3 Hz, 1H), 6.80 (dd, J=4.2, 3.3 Hz, 1H), 6.90 (s, 2H), 7.26 (d, J=8.1 Hz, 2H), 7.74 (d, J=8.1 Hz, 2H), 8.07 (brs, 1H), 9.10 (brs, 1H); $^{13}$C NMR δ 20.3, 21.0, 21.8, 39.0, 98.7, 99.2, 110.4, 111.4, 120.2, 29.2, 130.6, 131.0, 131.7, 131.8, 135.7, 137.6, 138.0, 139.0, 142.7, 184.2; FAB-MS obsd 538.0240, calcd 538.0255 ($C_{26}H_{24}Br_2N_2O$).

Notes: (1) The use of ethyl acetate or any chlorinated solvent should be avoided during workup. All of the workup operations including solvent removal should be done without heating, and preferably under chilled conditions.

(2) The crude mixture is poorly soluble in hexanes/$CH_2Cl_2$/ethyl acetate (7:2:1), a recommended solvent for column chromatography. Therefore, a minimum amount of THF can be employed along with the above solvent mixture before loading on the column.

(3) Isolated pure 6 is labile. Careful handling of the solution of compound 6 is required. Compound 6 decomposes almost completely in solution (such as in ethyl acetate or chlorinated solvent) within 8-10 h even at 0° C. The powdered solid 6 can be stored at −10° C. for 1-2 days without decomposition. Compound 6 decomposed several times during NMR measurements (regardless of solvent such as $CDCl_3$, $C_6D_6$ or THF-$d_8$) or attempted crystallization.

8,9-Dibromo-10-(dibutylboryl)-5-mesityl-1-p-toluoyl-dipyrromethane ($Bu_2B$-6). A solution of 5-$Bu_2B$ (200 mg, 0.400 mmol) in dry THF (4 mL) was treated with NBS (156 mg, 0.880 mmol) at −78° C. The reaction mixture was stirred for 1 h at −78° C. Hexanes and water were added to the reaction mixture at −20° C. The organic layer was dried ($Na_2SO_4$) and the solvent was removed without heat. The crude mixture was concentrated and chromatographed [silica, hexanes/toluene (1:1)], affording a brown solid (80 mg, 30%): mp 55° C. (dec); $^1$H NMR δ 0.20-0.42 (m, 2H), 0.58 (t, J=7.2 Hz, 3H), 0.78 (t, J=7.2 Hz, 3H), 0.82-0.98 (m, 4H), 1.16-1.22 (m, 6H), 2.15 (s, 6H), 2.27 (s, 3H), 2.47 (s, 3H), 5.80 (s, 1H), 5.89 (m, 1H), 6.46 (d, J=4.1 Hz, 1H), 6.84 (s, 2H), 7.20 (d, J=4.1 Hz, 1H), 7.35 (d, J=8.1 Hz, 2H), 7.81 (brs, 1H), 8.10 (d, J=8.1 Hz, 2H); $^{13}$C NMR δ 14.3, 14.5, 20.9, 21.3, 21.7, 22.2, 26.1, 26.2, 26.3, 27.2, 27.6, 40.1, 98.1, 99.2, 111.9, 116.8, 121.3, 127.9, 130.0, 130.1, 130.8, 132.7, 133.4, 135.4, 137.3, 137.4, 145.6, 149.1, 176.7; FAB-MS obsd 662.1668, calcd 662.1679 ($C_{34}H_{41}BBr_2N_2O$).

Note: The stability of $Bu_2B$-6 is similar to that of compound 6. All the points noted above for compound 6 are equally applicable for $Bu_2B$-6.

13-Bromo-17,18-dihydro-10-mesityl-18,18-dimethyl-5-p-tolylporphyrin (8). A solution of Zn-8 (97 mg, 0.14 mmol) in $CH_2Cl_2$ (2 mL) was treated dropwise with TFA (0.20 mL, 2.6 mmol) over a 10 min period. The solution was stirred at room temperature for 2 h. $CH_2Cl_2$ was added and the organic layer was washed (saturated aqueous $NaHCO_3$, water, and brine) and then dried ($Na_2SO_4$). The crude mixture was concentrated and chromatographed [silica, hexanes/$CH_2Cl_2$ (2:1)], affording a purple solid (75 mg, 85%): $^1$H NMR δ −1.70 (brs, 2H), 1.85 (s, 6H), 2.05 (s, 6H), 2.60 (s, 3H), 2.67 (s, 3H), 4.62 (s, 2H), 7.23 (s, 2H), 7.50 (d, J=8.1 Hz, 2H), 7.99 (d, J=8.1 Hz, 2H), 8.30 (d, J=4.8 Hz, 1H), 8.43 (d, J=4.4 Hz, 1H), 8.60 (s, 1H), 8.76 (d, J=4.8 Hz, 1H); 8.80 (d, J=4.4 Hz, 1H), 8.84 (s, 1H), 9.03 (s, 1H); LD-MS obsd 626.8; FAB-MS obsd 626.2053, calcd 626.2045 ($C_{38}H_{35}N_4Br$); $\lambda_{abs}$ 416, 647 nm.

Zn(II)-13-Bromo-17,18-dihydro-10-mesityl-18,18-dimethyl-5-p-tolylporphyrin (Zn-8). Following a reported procedure,[17] a solution of 6 (465 mg, 0.860 mmol) in THF/MeOH (4:1, 45 mL) was treated portionwise with a sample of $NaBH_4$ (325 mg, 8.60 mmol) at 0° C. and the reaction mixture was stirred at room temperature for 3 h under argon. Saturated aqueous $NH_4Cl$ was added at 0° C. The mixture was extracted with ethyl acetate (ice-cold). The combined organic extracts were dried ($K_2CO_3$) and concentrated under reduced pressure without heating. The crude mixture was placed on a vacuum line for a few minutes to remove residual solvent, affording a yellow foam-like solid. The resulting solid was dissolved in anhydrous $CH_3CN$ (8.6 mL) at 0° C. Western half 7 (164 mg, 0.860 mmol) was added followed by dropwise addition of TFA (64 μL, 0.83 mmol). The reaction mixture was stirred at room temperature under argon for 30 min. The reaction mixture was diluted with $CH_3CN$ (77 mL) at 0° C. 2,2,6,6-Tetramethylpiperidine (1.52 mL, 9.00 mmol) was added and the reaction mixture was stirred at 0° C. for 5-10 min. $Zn(OAc)_2$ (1.10 g, 6.00 mmol) was added followed by AgOTf (464 mg, 1.80 mmol). The resulting suspension was refluxed for 18 h exposed to air. The crude mixture was concentrated and chromatographed [silica, hexanes/$CH_2Cl_2$ (2:1)], affording a green solid (83 mg, 14%): $^1$H NMR δ 1.86 (s, 6H), 2.02 (s, 6H), 2.58 (s, 3H), 2.66 (s, 3H), 4.53 (s, 2H), 7.21 (s, 2H), 7.48 (d, J=8.1 Hz, 2H), 7.94 (d, J=8.1 Hz, 2H), 8.22 (d, J=4.8 Hz, 1H), 8.35 (d, J=4.4 Hz, 1H), 8.50 (s, 1H), 8.56 (s, 1H), 8.64 (d, J=4.8 Hz, 1H), 8.66 (d, J=4.4 Hz, 1H), 8.79 (s, 1H); LD-MS obsd 691.7; FAB-MS obsd 688.1178, calcd 688.1180 ($C_{38}H_{33}BrN_4Zn$); $\lambda_{abs}$ 414, 616 nm.

Notes: (1) The completion of reduction can be monitored by TLC analysis (hexanes/ethyl acetate, 3:1). On some occasions, reduction of 6 using 10 equiv of $NaBH_4$ is not complete in 3 h. In that case, it is necessary to add more (5 equiv) $NaBH_4$ in the reaction mixture or stir the reaction mixture for a prolonged period. The use of chlorinated solvents should be avoided during workup. All of the operations including solvent removal should be done without heating and preferably under chilled conditions. The resulting dipyrromethane-1-carbinol changes color from yellow to reddish during removal of the residual solvent.

(2) During the tetrahydrobilene a formation, all operations (such as addition of Western half or TFA) should be done as quickly as possible. After 30 min, the color of the reaction mixture changed from yellow to reddish brown.

(3) After the reaction forming the tetrahydrobilene a, the slow addition of 2,2,6,6-tetramethylpiperidine in the reaction mixture at 0° C. is necessary.

15-Bromo-17,18-dihydro-10-mesityl-18,18-dimethyl-5-p-tolylporphyrin (10). Following a reported procedure,[21] a solution of 1 (18.0 mg, 0.030 mmol) in THF (15 mL) was treated with NBS (5.5 mg, 0.030 mmol) at room temperature for 2 h. $CH_2Cl_2$ was added. The mixture was washed with aqueous $NaHCO_3$. The organic layer was dried ($Na_2SO_4$), concentrated, and chromatographed [silica, $CH_2Cl_2$/hexanes (3:1)], affording a purple solid (15 mg, 73%): $^1$H NMR δ −0.68-0.78 (br, 1H), 0.98-1.02 (br, 1H), 1.86 (s, 6H), 2.04 (s, 6H), 2.60 (s, 3H), 2.66 (s, 3H), 3.06 (s, 3H), 4.55 (s, 2H), 7.21 (s, 2H), 7.51 (d, J=7.8 Hz, 2H), 7.96 (d, J=7.8 Hz, 2H), 8.26 (d, J=4.4 Hz, 1H), 8.34 (d, J=4.4 Hz, 1H), 8.45 (s, 1H), 8.70-8.76 (m, 3H); FAB-MS obsd 668.2145, calcd 668.2150 ($C_{40}H_{37}BrN_4O$); $\lambda_{abs}$ 414, 515, 546, 600, 652 nm.

References (1) Scheer, H. In *Chlorophylls*; Scheer, H. Ed.; CRC Press, Inc.: Boca Raton, Fla., USA, 1991; pp 3-30.

(2) Boldt, N. J.; Donohoe, R. J.; Birge, R. R.; Bocian, D. F. *J. Am. Chem. Soc.* 1987, 109, 2284-2298.

(3) Linke-Schaetzel, M.; Bhise, A. D.; Gliemann, H.; Koch, T.; Schimmel, T.; Balaban, T. S. *Thin Solid Films* 2004, 451, 16-21.

(4) Licha, K. *Top. Curr. Chem.* 2002, 222, 1-29.

(5) Pandey, R. K.; Zheng, G. In *The Porphyrin Handbook*; Kadish, K. M.; Smith, K. M.; Guilard, R., Eds.; Academic Press: San Diego, 2000; Vol. 6, pp. 157-230.

(6) Pavlov, V. Y.; Ponomarev, G. V. *Chemistry of Heterocyclic Compounds* 2004, 40, 393-425.
(7) Fischer, H.; Laubereau, O. *Justus Liebigs Ann. Chem.* 1938, 535, 17-37.
(8) Fischer, H.; Lautsch, W. *Justus Liebigs Ann. Chem.* 1937, 528, 265-275.
(9) Fischer, H.; Oestreicher, A. *Justus Liebigs Ann. Chem.* 1941, 546, 49-59.
(10) (a) Smith, K. M.; Bisset, G. M. F.; Bushell, M. J. *Bioorg. Chem.* 1980, 9, 1-26. (b) Smith, K. M.; Bushell, M. J.; Rimmer, J.; Unsworth, J. F. *J. Am. Chem. Soc.* 1980, 102, 2437-2448. (c) Smith, K. M.; Bisset, G. M. F.; Bushell, M. J. *J. Org. Chem.* 1980, 45, 2218-2224.
(11) Gerlach, B.; Brantley, S.; Smith, K. M. *J. Org. Chem.* 1998, 63, 2314-2320.
(12) Pallenberg, A. J.; Dobhal, M. P.; Pandey, R. K. *Org. Process Res. Dev.* 2004, 8, 287-290.
(13) (a) Cox, M. T.; Howarth, T. T.; Jackson, A. H.; Kenner, G. W. *J. Am. Chem. Soc.* 1969, 91, 1232-1233. (b) Kenner, G. W.; McCombie, S. W.; Smith, K. M. *J. Chem. Soc. Chem. Comm.* 1972, 844-845. (c) Cox, M. T.; Howarth, T. T.; Jackson, A. H.; Kenner, G. W. *J. Chem. Soc. Perkin Trans. I* 1974, 512-516. (d) Kenner, G. W.; McCombie, S. W.; Smith, K. M. *J. Chem. Soc. Perkin Trans. I* 1974, 527-530.
(14) Smith, K. M.; Lewis, W. M. *Tetrahedron* 1981, 37 Supp. 1, 399-403.
(15) (a) Flaugh, M. E.; Rapoport, H. *J. Am. Chem. Soc.* 1968, 90, 6877-6879. (b) Li, W.; Lash, T. D. *Tetrahedron Lett.* 1998, 39, 8571-8574. (c) Lash, T. D.; Catarello, J. J. *Tetrahedron* 1993, 49, 4159-4172.
(16) Strachan, J.-P.; O'Shea, D. F.; Balasubramanian, T.; Lindsey, J. S. *J. Org. Chem.* 2000, 65, 3160-3172.
(17) Taniguchi, M.; Ra, D.; Mo, G.; Balasubramanian, T.; Lindsey, J. S. *J. Org. Chem.* 2001, 66, 7342-7354.
(18) Ptaszek, M.; McDowell, B. E.; Taniguchi, M.; Kim, H.-J.; Boyle, P. D.; Lindsey, J. S. (1-Formyldipyrromethanes can be prepared from a dipyrromethane by statistical Vilsmeier formylation followed by selective removal of the unwanted 1,9-diformyldipyrromethane by dialkyltin complexation. The 1-formyldipyrromethane can be brominated with NBS in the standard way to give the 1-formyl-9-bromodipyrromethane, which serves as an Eastern half in chlorin formation. The 1-formyl-9-bromodipyrromethane undergoes condensation with a Western half upon treatment with an acid catalyst such as p-toluenesulfonic acid. The metal-mediated oxidative cyclization then proceeds in the standard way to give the corresponding 5-unsubstituted chlorin.)
(19) Balasubramanian, T.; Strachan, J. P.; Boyle, P. D.; Lindsey, J. S. *J. Org. Chem.* 2000, 65, 7919-7929.
(20) Taniguchi, M.; Kim, H.-J.; Ra, D.; Schwartz, J. K.; Kirmaier, C.; Hindin, E.; Diers, J. R.; Prathapan, S.; Bocian, D. F.; Holten, D.; Lindsey, J. S. *J. Org. Chem.* 2002, 67, 7329-7342
(21) Taniguchi, M.; Kim, M. N.; Ra, D.; Lindsey, J. S. *J. Org. Chem.* 2005, 70, 275-285.
(22) See Example 2 below.
(23) Laha, J. K.; Dhanalekshmi, S.; Taniguchi, M.; Ambroise, A.; Lindsey, J. S. *Org. Process Res. Dev.* 2003, 7, 799-812.
(24) Rao, P. D.; Littler, B. J.; Geier, G. R., III; Lindsey, J. S. *J. Org. Chem.* 2000, 65, 1084-1092.
(25) Muthukumaran, K.; Ptaszek, M.; Noll, B.; Scheidt, W. R.; Lindsey, J. S. *J. Org. Chem.* 2004, 69, 5354-5364.
(26) (a) Bailey, D. M.; Johnson, R. E. *J. Med. Chem.* 1973, 16, 1300-1302. (b) Bailey, D. M.; Johnson, R. E.; Salvador, U. J. *J. Med. Chem.* 1973, 16, 1298-1300. (c) Gilow, H. M.; Burton, D. E. *J. Org. Chem.* 1981, 46, 2221-2225. (d) Keifer, P. A.; Schwartz, R. E.; Koker, M. E. S.; Hughes, R. G. Jr.; Rittschof, D.; Rinehart, K. L. *J. Org. Chem.* 1991, 56, 2965-2975. (e) Matsuki, S.; Mizuno, A.; Annoura, H.; Tatsuoka, T. *J. Heterocyclic Chem.* 1997, 34, 87-91. (f) Olofson, A.; Yakushijin, K.; Horne, D. A. *J. Org. Chem.* 1998, 63, 1248-2225. (g) He, R. H.-Y.; Jiang, X.-K. *J. Chem. Research (S)* 1998, 786-787. (h) Armitt, D. J.; Banwell, M. G.; Freeman, C.; Parish, C. R. *J. Chem. Soc., Perkin Trans. 1*, 2002, 1743-1745. (i) Hoffmann, H.; Lindel, T. *Synthesis* 2003, 1753-1783. (j) Patel, J.; Pelloux-Leon, N.; Minassian, F.; Vallee, Y. *J. Org. Chem.* 2005, 70, 9081-9084.
(27) Kosugi, M.; Sumiya, T.; Obara, Y.; Suzuki, M.; Sano, H.; Migita, T. *Bull. Chem. Soc. Jpn.* 1987, 60, 767-768.
(28) (a) Muratake, H.; Natsume, M. *Tetrahedron Lett.* 1997, 38, 7581-7582. (b) Muratake, H.; Natsume, M.; Nakai, H. *Tetrahedron* 2004, 60, 11783-11803.
(29) Smith, K. M.; Langry, K. C.; Minnetian, O. M. *J. Org. Chem.* 1984, 49, 4602-4609.
(30) Moss, G. P. *Pure Appl. Chem.* 1987, 59, 779-832.
(31) Loader, C. E.; Anderson, H. J. *Tetrahedron* 1969, 25, 3879-3885.
(32) Katz, J. J.; Dougherty, R. C.; Boucher, L. J. in *The Chlorophylls*, Vernon, L. P.; Seely, G. R., Eds., Academic Press: New York, 1966, pp 185-251.
(33) Jones, I. D.; White, R. C.; Gibbs, E.; Denard, C. D. *J. Agric. Food Chem.* 1968, 16, 80-83.
(34) Strain, H. H.; Svec, W. A. in *The Chlorophylls*, Vernon, L. P.; Seely, G. R., Eds., Academic Press: New York, 1966, pp 21-66.
(35) Balaban, T. S.; Linke-Schaetzel, M.; Bhise, A. D.; Vanthuyne, N.; Roussel, C. *Eur. J. Org. Chem.* 2004, 3919-3930.
(36) Smith, J. H. C.; Benitez, A. In *Modern Methods of Plant Analysis*; Paech, K., Tracey, M. V., Eds.; Springer-Verlag: Berlin, 1955; Vol. IV, pp 142-196.

Example 2

Synthesis of Chlorins Bearing Conjugative Substituents at the 3 and/or 13-Positions The fundamental chromophore of the chlorophylls is a chlorin, which differs from a porphyrin in having one pyrrole ring reduced at the I-positions. Reduction of a porphyrin to give the chlorin enhances the intensity of the long-wavelength absorption ($Q_y$) band. However, mere reduction does not account for the strong intensity or redshifted position of the long-wavelength transition exhibited by naturally occurring chlorophylls. Indeed, chlorophyll a exhibits a strong $Q_y$ band at 662 nm ($\epsilon_{Qy}$=86,300 $M^{-1}cm^{-1}$), and chlorophyll b exhibits a $Q_y$ band at 642 nm ($\epsilon_{Qy}$=56,100 $M^{-1}cm^{-1}$).[1] (FIG. 3) By contrast, a benchmark compound that contains only the core magnesium chlorin chromophore exhibits a $Q_y$ band at 610 nm ($\epsilon_{Qy}$=56,000 $M^{-1}cm^{-1}$)[2]. Naturally occurring chlorins typically contain a full complement of substituents at the β-pyrrole positions about the perimeter of the macrocycle, including alkyl groups (2-, 8-, and 12-positions) and auxochromic groups (3-, 7-, and 13-positions). Chlorophyll a and b each bear a 3-vinyl group, an isocyclic ring spanning the 13-15 positions, and a 7-methyl or 7-formyl group, respectively.[3] The isocyclic ring contains a $13^1$-oxo group, which is conjugated with the π-system of the macrocycle.

Studies to probe the effects of substituents on the spectral properties of chlorophylls have generally relied on the preparation of derivatives of the naturally occurring macrocycles. Such studies indicate that the 3-vinyl substituent redshifts the $Q_y$ transition by ~12-14 nm (versus that of a 3-ethyl group),[4,5] and the annulated 13-keto substituent imparts a redshift of ~20-30 nm.[4,6,7] The 3-vinyl group does not appear to cause any change in the intensity of the transition, whereas the 13-keto substituent has a significant hyperchromic effect.[4] Thus, the presence of conjugative substituents is essential for realizing strong absorption in the far-red region with chlorin chromophores.

Over the past decade we have been developing rational routes for preparing chlorins, wherein each chlorin bears a geminal dimethyl group in the reduced, pyrroline ring to lock-in the chlorin (i.e., dihydroporphyrin) hydrogenation level. The ability to construct regiospecifically substituted chlorins from simple precursors should facilitate fundamental studies of the effects of substituents on spectral properties, thereby complementing studies that employ modification of naturally occurring tetrapyrrole macrocycles.[8] The general synthetic route entails reaction of a 1-bromo-dipyrromethane-9-carbinol (Eastern half) and a 2,3-dihydro-1,3,3-trimethyldipyrrin or 2,3,4,5-tetrahydro-1,3,3-trimethyldipyrrin (Western half). Use of substituted analogues of the Eastern and Western halves provided access to chlorins bearing substituents at the 2, 5, 8, 10, 12, and 18-positions (Chart 1).[9-11] Subsequent oxidation afforded the 17-oxochlorins.[12] Halogenation of the chlorin or oxochlorin at the 15- or 20-position followed by Pd-mediated coupling reactions enabled introduction of aryl or ethynyl substituents at these meso sites.[13] Thus, access has been in hand for all sites with the exception of positions 3, 7, and 13. It is ironic that these latter three sites are perhaps the most important for tuning the spectral properties of the chlorins.

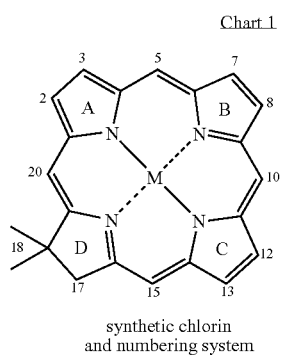

Chart 1 synthetic chlorin
and numbering system

In this example, we report the synthesis of eight chlorins bearing a variety of groups at the 3- and/or 13-positions (Chart 2). The substituents of particular interest are potential auxochromic groups (vinyl, ethynyl, and acetyl). The chlorins bear a minimum of other substituents so that the effects of the 3- and 13-groups can be clearly delineated. The synthetic work reported herein exploits a new route to chlorins (described in the companion paper),[14] which entails reaction of a 1-formyl-9-bromodipyrromethane (Eastern half) and a 2,3,4,5-tetrahydro-1,3,3-trimethyldipyrrin (Western half). Taken together, this work provides the foundation for tuning the spectral properties of chlorins in a systematic manner, and provides access to chlorins of potential value in applications ranging from artificial photosynthesis to photomedicine.

Chart 2

| | $R^3$ | $R^{13}$ |
|---|---|---|
| ZnC-V³M¹⁰ | vinyl | H |
| ZnC-E³M¹⁰ | ≡—TIPS | H |
| ZnC-M¹⁰A¹³ | H | COCH₃ |
| ZnC-M¹⁰E¹³ | H | ≡—TIPS |
| ZnC-E³M¹⁰E¹³ | ≡—TIPS | ≡—TIPS |
| ZnC-E³M¹⁰A¹³ | ≡—TIPS | COCH₃ |

| | $R^3$ | $R^{13}$ |
|---|---|---|
| ZnC-E³E¹³ | ≡—TIPS | ≡—TIPS |
| ZnC-E³A¹³ | ≡—TIPS | COCH₃ |

Results and Discussion

I. Synthesis. Our prior synthetic routes to chlorins employed a 1-bromodipyrromethane-9-carbinol as the Eastern half, where the substituent at the 9-position of the Eastern half became the 5-substituent in the chlorin. The reactivity of the Eastern half mandated the presence of an aryl group at the carbinol position; hence, all chlorins prepared in this manner incorporated a 5-aryl substituent. The methodology for chlorin synthesis in the companion paper entails reaction of a 1-formyl-9-bromodipyrromethane (Eastern half) and a 2,3,4,5-tetrahydro-1,3,3-trimethyldipyrrin (Western half), whereupon the chlorin lacks a 5-substituent. Our general strategy was to exploit this approach to chlorins, using an 8-bromo derivative of the Eastern half (i.e., an 8,9-dibromo-1-formyl-dipyrromethane) and an 8-bromo derivative of the Western half to gain access to chlorins bearing substituents at the 3- and/or 13-positions.

A. Eastern and Western Halves. The syntheses of 8,9-dibromo derivatives of 1-formyldipyrromethanes are shown in Scheme 1. While the 9-bromo derivatives of 1-formyldipyrromethanes are known,[14] 8,9-dibromo derivatives of 1-formyldipyrromethanes have not been previously prepared. In this regard, a number of polyhalogenated pyrroles from marine organisms have been identified and synthesized.[15] Treatment of 1-formyldipyrromethane 1[16] or 2[16] with 2 molar equivalents of NBS at −78° C. gave the 8,9-dibromo derivative 3 or 5 in 56% or 51% yield, respectively. The regiochemistry of the 8,9-vicinal substitution pattern in the dibromo derivatives was established by $^1$H-$^1$H 2D-COSY and 1D-NOE experiments. The regioselective formation of the dibromoproduct (3, 5) can be explained by the fact that the α-acyl-substituted pyrrole ring is deactivated. Therefore, the first bromination occurs at the α-position of the adjacent pyrrole ring, and the second bromination occurs at the vicinal β-pyrrole position.

Scheme 1

| | $R^1$ | $R^2$ | X | Y | Yield |
|---|---|---|---|---|---|
| 3 | H | H | Br | Br | 56% |
| 4 | Mes | H | Br | H | 67% (ref. 14) |
| 5 | Mes | H | Br | Br | 51% |

The synthesis of an 8-bromo-substituted Western half is shown in Scheme 2. Treatment of pyrrole-2-carboxaldehyde with one molar equivalent of NBS at −78° C. gave 4-bromopyrrole-2-carboxaldehyde 6[17] in 55% yield after crystallization. This method of bromination of pyrrole-2-carboxaldehyde is superior to a reported method that uses $Br_2$.[17] It should be mentioned here that careful handing of the crude product is required: the off-white solid often turns reddish (irrespective of preparation using $Br_2$ or NBS), which complicates crystallization. Following a procedure for the synthesis of 2-(2-nitroethyl)pyrroles,[10] treatment of 6 with excess nitromethane, sodium acetate and methylamine hydrochloride at room temperature for 16 h followed by reduction of the reaction mixture with $NaBH_4$ gave 4-bromo-2-(2-nitroethyl)pyrrole (7) in variable yields (32-48%). However, 7 was found to explode (CAUTION), which caused us to avoid handling this compound. Thus, we considered protection of the pyrrole nitrogen in 4-bromo-pyrrole-2-carboxaldehyde (6) for two purposes: (1) to render 4-bromo-2-(2-nitroethyl) pyrrole (7) as a stable compound, and (2) for efficient palladium-coupling in the latter part of the 8-ethynyl Western half synthesis. Considering the facile conditions for removal of a p-toluenesulfonyl group coupled with the crystalline nature of 2-(2-nitroethyl)-N-p-tosylpyrroles, N-tosylation[18] of compound 6 was carried out. Thus, treatment of 6 with NaH at 0° C. for 1 h followed by quenching with p-toluenesulfonyl chloride gave 6-Ts as a pale yellow crystalline solid in 68% yield. Following a reported procedure for the synthesis of 2-(2-nitrovinyl)-N-p-tosylpyrroles,[19] a mixture of 6-Ts, excess nitromethane and ammonium acetate was refluxed for 3 h. The crude product was satisfactorily pure as evidenced by NMR spectroscopy and was directly used in the next step. $NaBH_4$ reduction of the crude product in the presence of Montmorillonite K10[20] or silica gel[21] at room temperature afforded 2-(2-nitroethyl)-N-p-tosylpyrrole 7-Ts as a white solid in 40% or 58% yield, respectively. Michael addition of 7-Ts with mesityl oxide in the presence of TBAF[22] and 3 Å molecular sieves gave the detosylated pyrrole-hexanone 8 in 47% yield. The p-toluenesulfonyl group is known to be cleaved by TBAF.[23] Reduction[21] of 8 with excess zinc dust and $HCOONH_4$ in THF at room temperature gave the 8-bromo Western half 9 in 45% yield.

Scheme 2

-continued

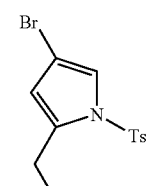

7-Ts

↓ 47% Mesityl oxide, TBAF
3A MS
DMF, RT, 3 h

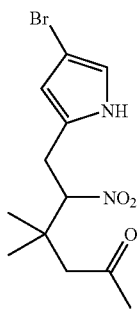

8

↓ 45% Zn, HCOONH₄
THF, RT

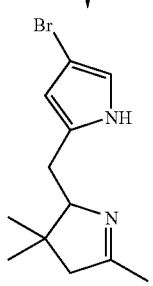

9

For the synthesis of 3,13-unsymmetrical chlorins, we considered functionalizing Western half 9 as a means of installing the required group prior to the chlorin-forming reaction. The synthesis of a Western half bearing a TIPS-ethynyl group at the 8-position is shown in Scheme 3. The Michael addition[10] of 7-Ts and mesityl oxide was carried out using CsF in anhydrous CH₃CN at 65° C., affording nitrohexanone 8-Ts in 30% yield along with a substantial amount of N-detosylated product 8 (~30%). CsF also is known to cause detosylation.[24] Similar reaction at room temperature for 16 h gave a similar product distribution. Commonly used bases[21] for Michael additions such as DBU or tetramethylguanidine did not give any trace of the required product 8-Ts. Reductive cyclization of 8-Ts in the presence of excess zinc dust and HCOONH₄ in THF at room temperature gave N-tosyl Western half 9-Ts in 74% yield. Sonogashira coupling of 9-Ts with (triisopropylsilyl)acetylene was carried out under conditions that have been used with pyrrolic compounds (20 mol % each of (PPh₃)₂PdCl₂ and CuI in THF and diisopropylamine)[25] gave 10-Ts in 54% yield. The selective deprotection[26] of the p-toluenesulfonyl group in the presence of the TIPS group was achieved by stirring a mixture of 10-Ts, HSCH₂COOH and LiOH in anhydrous DMF at 65° C. for 5 h.

Scheme 3

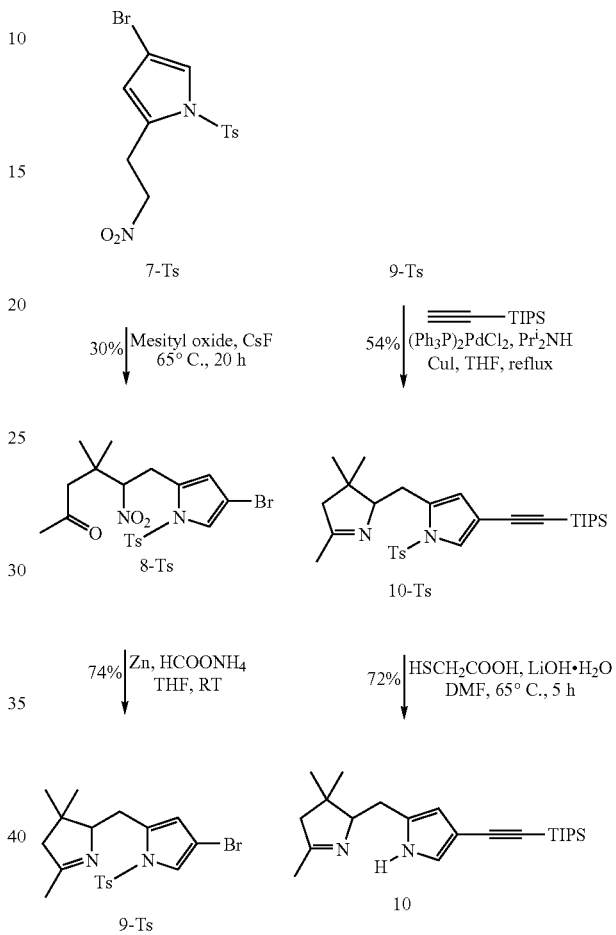

B. Chlorin Formation. The general chlorin-forming reaction entails p-TsOH·H₂O-catalyzed condensation of a 9-bromo-1-formyldipyrromethane species (Eastern half) and a 2,3,4,5-tetrahydro-1,3,3-trimethyldihydrodipyrrin species (Western half) followed by zinc-mediated oxidative cyclization as shown in eqn 1. Thus, a stirred suspension of an Eastern half (3-5, in slight excess) and a Western half with a substituent at the 8-position (9, 10) or no substituent (11) in anhydrous CH₂Cl₂ was treated with a solution of p-TsOH·H₂O in anhydrous MeOH under argon, affording a clear reddish-brown solution over 30-45 min. Workup afforded a yellow-brown foam-like solid, which was treated with Zn(OAc)₂, 2,2,6,6-tetramethylpiperidine (TMP) and AgOTf in CH₃CN at reflux exposed to air for 18-24 h. The chlorin was obtained by silica column chromatography. This route provided access to chlorins bearing H, Br, or TIPS-ethynyl at the 3-position, and H or Br at the 13-position, in yields ranging from 7 to 37% (Table 1).

TABLE 1

Effects of Substituents on Chlorin-Forming Reactions

| Entry | WH[a] | EH[b] | Chlorin substituents[c] | | | Chlorin | Yield %[d] |
| --- | --- | --- | --- | --- | --- | --- | --- |
| | | | 3 | 13 | 10 | | |
| 1 | 9 | 4 | Br | H | Mes | ZnC—Br$^3$M$^{10}$ | 37 |
| 2 | 11 | 5 | H | Br | Mes | ZnC—M$^{10}$Br$^{13}$ | 26 |
| 3 | 9 | 3 | Br | Br | H | ZnC—Br$^3$Br$^{13}$ | 26 |
| 4 | 9 | 5 | Br | Br | Mes | ZnC—Br$^3$M$^{10}$Br$^{13}$ | 30 |
| 5 | 10 | 3 | ≡—TIPS | Br | H | ZnC—E$^3$Br$^{13}$ | 7 |
| 6 | 10 | 5 | ≡—TIPS | Br | Mes | ZnC—E$^3$M$^{10}$Br$^{13}$ | 11 |

[a]Western half with no substituent (11) or a substituent at the 8-position.
[b]Eastern half.
[c]Numbering of chlorins is shown in Chart 1.
[d]Isolated yield.

In the 3-, 13- or 3,13-dibromochlorin-forming reactions, only one chlorin was isolated. In the 3,13-unsymetrically substituted chlorin-forming reactions, two chlorins in ~2:1 ratio were isolated from the crude mixture, of which the major product was the desired chlorin, and the minor chlorin was not identified. Each chlorin was characterized by absorption spectroscopy, $^1$H NMR spectroscopy, LD-MS, and FAB-MS analyses.

eqn 1

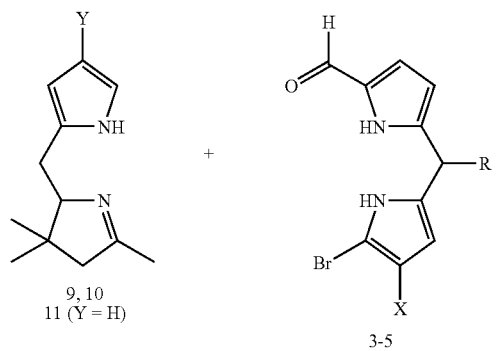

1) p-TsOH•H$_2$O
   CH$_2$Cl$_2$/MeOH
   RT, 30 min
2) AgOTf, Zn(OAc)$_2$, TMP
   reflux, 18-24 h -continued

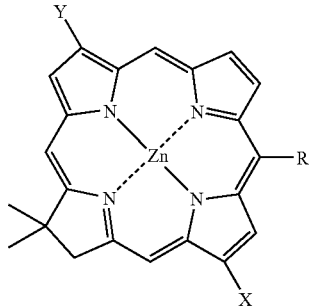

(C) Chlorin Derivatization. (i) 3-Substituted Chlorins. The syntheses of 3-vinylchlorin ZnC-V$^3$M$^{10}$ and 3-ethynylchlorin ZnC-E$^3$M$^{10}$ are shown in Scheme 4. Stille coupling of ZnC—Br$^3$M$^{10}$ and tributyl(vinyl)tin was carried out under conditions that have been employed with porphyrin substrates (10 mol % of (PPh$_3$)$_2$PdCl$_2$ in THF at reflux)[27] afforded 3-vinylchlorin ZnC-V$^3$M$^{10}$ in 66% yield. Sonogashira coupling of ZnC—Br$^3$M$^{10}$ and (triisopropylsilyl)acetylene was carried out under conditions that have been used with chlorins [Pd$_2$(dba)$_3$ and P(o-tol)$_3$ in toluene/TEA (5:1)][13] gave 3-ethynylchlorin ZnC-E$^3$M$^{10}$ in 52% yield. The latter conditions for Sonogashira coupling proceed under mild conditions and avoid the use of copper altogether, which can transmetalate with the zinc chelate.

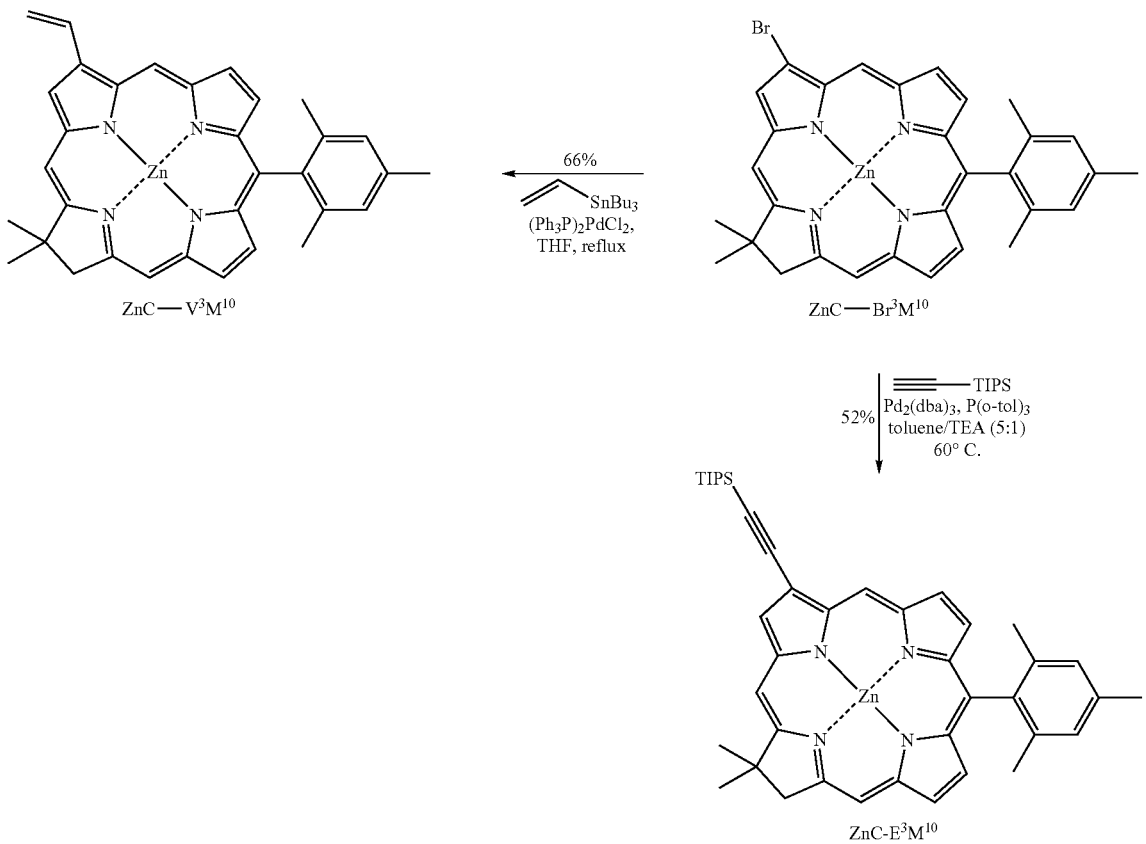

(ii) 13-Substituted Chlorins. The syntheses of 13-acetylchlorin ZnC-M[10]A[13] and 13-ethynylchlorin ZnC-M[10]E[13] are shown in Scheme 5. Chlorin ZnC-M[10]Br[13] was demetalated with TFA in $CH_2Cl_2$ at room temperature. The crude free base chlorin was subjected to Stille coupling with tributyl(1-ethoxyvinyl)tin[28] in the presence of 20 mol % of $Pd(PPh_3)_2$ $Cl_2$ in THF for 20 h. The hydrolysis of the reaction mixture with 10% aqueous HCl gave a crude product that on metalation with $Zn(OAc)_2 \cdot 2H_2O$ gave chlorin ZnC-M[10]A[13] in 53% overall yield. Sonogashira coupling of ZnC-M[10]Br[13] with (triisopropylsilyl)acetylene in the presence of $Pd_2(dba)_3$ and $P(o\text{-tol})_3$ gave 13-ethynylchlorin ZnC-M[10]E[13] in 71% yield.

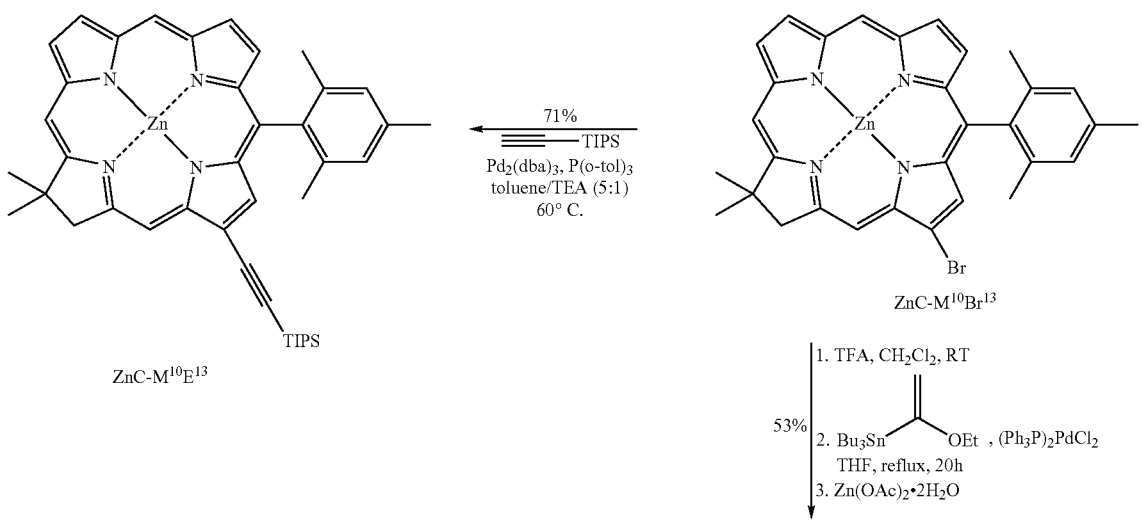

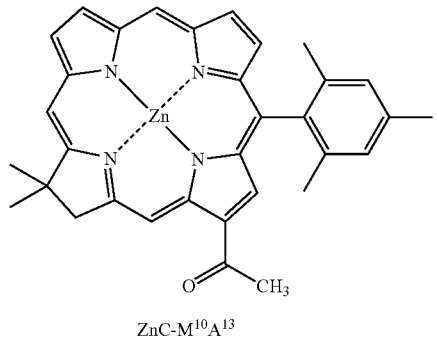

ZnC-M¹⁰A¹³

(iii) 3,13-Substituted Chlorins. The syntheses of 3,13-diethynylchlorins ZnC-E³E¹³ and ZnC-E³M¹⁰E¹³ are shown in Scheme 6. Sonogashira coupling of ZnC—Br³M¹⁰Br¹³ with (triisopropylsilyl)acetylene in the presence of 20 mol % of Pd(PPh$_3$)$_2$Cl$_2$ and CuI gave 3,13-diethynylchlorin ZnC-E³M¹⁰E¹³ in 42% yield along with the formation of a monoethynyl chlorin (15% yield) of unknown regiochemistry. The same coupling of ZnC—Br³Br¹³ or ZnC—Br³M¹⁰Br¹³ with (triisopropylsilyl)acetylene using the superior copper-free conditions (Pd$_2$(dba)$_3$ and P(o-tol)$_3$) gave 3,13-diethynylchlorin ZnC-E³A¹³ or ZnC-E³M¹⁰E¹³ in 53% or 75% yield, respectively.

Scheme 6

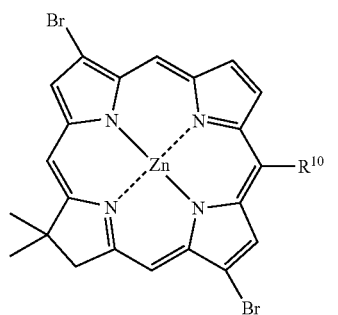

ZnC—Br³Br¹³   R¹⁰ = H
ZnC—Br³M¹⁰Br¹³  R¹⁰ = Mes

≡—TIPS
Pd$_2$(dba)$_3$, P(o-tol)$_3$
toluene/TEA (5:1)
60° C.

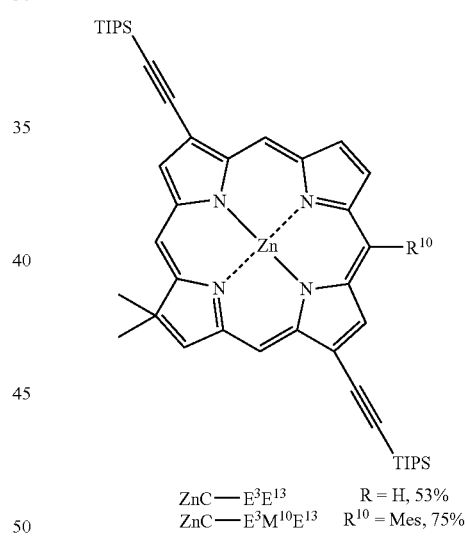

ZnC—E³E¹³    R = H, 53%
ZnC—E³M¹⁰E¹³  R¹⁰ = Mes, 75%

Following the protocol described above for the installation of the 13-acetyl group, the syntheses of 3-ethynyl-13-acetylchlorins ZnC-E³A¹³ and ZnC-E³M¹⁰A¹³ were carried out from their corresponding chlorins ZnC-E³Br¹³ and ZnC-E³M¹⁰Br¹³ as shown in Scheme 7. Thus, demetalation of ZnC-E³Br¹³ or ZnC-E³M¹⁰Br¹³, Stille coupling of the corresponding crude product with tributyl(1-ethoxyvinyl)tin, acidic workup, and zinc-metalation gave ZnC-E³A¹³ or ZnC-E³M¹⁰A¹³ in 53% or 23% overall yield, respectively.

Scheme 7

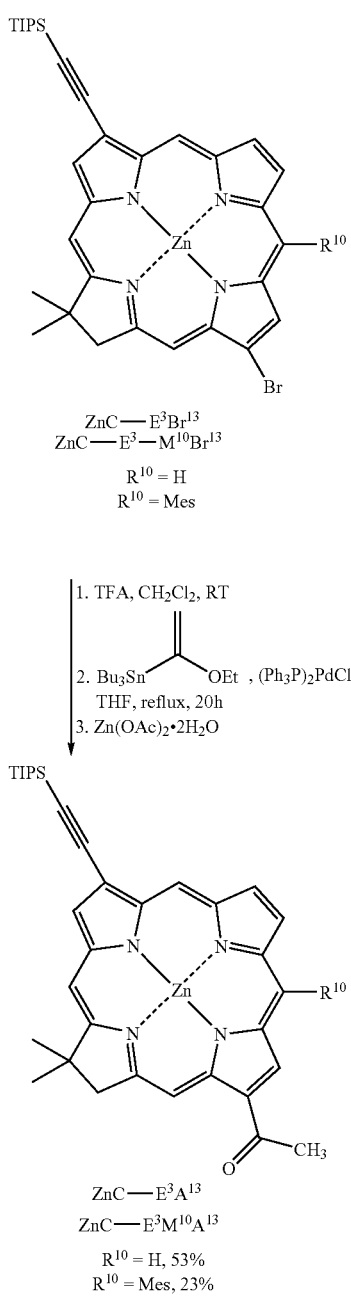

ZnC—E³Br¹³
ZnC—E³—M¹⁰Br¹³
R¹⁰ = H
R¹⁰ = Mes

1. TFA, CH₂Cl₂, RT
2. Bu₃Sn⟩=⟨OEt , (Ph₃P)₂PdCl₂  THF, reflux, 20h
3. Zn(OAc)₂·2H₂O ZnC—E³A¹³
ZnC—E³M¹⁰A¹³
R¹⁰ = H, 53%
R¹⁰ = Mes, 23%

II. Spectroscopy. A. NMR Spectroscopy. $^1$H NMR spectroscopy provides valuable information about the substitution patterns on chlorins. In all 3- and/or 13-substituted chlorins described herein, the following features are observed: (1) the geminal dimethyl groups resonate as a singlet at δ ~2.0 ppm; (2) the —CH₂ in the pyrroline ring gives rise to a singlet at δ ~4.5 ppm; (3) two meso protons ($H^x$ and $H^y$ in the 10-mesityl substituted chlorin family) or three meso protons ($H^w$, $H^x$ and $H^y$ in the unsubstituted chlorin family) each appear as singlet in the region δ 8.5-8.9 ppm, whereas the remaining meso proton ($H^z$) appears as a singlet in the region δ ~9.5-9.9 ppm; and (4) the two β-pyrrole protons ($H^7$, $H^8$) of the B ring each appear as a doublet (J=~4.1 Hz) at δ ~8.3-8.9 ppm. In the mono-substituted (3- or 13-substituted) chlorin series, an additional pair of doublets (J=4.1-4.4 Hz) is observed for the two β-pyrrole protons of the remaining unsubstituted pyrrole ring, and the lone β-pyrrole proton in the mono-substituted (3- or 13-substituted) pyrrole ring resonates as a singlet in the region δ ~8.2-9.1 ppm. In the 3,13-disubstituted chlorins, $H^2$ and $H^{12}$ each resonate as a singlet, and only one pair of doublets is observed. In the 13-acetylchlorins (ZnC-M¹⁰A¹³ and ZnC-E³M¹⁰A¹³), the vicinal β-pyrrole proton ($H^{12}$) resonates characteristically more downfield at δ 9.4-9.6 ppm.

B. Absorption Spectroscopy. The spectral properties of interest in the chlorins include the position of the long-wavelength $Q_y$ transition, the intensity of the $Q_y$ transition, and the fluorescence quantum yield of the chlorin. The intensity of the $Q_y$ transition can be assessed by the measured molar absorption coefficient; however, comparisons of such values are somewhat unreliable given the experimental variability encountered upon handling small quantities of materials. A better comparison is achieved by examination of the ratio of the intensities of the B and $Q_y$ bands for a given compound (B/$Q_y$ ratio), which is determined simply by absorption spectroscopy without requiring determination of the molar absorption coefficient. For a wide variety of applications, bathochromic and hyperchromic shifts of the $Q_y$ band are desired (i.e., shifted to longer wavelength and increased in intensity).

The spectral properties of the zinc chlorins are listed in Table 2. The spectral properties can be compared with those of zinc analogues of chlorophyll a and b,[29] as well as benchmark zinc chlorins lacking 3- and 13-substituents. The latter chlorins bear no substituent on the periphery of the macrocycle (ZnC) or a mesityl group at the 10-position (ZnC-M¹⁰) (structure block 1). Each parent chlorin exhibits a B band in the region 399-405 nm, a $Q_y$ band in the region 603-606 nm, and a B/$Q_y$ ratio in the range of 3.2-4.2.

The chlorins (in the 10-mesityl substituted family, FIG. 4) with a single substituent (such as vinyl, ethynyl or acetyl) at the 3- or 13-position each exhibit a B band in the region of 413-418 nm and a $Q_y$ band in the range from 621-632 nm.

The 3,13-substituted chlorins (in the 10-mesityl substituted family) each exhibit a B band in the region of 423-428 nm whereas 3,13-substituted chlorins (in the 10-unsubstituted family, FIG. 5) each exhibit a B band in the region of 421-428 nm. The $Q_y$ band of each 3,13-substituted chlorin lies in the range from 621 to 655 Zone Name: A1,AMD Zone Name: A2,AMD

TABLE 2

Absorption Properties of Chlorins[a]

| chlorins | $\lambda_{max}$ (nm), B | $\lambda_{max}$ (nm), $Q_y$ | $\Delta v_{Q_y}$ (cm$^{-1}$)[d] | B/$Q_y$ ratio |
|---|---|---|---|---|
| Zn-chlorophyll a[b] | 423 | 653 | NA | 1.4 |
| Zn-chlorophyll b[b] | 446 | 634 | NA | 2.9 |
| [c]ZnC-M¹⁰ | 405 | 606 | benchmark | 4.2 |
| ZnC-V³M¹⁰ | 413 | 621 | 400 | 3.3 |
| ZnC-E³M¹⁰ | 416 | 627 | 550 | 2.3 |
| ZnC-M¹⁰A¹³ | 418 | 632 | 680 | 2.2 |
| ZnC-M¹⁰E¹³ | 412 | 626 | 530 | 2.3 |
| ZnC-E³M¹⁰E¹³ | 10023 | 646 | 1020 | 1.6 |
| ZnC-E³M¹⁰A¹³ | 428 | 652 | 1160 | 1.5 |
| [c]ZnC | 399 | 603 | benchmark | 3.2 |
| ZnC-E³E¹³ | 421 | 645 | 1080 | 1.4 |
| ZnC-E³A¹³ | 428 | 655 | 1320 | 1.2 |

[a]In toluene at room temperature unless noted otherwise.
[b]Ref 29 (in diethyl ether).
[c]Ref 14.
[d]The redshift caused by the substituent pattern for a given compound relative to that of the parent chlorin (ZnC or Zn-M¹⁰).

The magnitude of the shift is given in energy units in Table 2. A single ethynyl group, acetyl group, or bromine atom altered the B/$Q_y$ ratio to ~3.3-2.2 (from 4.2 in the unsubstituted parent compound). The largest effect of a single substituent was observed with the 13-acetyl group. The enhancement in relative intensity and shift in wavelength of the $Q_y$ band in 13-acetylchlorins is explained as follows. The 13-acetyl group can adopt a planar conformation and thus conjugate with the π-electrons of the macrocycle. In this regard, it has been shown that the acetyl group of 13-acetylporphyrins in an unhindered β-pyrrolic position can adopt a planar conformation and thus comes in conjugation with the π-electron of the macrocycle.[30]

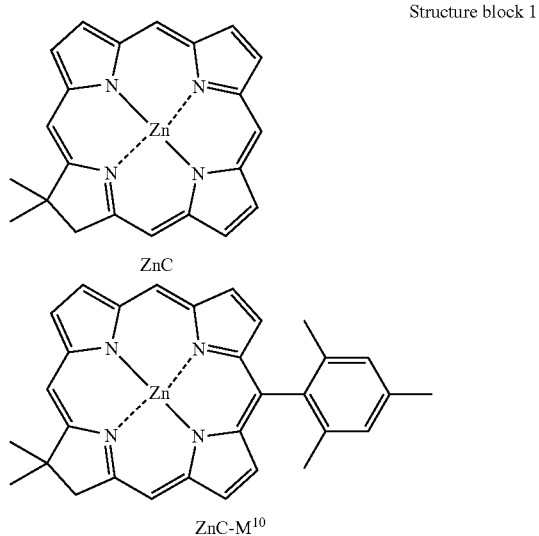

Structure block 1

ZnC

ZnC-M[10]

In chlorins, the $Q_y$ band is polarized along the N—N axis containing two pyrrole rings (not intersecting the pyrroline ring). A chlorin nominally has $C_{2v}$ symmetry,[31] in which case the 2- and 13-positions are symmetry equivalent, and the 3- and 12-positions are symmetry equivalent (Scheme 8). In practice, the presence of the geminal dimethyl group in the pyrroline ring of the synthetic chlorins prepared herein should have little effect on spectral properties. Although the 3- and 13-positions are not symmetry equivalent, each position resides in a pyrrole ring aligned along the $Q_y$ axis. In one case where a comparison could be made, the magnitude of the effect caused by a substituent at the 3-position was found to be quite similar to that at the 13-position: ZnC-E[3]M[10] and ZnC-M[10]E[13] exhibited nearly identical $Q_y$ band maxima (627 nm, 626 nm). Additional comparisons are required to more fully understand the effects of pyrrolic substituents at the two locations proximal (2 and 13) versus distal (3 and 12) to the pyrroline ring. Such comparisons are now possible with the synthetic methodology we have developed for preparing substituted chlorins.

CONCLUSIONS

Chlorins with different functional groups at 3- and 13-positions have been synthesized. In a zinc chlorin, the redshift of the $Q_y$ band caused by a 3-vinyl, 3-ethynyl, or 13-acetyl group is 15, 21, or 26 nm, respectively, from the benchmark at 606 nm. The redshift is comparable for the ethynyl group at the 3- or 13-position. The presence of an acetyl or ethynyl group at the 3- or 13-position also has a dramatic influence on the B/$Q_y$ band ratio. For example, the B/$Q_y$ band ratio (2.2) in chlorin ZnC-M[10]A[13] is much lower than that (4.2) of a chlorin lacking a 13-acetyl group. The presence of two ethynyl groups at the 3- and 13-positions redshifts the $Q_y$ band by 40-42 nm and increases the relative intensity of the $Q_y$ band dramatically (the B/$Q_y$ band ratio is 1.4-1.6 versus 3.2-4.2 for that of the parent chlorins. Similarly, the presence of a 3-ethynyl group and a 13-acetyl group redshifts the $Q_y$ band by 46-52 nm and increases the relative intensity of the $Q_y$ band dramatically (the B/$Q_y$ band ratio is 1.2-1.5).

This work complements studies of derivatives of naturally occurring chlorins that contain more extensive conjugative groups.[32] Ethynes do not occur in the natural compounds; however, ethynes are particularly attractive in ease of introduction, extending the conjugation, and providing a synthetic handle for further elaboration. Ethynes have been employed to good effect in porphyrin chemistry,[27,33] but have been relatively little examined with hydroporphyrins.[13,34] The synthetic approaches described herein should enable a much broader examination of the use of substituents to tune the spectra of chlorins.

Experimental Section

General. $^1$H NMR (400 MHz) and $^{13}$C NMR (75 MHz) spectra were collected at room temperature in CDCl$_3$ unless noted otherwise. Absorption spectra were obtained in toluene at room temperature. Chlorins were analyzed by laser desorption mass spectrometry (LD-MS) in the absence of a matrix. Metalation of free base chlorins was monitored by fluorescence spectroscopy. Melting points are uncorrected. All commercially available materials were used as received.

All the operations of chlorin forming reactions were performed on the same day starting from the preparation of 8,9-dibromo-1-formyldipyrromethanes. The condensation of Eastern half and Western half was carried out at room temperature under argon. The reaction mixture of the condensation reaction was quenched with ice-cold aqueous NaHCO$_3$. An ice-cold solution of the crude mixture in CH$_3$CN was treated with 2,2,6,6-tetramethylpiperidine followed by Zn(OAc)$_2$ and AgOTf. The reaction mixture was stirred at room temperature for 10-15 min before set it to gentle reflux.

All palladium-coupling reactions were performed using a Schlenk line. The Schlenk flask was attached, via thick-walled Tygon tubing, to a dual manifold. The flask containing all solid materials was evacuated via a vacuum pump for 3 min and after the evacuation period the flask was back-flushed with argon for 3 min. The process of evacuation and flushing was performed for a total of 3 times. At this time point the argon flow was turned up and the threaded stopcock was removed. Deaerated solvents were introduced by syringe. The threaded stopcock was replaced, and the argon flow rate was reduced. For Sonogashira couplings the flask was heated at 60-65° C., whereas for Stille couplings the reaction mixture was refluxed.

Noncommercial Compounds. Compounds 1, 2, and 4 were prepared following literature procedures.[16]

8,9-Dibromo-1-formyldipyrromethane (3). A solution of 1 (270 mg, 1.55 mmol) in dry THF (15.5 mL) at −78° C. under argon was treated with NBS (552 mg, 3.17 mmol). The reaction mixture was stirred for 1 h at −78° C. Hexanes and water were added at −20° C. and the mixture was allowed to warm to 0° C. The organic layer was separated, dried (K$_2$CO$_3$) and concentrated at ambient temperature. The resulting brown solid was purified by column chromatography [silica, hexanes/CH$_2$Cl$_2$/ethyl acetate (7:2:1)], affording a purple solid (290 mg, 56%): mp 109-111° C. (dec.); $^1$H NMR (THF-d$_8$) δ 3.93 (s, 2H), 5.89 (s, 1H), 6.05-6.07 (m, 1H), 6.78-6.79 (m, 1H), 9.37 (s, 1H), 10.81 (br s, 1H), 11.16 (br s, 1H); $^{13}$C NMR (THF-d$_8$) δ 26.0, 96.3, 98.0, 110.1, 112.7, 121.7, 128.9, 134.3, 139.0, 178.5; FAB-MS calcd 329.9003 (C$_{10}$H$_8$Br$_2$N$_2$O). Note: A significant amount (~30%) of the starting 1-formyldipyrromethane 1 was recovered in this reaction. Compound 3 in solution changes color from pale yellow to purple without any evidence of decomposition. The powdered solid 3 can be stored in the refrigerator for 2-3 weeks without decomposition.

8,9-Dibromo-1-formyl-5-mesityldipyrromethane (5). A solution of 2 (557 mg, 1.90 mmol) in dry THF (19 mL) at −78° C. under argon was treated with NBS (712 mg, 4.00 mmol). The reaction mixture was stirred for 1 h at −78° C. Hexanes and water were added at −20° C. and the mixture was allowed to warm to 0° C. The organic layer was separated, dried (K$_2$CO$_3$) and concentrated at ambient temperature. The resulting brown solid was purified by column chromatography [silica, hexanes/CH$_2$Cl$_2$/ethyl acetate (7:2:1)], affording a yellow solid (438 mg, 51%): mp 123-125° C. (dec.); $^1$H NMR (300 MHz, THF-d$_8$) δ 2.05 (s, 6H), 2.23 (s, 3H), 5.58-5.62 (m, 1H), 5.74 (s, 1H), 5.83-5.86 (m, 1H), 6.78-6.83 (m, 3H), 9.39 (s, 1H), 10.86 (br s, 1H), 11.16 (br s, 1H); $^{13}$C NMR (THF-d$_8$) δ 21.0, 21.1, 40.4, 98.3, 99.5, 111.3, 111.8, 131.1, 134.4, 134.5, 134.7, 137.4, 138.3, 141.9, 178.5; Anal. Calcd for C$_9$H$_{18}$Br$_2$N$_2$O: C, 50.69; H, 4.03; N, 6.22. Found: C, 50.70; H, 4.18; N, 6.03. Note: Careful handling of the solution of compound 5 is required. While it decomposes almost completely in solution (such as in ethyl acetate or chlorinated solvents) within 18-20 h even at 0° C., powdered solid 5 can be stored in the refrigerator for 5-7 days without decomposition. Evaporation of the solvent during workup or column chromatography should be done without heating. Compound 5 decomposed several times during NMR measurements (regardless of solvent such as CDCl$_3$ or THF-d$_8$) or attempted crystallization.

4-Bromopyrrole-2-carboxaldehyde (6). A solution of pyrrole-2-carboxaldehyde (4.75 g, 50.0 mmol) in dry THF (200 mL) was cooled to −78° C. under argon. NBS (8.90 g, 50.0 mmol) was added and the reaction mixture was stirred for 1 h at −78° C. Hexanes and water were added and the reaction mixture was allowed to warm to 0° C. The organic phase was extracted with hexanes and dried (Na$_2$SO$_4$). Crystallization of the crude mixture using hexanes/THF afforded white crystals (4.83 g, 55%): mp 120-121° C. [lit.[17] 122-123° C.]; $^1$H NMR δ 6.95 (m, 1H), 7.12 (m, 1H), 9.45 (s, 1H), 9.65-9.85 (br s, 1H); $^{13}$C NMR δ 99.0, 123.0, 127.0, 132.8, 179.3. Anal. Calcd for C$_5$H$_4$BrNO: C, 34.51; H, 2.32; N, 8.05. Found: C, 34.50; H, 2.26; N, 7.75. Note: Careful handling of the crude mixture is required. Evaporation of the solvent during workup should be done without heating. The use of ethyl acetate or any chlorinated solvent was avoided during workup or crystallization. The crystallization of the crude mixture was carried out by dissolving the off-white solid in THF by warming (40-50° C.) followed by addition of hexanes. The crude off-white solid very often turns reddish color which subsequently prevents crystallization. In that case, a small silica-pad filtration of the crude mixture is required before crystallization.

4-Bromo-2-formyl-N-p-tosylpyrrole (6-Ts). Following a reported procedure,[18] a stirred suspension of NaH (865 mg, 36.0 mmol) in THF (200 mL) was treated with 6 (5.22 g, 30.0 mmol) at room temperature. When the evolution of gas had ceased, the mixture was stirred for 1 h before treating with p-toluenesulfonyl chloride (6.30 g, 33.0 mmol). After 16 h, the conversion was complete as monitored by TLC. The reaction mixture was quenched by adding aqueous NH$_4$Cl. Ethyl acetate was added and the organic layer was separated. The organic layer was washed with water, brine and dried (Na$_2$SO$_4$). Concentration followed by crystallization (ethyl acetate/hexanes) afforded pale yellow crystals (6.75 g, 68%): mp 83-85° C.; $^1$H NMR δ 2.43 (s, 3H), 7.09 (d, J=2.0 Hz, 1H), 7.35 (d, J=8.3 Hz, 2H), 7.57 (d, J=2.0 Hz, 1H), 7.81 (d, J=8.3 Hz, 2H), 9.94 (s, 1H); $^{13}$C NMR δ 22.0, 101.8, 125.4, 127.8, 127.9, 130.6, 133.5, 134.7, 146.7, 178.5. Anal. Calcd or C$_{12}$H$_{10}$BrNO$_3$S: C, 43.92; H, 3.07; N, 4.27; S, 9.77. Found: C, 43.92; H, 3.02; N, 4.26; S, 9.84.

4-Bromo-2-(2-nitroethyl)-N-p-tosylpyrrole (7-Ts). Following a reported procedure,[28] a mixture of 6-Ts (1.64 g, 5.00 mmol), nitromethane (5.00 mL, 92.4 mmol) and ammonium acetate (270 mg, 3.50 mmol) was refluxed for 3 h. The reaction mixture was concentrated under reduced pressure. The residue was dissolved in ethyl acetate and the solution was washed (aqueous NaHCO$_3$, water and brine) and then dried (Na$_2$SO$_4$). Removal of the solvent gave a brown solid that was used directly in the next step. A stirred suspension of the crude product and Montmorillonite K10 in THF/methanol (3:2, 50 mL) was treated portionwise with NaBH$_4$ (284 mg, 7.50 mmol) at 0° C. The reaction mixture was stirred at room temperature for 1 h. Ethyl acetate was added and the reaction mixture was quenched by addition of saturated aqueous NH$_4$Cl. The organic layer was washed with water, dried (Na$_2$SO$_4$), and concentrated. The residue was chromatographed [silica, hexanes/CH$_2$Cl$_2$/ethyl acetate (8:1:1)] to give a white solid (760 mg, 40%): mp 125-127° C.; $^1$H NMR δ 2.44 (s, 3H), 3.81 (t, J=7.0 Hz, 2H), 4.60 (t, J=7.0 Hz, 2H), 6.09 (d, J=2.0 Hz, 1H), 7.31 (d, J=2.0 Hz, 1H), 7.35 (d, J=8.3 Hz, 2H), 7.68 (d, J=8.3 Hz, 2H); $^{13}$C NMR δ 21.9, 25.3, 74.3, 100.9, 117.3, 122.5, 127.0, 129.5, 130.7, 135.4, 146.2. Anal. Calcd for C$_{13}$H$_{13}$BrN$_2$O$_4$S: C, 41.84; H, 3.51; N, 7.51; S, 8.59. Found: C, 41.99; H, 3.43; N, 7.33; S, 8.80.

Alternative procedure: Following a reported procedure,[28] a mixture of 6-Ts (7.50 g, 22.8 mmol), nitromethane (21.6 mL, 405 mmol) and ammonium acetate (1.18 g, 15.3 mmol) was refluxed for 3 h. The reaction mixture was concentrated under reduced pressure. The residue was dissolved in ethyl acetate and the solution was washed with aqueous NaHCO$_3$, water and brine and then dried (Na$_2$SO$_4$). Removal of the solvent gave a brown solid that was used directly in the next step. Following a published procedure,[21] a solution of the crude product in CHCl$_3$ (195 mL) and 2-propanol (65 mL) was treated with silica (26.3 g). The resulting suspension was treated in three portions with NaBH$_4$ (1.65 g, 45.6 mmol) under vigorous stirring at room temperature. The reaction mixture was stirred for ~1.5 h and monitored by TLC. The reaction mixture was filtered. The filter cake was washed several times with CH$_2$Cl$_2$. The organic solution was washed with water and brine. The organic layer was dried (NaSO$_4$), concentrated, and subjected to high vacuum to remove traces of 2-propanol. The resulting residue was subjected to column chromatography [silica, hexanes/CH$_2$Cl$_2$/ethyl acetate (8:1:1)] to afford a pale yellow solid (4.95 g, 58%): mp 126-128° C.; $^1$H NMR (300 MHz) δ 2.44 (s, 3H), 3.38 (t, J=7.0 Hz, 2H), 4.60 (t, J=7.0 Hz, 2H), 6.09 (d, J=2.0 Hz, 1H), 7.31 (d, J=2.0 Hz, 1H), 7.35 (d, J=8.3 Hz, 2H), 7.68 (d, J=8.3 Hz, 2H); $^{13}$C NMR δ 21.9, 25.3, 74.3, 100.9, 117.3, 122.5, 127.0, 129.5, 130.7, 135.4, 146.2. Anal. Calcd for C$_{13}$H$_{13}$BrN$_2$O$_4$S: C, 41.84; H, 3.51; N, 7.51; S, 8.59.

4,4-Dimethyl-5-nitro-6-(1H-pyrrol-2-yl)hexan-2-one (8). Following a procedure,[22] a solution of TBAF.3H$_2$O (2.64 g, 8.36 mmol) in anhydrous DMF (25 mL) was stirred in the presence of 3 Å molecular sieves for 30 min at room temperature under argon. The stirred suspension was treated with a solution of 7-Ts (1.56 g, 4.18 mmol) and mesityl oxide (4.80 mL, 42.0 mmol) in anhydrous DMF (15 mL). The mixture was stirred at room temperature for 3 h. The reaction mixture was filtered through filter paper. The filtrate was concentrated under reduced pressure. The resulting residue was dissolved in ethyl acetate. The organic solution was washed with water, dried ($Na_2SO_4$), and chromatographed [silica, $CH_2Cl_2$] to give a viscous liquid (623 mg, 47%): $^1$H NMR (300 MHz) δ 1.09 (s, 3H), 1.22 (s, 3H), 2.14 (s, 3H), 2.40 (d, J=17.6 Hz, 1H), 2.58 (d, J=17.6 Hz, 1H), 2.97 (AB, J=15.2 Hz, 1H), 3.28 (ABX, $^2$J=15.2 Hz, $^3$J=11.6 Hz, 1H), 5.11 (ABX, $^2$J=11.6 Hz, $^3$J=3.5 Hz, 1H), 5.97-5.99 (m, 1H), 6.62-6.64 (m, 1H), 8.10-8.18 (br s, 1H); $^{13}$C NMR δ 24.3, 24.5, 26.8, 32.0. 36.9, 51.6, 94.4, 96.2, 110.0, 117.8, 127.3, 207.7; FAB-MS calcd 316.0423 ($C_{12}H_{17}BrN_2O_3$). Anal. Calcd for $Cl_2H_{17}BrN_2O_3$: C, 45.44; H, 5.40; N, 8.83. Found: C, 46.10; H, 5.30; N, 8.27. Note: Compound 8 (neat or in solution) changes color from yellow to black overtime (1-2 days) at room temperature indicating partial decomposition.

4,4-Dimethyl-5-nitro-6-(N-p-tosylpyrrol-2-yl)hexan-2-one (8-Ts). Following a literature procedure,[10] CsF (3.17 g, 20.9 mmol) was freshly dried by heating at 100° C. under vacuum for 1 h and then cooling to room temperature under argon. A solution of 7-Ts (2.60 g, 6.96 mmol) and mesityl oxide (8.16 mL, 71.0 mmol, 10 molar equiv) in dry acetonitrile (61 mL) was transferred by cannula to the flask containing CsF. The mixture was stirred at 65° C. for 18 h. The reaction mixture was filtered through a pad of silica and the filter cake was washed with ethyl acetate. The filtrate was concentrated under reduced pressure. Column chromatography [silica, hexanes/$CH_2Cl_2$/ethyl acetate (7:2:1)] of the crude product afforded a brown solid (0.980 g, 30%): mp 103-104° C.; $^1$H NMR δ 1.11 (s, 3H), 1.24 (s, 3H), 2.13 (s, 3H), 2.40 (AB, J=17.8 Hz, 1H), 2.43 (s, 3H), 2.55 (AB, J=17.8 Hz, 1H), 3.18 (AB, J=16.2 Hz, 1H), 3.36 (ABX, $^3$J=16.2 Hz, $^2$J=11.8 Hz, 1H), 5.14 (AB, J=11.8 Hz, 1H), 6.00-6.02 (m, 1H), 7.22-7.24 (m, 1H), 7.34 (AB, J=8.2 Hz, 2H), 7.64 (AB, J=8.2 Hz, 2H); $^{13}$C NMR δ 21.9, 23.7, 24.4, 26.4, 31.8. 36.9, 51.0, 93.5, 101.0, 117.0, 122.4, 126.8, 130.2, 130.6, 135.6, 146.0, 206.3; FAB-MS obsd 471.0596, calcd 471.0589 ($C_{19}H_{23}BrN_2O_5S$).

8-Bromo-2,3,4,5-tetrahydro-1,3,3-trimethyldipyrrin (9). Following a refined procedure,[21] a stirred suspension of 8 (350 mg, 1.10 mmol) and $HCOONH_4$ (1.04 g, 16.5 mmol) in THF (4.4 mL) was treated portionwise with Zn dust (1.07 g, 16.5 mmol) for 15 min. The reaction mixture was stirred vigorously for 3 h at room temperature. Ethyl acetate was added and the reaction mixture was filtered through filter paper. The filtrate was washed (half saturated aqueous $NaHCO_3$, water, brine), dried ($Na_2SO_4$), and chromatographed (silica, ethyl acetate), affording a yellow solid (135 mg, 45%): mp 83-84° C.; $^1$H NMR δ 0.92 (s, 3H), 1.11 (s, 3H), 2.03 (s, 3H), 2.28 (AB, J=16.8 Hz, 1H), 2.38 (AB, J=16.8 Hz, 1H), 2.54 (ABX, $^2$J=14.9 Hz, $^3$J=11.8 Hz, 1H), 2.69 (ABX, $^2$J=11.8 Hz, $^3$J=2.5 Hz, 1H), 3.56-3.62 (m, 1H), 5.85-5.94 (m, 1H), 6.63-6.69 (m, 1H), 9.72-10.01 (br s, 1H); $^{13}$C NMR δ 20.7, 23.0, 27.3, 27.8, 42.0, 54.4, 80.2, 95.2, 108.2, 116.5, 132.8, 175.1. Anal. Calcd for $C_{12}H_{17}BrN_2$: C, 53.54; H, 6.37; N, 10.41. Found: C, 53.15; H, 6.32; N, 10.11. Note: Stirring the reaction for prolonged time may cause the formation of side product.

9-Bromo-2,3,4,5-tetrahydro-1,3,3-trimethyl-N-p-tosyl-dipyrrin (9-Ts). A stirred suspension of 8-Ts (640 mg, 1.36 mmol) and $HCOONH_4$ (1.72 g, 27.2 mmol) in THF (6.0 mL) was treated portionwise with Zn dust (1.78 g, 27.2 mmol) for 5 min. The reaction mixture was stirred vigorously for 4 h at room temperature. Ethyl acetate was added and the reaction mixture was filtered through filter paper. The filtrate was washed (half-saturated aqueous $NaHCO_3$, water, brine), dried ($Na_2SO_4$), and chromatographed [silica, hexanes/ethyl acetate (1:1)], affording a viscous liquid (0.425 g, 74%): $^1$H NMR (300 MHz) δ 0.88 (s, 3H), 1.07 (s, 21H), 1.97 (s, 3H), 2.28 (AB, J=16.8 Hz, 1H), 2.36 (AB, J=16.8 Hz, 1H), 2.41 (s, 3H), 2.63 (ABX, $^2$J=16.1 Hz, $^3$J=10.2 Hz, 1H), 2.92 (ABX, $^2$J=16.1 Hz, $^3$J=3.8 Hz, 1H), 3.67-3.70 (m, 1H), 6.25-6.28 (m, 1H), 7.28-7.30 (m, 3H), 7.68 (AB, J=8.2 Hz, 2H); $^{13}$C NMR δ 20.6, 21.8, 22.9, 27.0, 28.0, 42.4, 54.4, 77.8, 101.0, 116.1, 121.0, 127.2, 130.2, 135.0, 135.9, 145.4, 175.0. FAB-MS obsd 423.0768, calcd 423.0742 ($C_{19}H_{23}BrN_2O_2S$).

9-[2-(Triisopropylsilyl)ethynyl]-2,3,4,5-tetrahydro-1,3,3-trimethyldipyrrin (10). Following a reported procedure,[26] a stirred suspension of 10-Ts (230 mg, 0.438 mmol) and LiOH (53.0 mg, 2.20 mmol) in anhydrous DMF (2 mL) was treated with $HSCH_2COOH$ (77.0 µL, 1.10 mmol) at room temperature. The reaction mixture was stirred for 5 h at 65° C. under argon. Ethyl acetate was added and the resulting mixture was washed (water, brine), dried ($Na_2SO_4$), concentrated, and chromatographed [silica, hexanes/ethyl acetate (1:1)], affording a white solid (118 mg, 72%): mp 110-112° C.; $^1$H NMR (300 MHz) δ 0.92 (s, 3H), 1.12 (s, 21H), 2.03 (s, 3H), 2.28 (AB, J=16.8 Hz, 1H), 2.37 (AB, J=16.8 Hz, 1H), 2.51 (ABX, $^2$J=14.9 Hz, $^3$J=11.8 Hz, 1H), 2.68 (ABX, $^2$J=14.9 Hz, $^3$J=2.8 Hz, 1H), 3.56-3.59 (m, 1H), 6.01-6.03 (m, 1H), 6.90-6.92 (m, 1H), 9.90-9.93 (br s, 1H); $^{13}$C NMR δ 11.6, 18.9, 20.6, 23.0, 27.3, 27.7, 42.0, 54.4, 80.1, 87.2, 103.7, 104.0, 109.4, 121.9, 131.8, 175.6. Anal. Calcd for $C_{23}H_{38}N_2Si$: C, 74.53; H, 10.33; N, 7.56. Found: C, 74.25; H, 10.29; N, 7.49.

N-p-Tosyl-3-[2-(triisopropylsilyl)ethynyl]-2,3,4,5-tetrahydro-1,3,3-trimethyldipyrrin (10-Ts). A mixture of 9-Ts (0.560 g, 1.32 mmol), (triisopropylsilyl)acetylene (0.590 mL, 2.65 mmol), $(PPh_3)_2PdCl_2$ (186 mg, 0.265 mmol), diisopropylamine (0.930 mL, 6.63 mmol) and CuI (50.0 mg, 0.262 mmol) was refluxed in THF (6 mL) for 20 h in a Schlenk line. The reaction mixture was concentrated and chromatographed [silica, hexanes/ethyl acetate (1:1)] affording a viscous liquid (375 mg, 54%): $^1$H NMR (300 MHz) δ 0.87 (s, 3H), 1.07 (s, 21H), 1.97 (s, 3H), 2.26 (AB, J=16.8 Hz, 1H), 2.35 (AB, J=16.8 Hz, 1H), 2.40 (s, 3H), 2.60 (ABX, $^2$J=16.2 Hz, $^3$J=10.1 Hz, 1H), 2.86 (ABX, $^2$J=16.2 Hz, $^3$J=3.8 Hz, 1H), 3.68-3.70 (m, 1H), 6.28-6.30 (m, 1H), 7.28 (d, J=8.1 Hz, 2H), 7.46-7.47 (m, 1H), 7.68 (d, J=8.1 Hz, 2H); $^{13}$C NMR δ 11.5, 18.8, 20.7, 21.8, 23.0, 27.2, 28.0, 42.4, 54.6, 77.9, 91.1, 100.5, 108.6, 116.2, 125.9, 127.3, 130.3, 134.1, 136.0, 145.4, 175.2. FAB-MS obsd 525.2966 (M+H)$^+$, calcd 524.2893 ($C_{30}H_{44}N_2O_2SSi$).

Zn(II)-3-Bromo-17,18-dihydro-10-mesityl-18,18-dimethylporphyrin (ZnC—Br$^3$M$^{10}$). Following a standard procedure,[14] a solution of 4 (75 mg, 0.20 mmol) and 9 (54 mg, 0.20 mmol) in distilled $CH_2Cl_2$ (6 mL) was treated with a solution of p-TsOH.$H_2O$ (0.19 g, 1.0 mmol) in distilled methanol (2 mL) under argon. The red reaction mixture was stirred at room temperature for 30 min. The reaction mixture was washed (10% $NaHCO_3$, water, brine), dried ($Na_2SO_4$), and concentrated, yielding a brown solid. The solid was dissolved in $CH_3CN$ (20 mL) and subsequently treated with 2,2,6,6-tetramethylpiperidine (0.340 mL, 2.00 mmol), $Zn(OAc)_2$ (370 mg, 2.00 mmol) and AgOTf (154 mg, 0.600 mmol). The resulting suspension was refluxed for 14 h exposed to air. The crude mixture was concentrated and chromatographed [silica, $CH_2Cl_2$], affording a green solid (45 mg, 37%): $^1$H NMR δ 1.85 (s, 6H), 2.01 (s, 6H), 2.60 (s, 3H), 4.50 (s, 2H), 7.23 (s, 2H), 8.37 (d, J=4.1 Hz, 1H), 8.50 (s, 1H), 8.55 (d, J=4.4 Hz, 1H), 8.60 (d, J=4.4 Hz, 1H), 8.68 (s, 1H), 8.77 (s, 1H), 8.88 (d, J=4.1 Hz, 1H), 9.73 (s, 1H); LD-MS obsd 598.3; FAB-MS obsd 598.0750, calcd 598.0711 ($C_{31}H_{27}BrN_4Zn$); $\lambda_{abs}$ 408, 614 nm.

Zn(II)-13-Bromo-17,18-dihydro-10-mesityl-18,18-dimethylporphyrin (ZnC-M$^{10}$Br$^{13}$). Following a standard procedure,[14] a solution of 5 (245 mg, 0.544 mmol) and 11 (86.4 mg, 0.452 mmol) in distilled $CH_2Cl_2$ (13 mL) was treated with a solution of p-TsOH.$H_2O$ (0.430 g, 2.26 mmol) in distilled methanol (5 mL) under argon. The reaction mixture was stirred at room temperature for 30 min. Workup followed by concentration of the crude mixture afforded a yellow foam-like solid. The solid was dissolved in $CH_3CN$ (45 mL) and subsequently treated with 2,2,6,6-tetramethylpiperidine (1.15 mL, 6.81 mmol), Zn(OAc)$_2$ (829 mg, 4.52 mmol) and AgOTf (348 mg, 1.35 mmol). The resulting suspension was refluxed for 18 h exposed to air. The crude mixture was concentrated and chromatographed [silica, hexanes/$CH_2Cl_2$ (2:1)], affording a purple solid (72 mg, 26%): $^1$H NMR δ 1.86 (s, 6H), 2.03 (s, 6H), 2.60 (s, 3H), 4.52 (s, 2H), 7.23 (s, 2H), 8.37 (d, J=4.4 Hz, 1H), 8.57 (s, 1H), 8.61 (s, 1H), 8.72 (d, J=3.5 Hz, 1H), 8.80 (d, J=3.5 Hz, 1H), 8.85 (s, 1H), 9.01 (d, J=4.4 Hz, 1H), 9.54 (s, 1H); LD-MS obsd 598.5 (M$^+$), 518.8 [(M-Br)$^+$]; FAB-MS obsd 598.0737, calcd 598.0711 ($C_{31}H_{27}BrN_4Zn$); $\lambda_{abs}$ 406, 613 nm.

Zn(II)-3,13-Dibromo-17,18-dihydro-18,18-dimethylporphyrin (ZnC—Br$^3$Br$^{13}$). Following a standard procedure,[14] a solution of 3 (68.0 mg, 0.205 mmol) and 9 (56.0 mg, 0.205 mmol) in distilled $CH_2Cl_2$ (4 mL) was treated with a solution of p-TsOH.$H_2O$ (195 mg, 1.03 mmol) in distilled methanol (1 mL) under argon. The red reaction mixture was stirred at room temperature for 50 min. The reaction mixture was washed (10% NaHCO$_3$, water, brine), dried (Na$_2$SO$_4$), and concentrated, which yielded a brown solid. The solid was dissolved in $CH_3CN$ (20.5 mL) and subsequently treated with 2,2,6,6-tetramethylpiperidine (0.523 mL, 3.07 mmol), Zn(OAc)$_2$ (790 mg, 3.07 mmol), and AgOTf (113 mg, 0.615 mmol). The resulting suspension was refluxed for 19 h exposed to air. The crude mixture was concentrated and chromatographed [silica, $CH_2Cl_2$/hexanes, (2:1)], affording a green solid (30.0 mg, 26%): $^1$H NMR (THF-d$_8$) δ 2.03 (s, 6H), 4.57 (s, 2H), 8.65 (s, 1H), 8.67 (s, 1H), 8.82 (s, 1H), 8.87 (s, 1H), 9.03 (s, 2H), 9.73 (s, 1H), 9.75 (s, 1H); LD-MS obsd 562.8; FAB-MS obsd 557.9050, calcd 557.9033 ($C_{22}H_{16}Br_2N_4Zn$); $\lambda_{abs}$ 405, 620 nm.

Zn(II)-3,13-Dibromo-17,18-dihydro-10-mesityl-18,18-dimethylporphyrin (ZnC—Br$^3$M$^{10}$Br$^{13}$). A stirred suspension of 5 (360 mg, 0.800 mmol) and 9 (108 mg, 0.400 mmol) in distilled $CH_2Cl_2$ (10 mL) was treated with a solution of p-TsOH.$H_2O$ (380 mg, 2.00 mmol) in distilled methanol (6 mL) under argon. The reaction mixture was stirred at room temperature for 30 min. Workup followed by concentration of the crude mixture afforded a brown solid. The solid was dissolved in $CH_3CN$ (40 mL) and subsequently treated with 2,2,6,6-tetramethylpiperidine (1.00 mL, 6.00 mmol), Zn(OAc)$_2$ (734 mg, 4.00 mmol), and AgOTf (308 mg, 1.20 mmol). The resulting suspension was refluxed for 14 h exposed to air. The crude mixture was concentrated and chromatographed [silica, hexanes/$CH_2Cl_2$ (2:1)], affording a blue solid (83.0 mg, 30%): $^1$H NMR (300 MHz, THF-d$_8$) δ 1.84 (s, 6H), 2.03 (s, 6H), 2.58 (s, 3H), 4.56 (s, 2H), 7.24 (s, 2H), 8.26 (d, J=4.4 Hz, 1H), 8.41 (s, 1H), 8.57 (s, 1H), 8.78 (s, 1H), 8.81 (s, 1H), 8.84 (d, J=4.4 Hz, 1H), 9.62 (s, 1H); LD-MS obsd 679.6; FAB-MS obsd 675.9827, calcd 675.9816 ($C_{31}H_{26}Br_2N_4Zn$); $\lambda_{abs}$ 411, 622 nm.

Zn(II)-3-[2-(Triisopropylsilyl)ethynyl]-13-bromo-17,18-dihydro-18,18-dimethyl-porphyrin (ZnC-E$^3$Br$^{13}$). A solution of 3 (90.0 mg, 0.270 mmol) and 10 (91.0 mg, 0.245 mmol) in distilled $CH_2Cl_2$ (8 mL) was treated with a solution of p-TsOH.$H_2O$ (233 mg, 1.22 mmol) in distilled methanol (2 mL) under argon. The reaction mixture was stirred at room temperature for 45 min. Workup followed by concentration of the crude mixture afforded a yellow solid. The crude yellow solid was dissolved in $CH_3CN$ (24.5 mL) and subsequently treated with 2,2,6,6-tetramethylpiperidine (624 μL, 3.67 mmol), Zn(OAc)$_2$ (944 mg, 3.67 mmol), and AgOTf (135 mg, 0.735 mmol). The resulting suspension was refluxed for 18 h exposed to air. The crude mixture was concentrated and chromatographed [silica, hexanes/$CH_2Cl_2$ (6:4)], affording a purple solid (12.0 mg, 7%): $^1$H NMR (THF-d$_8$) δ 1.43-1.44 (m, 21H), 2.03 (s, 6H), 4.57 (s, 2H), 8.66 (s, 2H), 8.82 (s, 1H), 8.90 (s, 1H), 8.95 (d, J=4.0 Hz, 1H), 9.01 (d, J=4.0 Hz, 1H), 9.71 (s, 1H), 9.88 (s, 1H); LD-MS obsd 661.9.0; FAB-MS obsd 660.1266, calcd 660.1262 ($C_{33}H_{37}BrN_4SiZn$); $\lambda_{abs}$ 418, 634 nm.

Zn(II)-13-Bromo-17,18-dihydro-10-mesityl-18,18-dimethyl-3-[2-(triisopropylsilyl)ethynyl]porphyrin (ZnC-E$^3$M$^{10}$Br$^{13}$). A stirred suspension of 5 (160 mg, 0.355 mmol) and 10 (110 mg, 0.300 mmol) in distilled $CH_2Cl_2$ (8.5 mL) was treated with a solution of p-TsOH.$H_2O$ (283 mg, 1.50 mmol) in distilled methanol (3.5 mL) under argon. The reaction mixture was stirred at room temperature for 30 min. Workup followed by concentration of the crude mixture afforded a yellow viscous liquid. The viscous liquid was dissolved in $CH_3CN$ (30 mL) and subsequently treated with 2,2,6,6-tetramethylpiperidine (0.750 mL, 4.50 mmol), Zn(OAc)$_2$ (545 mg, 3.00 mmol), and AgOTf (228 mg, 0.890 mmol). The resulting suspension was refluxed for 16 h exposed to air. The crude mixture was concentrated and chromatographed [silica, hexanes/$CH_2Cl_2$ (2:1)], affording a purple solid (26.0 mg, 11%): $^1$H NMR δ (300 MHz, THF-d$_8$) 1.30 (s, 3H), 1.43 (m, 18H), 1.85 (s, 6H), 2.03 (s, 6H), 2.60 (s, 3H), 4.57 (s, 2H), 7.25 (s, 2H), 8.26 (d, J=4.0 Hz, 1H), 8.41 (d, J=4.0 Hz, 1H), 8.58-8.60 (m, 1H), 8.77 (d, J=4.0 Hz, 2H), 8.84-8.87 (m, 1H), 9.76-9.78 (m, 1H); LD-MS obsd 779.0; FAB-MS obsd 778.2038, calcd 778.2045 ($C_{42}H_{17}BrN_4SiZn$); $\lambda_{abs}$ 418, 634 nm.

Zn(II)-17,18-Dihydro-10-mesityl-18,18-dimethyl-3-vinylporphyrin (ZnC-V$^3$M$^{10}$). Following a procedure for Stille coupling with porphyrins,[27] a mixture of ZnC—Br$^3$M$^{10}$ (20 mg, 33 μmol), Bu$_3$SnCH=CH$_2$ (20 μL, 68 μmol) and (PPh$_3$)$_2$PdCl$_2$ (3.0 mg, 4.0 μmol) was refluxed in THF (2 mL) for 14 h in a Schlenk line. The reaction mixture was concentrated and chromatographed [silica, $CH_2Cl_2$], affording a blue solid (12 mg, 66%): $^1$H NMR δ 1.86 (s, 6H), 2.02 (s, 6H), 2.60 (s, 3H), 4.50 (s, 2H), 5.85 (d, J=10.8 Hz, 1H), 6.47 (d, J=17.5 Hz, 1H), 7.23 (s, 2H), 8.19 (dd, J=17.5, 10.8 Hz, 1H), 8.33 (d, J=4.1 Hz, 1H), 8.50 (d, J=4.4 Hz, 1H), 8.52 (s, 1H), 8.55 (d, J=4.4 Hz, 1H), 8.59 (s, 1H), 8.81 (d, J=4.1 Hz, 1H), 8.83 (s, 1H), 9.68 (s, 1H); LD-MS obsd 546.7; FAB-MS obsd 546.1739, calcd 546.1762 ($C_{33}H_{30}N_4Zn$); $\lambda_{abs}$ 414, 621 nm.

Zn(II)-3-(2-(Triisopropylsilyl)ethynyl)-17,18-dihydro-10-mesityl-18,18-dimethylporphyrin (ZnC-E$^3$M$^{10}$). Following a procedure for Sonogashira coupling with chlorins,[13] a mixture of ZnC—Br$^3$M$^{10}$ (18 mg, 0.030 mmol), (triisopropylsilyl)acetylene (14 μL, 0.060 mmol), Pd$_2$(dba)$_3$ (4.2 mg, 0.0045 mmol), and P(o-tol)$_3$ (11 mg, 0.036 mmol) was heated at 60° C. in toluene/triethylamine (5:1, 12 mL) in a Schlenk line. After 7 h, (triisopropylsilyl)acetylene (14 μL, 0.060 mmol), Pd$_2$(dba)$_3$ (4.2 mg, 0.0045 mmol), and P(o-tol)$_3$ (11 mg, 0.036 mmol) were added to the reaction mixture. After 18 h, the reaction mixture was concentrated and chromatographed [silica, hexanes/$CH_2Cl_2$ (2:1)], affording a green solid (11 mg, 52%): $^1$H NMR δ 1.38 (s, 18H), 1.40 (m, 3H), 1.85 (s, 6H), 2.01 (s, 6H), 2.60 (s, 3H), 4.51 (s, 2H), 7.22 (s, 2H), 8.36 (d, J=4.1 Hz, 1H), 8.50-8.54 (m, 2H), 8.60 (d, J=4.1 Hz, 1H), 8.67 (s, 1H), 8.80-8.85 (m, 2H), 9.88 (s, 1H); LD- MS obsd 700.5; FAB-MS obsd 700.2930, calcd 700.2940 ($C_{42}H_{48}N_4SiZn$); $\lambda_{abs}$ 416, 627 nm.

Zn(II)-13-Acetyl-17,18-dihydro-10-mesityl-18,18-dimethylporphyrin (ZnC-M[10]A[13]). A solution of ZnC-M[10]Br[13] (50 mg, 0.083 mmol) in $CH_2Cl_2$ (1.0 mL) was treated dropwise with TFA (0.13 mL, 1.6 mmol) over 2 min. The solution was stirred at room temperature for 2 h. $CH_2Cl_2$ was added and the organic layer was washed (saturated aqueous $NaHCO_3$, water, brine) and then dried ($Na_2SO_4$). The crude mixture was concentrated and used in the next step. Following a procedure for replacement of a bromo group with an acetyl group on an aromatic substrate,[28] a mixture of the crude product, tributyl(1-ethoxyvinyl)tin (49 μL, 0.14 mmol) and $(PPh_3)_2PdCl_2$ (10 mg, 0.014 mmol) was refluxed in THF (7 mL) for 20 h in a Schlenk line. The reaction mixture was treated with 10% aqueous HCl (4 mL) at room temperature for 2 h. $CH_2Cl_2$ was added and the organic layer was separated. The organic layer was washed (saturated aqueous $NaHCO_3$, water, brine), dried ($Na_2SO_4$), and concentrated. The resulting residue was dissolved in $CHCl_3$ (5 mL). The solution was treated with $Zn(OAc)_2 \cdot 2H_2O$ (320 mg, 1.45 mmol) in MeOH (2 mL) and the reaction mixture was stirred overnight at room temperature. Concentration followed by chromatography of the crude mixture [silica, $CH_2Cl_2$/hexanes (1:1)] gave a green solid (25 mg, 53%): $^1$H NMR δ 1.82 (s, 6H), 2.00 (s, 6H), 2.60 (s, 3H), 2.72 (s, 3H), 4.47 (s, 2H), 7.20 (s, 2H), 8.30 (d, J=4.4 Hz, 1H), 8.48 (s, 1H), 8.68 (d, J=4.4 Hz, 2H), 8.81 (s, 1H), 8.96 (d, J=4.4 Hz, 1H), 9.38 (s, 1H), 9.55 (s, 1H); LD-MS obsd 560.7; FAB-MS obsd 562.1745, calcd 562.1711 ($C_{33}H_{30}N_4OZn$); $\lambda_{abs}$ 418, 587, 632 nm.

Zn(II)-13-[2-(Triisopropylsilyl)ethynyl]-17,18-dihydro-10-mesityl-18,18-dimethylporphyrin (ZnC-M[10]E[13]). A mixture of ZnC-M[10]Br[13] (18 mg, 0.030 mmol), (triisopropylsilyl)acetylene (14 μL, 0.060 mmol), $Pd_2(dba)_3$ (4.2 mg, 0.0045 mmol), and $P(o\text{-tol})_3$ (11 mg, 0.036 mmol) was heated at 60° C. in toluene/triethylamine (5:1, 12 mL) in a Schlenk line. After 7 h, (triisopropylsilyl)acetylene (14 μL, 0.060 mmol), $Pd_2(dba)_3$ (4.2 mg, 0.0045 mmol), and $P(o\text{-tol})_3$ (11 mg, 0.036 mmol) were added to the reaction mixture. After 18 h, the reaction mixture was concentrated and chromatographed [silica, hexanes/$CH_2Cl_2$ (2:1)], affording a green solid (15 mg, 71% yield): $^1$H NMR δ 1.38 (s, 18H), 1.40 (s, 3H), 1.85 (s, 6H), 2.02 (s, 6H), 2.60 (s, 3H), 4.51 (s, 2H), 7.24 (s, 2H), 8.35 (d, J=4.1 Hz, 1H), 8.55 (s, 1H), 8.59 (s, 1H), 8.66 (d, J=4.1 Hz, 1H), 8.76 (d, J=4.1 Hz, 1H), 9.00-9.02 (m, 2H), 9.51 (s, 1H); LD-MS obsd 698.5; FAB-MS obsd 562.1745, calcd 700.2940 ($C_{42}H_{49}N_4SiZn$); $\lambda_{abs}$ 412, 577, 626 nm.

Zn(II)-3,13-Bis[2-(triisopropylsilyl)ethynyl]-17,18-dihydro-18,18-dimethyl-porphyrin (ZnC-E[3]E[13]). Following a reported procedure,[13] samples of ZnC—Br[3]Br[13] (12.0 mg, 0.0214 mmol) and (triisopropylsilyl)acetylene (28.5 μL, 0.128 mmol) were coupled using $Pd_2(dba)_3$ (2.90 mg, 0.00321 mmol) and $P(o\text{-tol})_3$ (8.50 mg, 0.0256 mmol) in toluene/triethylamine (5:1, 9 mL) at 60° C. under argon. After 5 h, (triisopropylsilyl)acetylene (28.5 μL, 0.128 mmol), $Pd_2(dba)_3$ (2.90 mg, 0.00321 mmol), and $P(o\text{-tol})_3$ (8.50 mg, 0.0256 mmol) were added to the reaction mixture. After 24 h, the reaction mixture was concentrated under reduced pressure. The resulting residue was chromatographed [silica, hexanes/$CH_2Cl_2$ (8:2)], affording a greenish purple solid (8.6 mg, 53%): $^1$H NMR (THF-$d_8$) δ 1.42-1.45 (m, 42H), 2.03 (s, 6H), 4.57 (s, 2H), 8.65 (s, 1H), 8.69 (s, 1H), 8.86 (s, 1H), 8.90 (s, 1H), 8.95 (s, 2H), 9.85 (s, 1H), 9.87 (s, 1H); LD-MS obsd 763.9; FAB-MS obsd 762.3492, calcd 762.3492 ($C_{44}H_{58}N_4Si_2Zn$); $\lambda_{abs}$ 421, 645 nm.

Zn(II)-3,13-Bis [2-(triisopropylsilyl)ethynyl]-17,18-dihydro-10-mesityl-18,18-dimethylporphyrin (ZnC-E[3]M[10]E[13]). Samples of ZnC—Br[3]M[10]Br[13] (25 mg, 0.036 mmol) and (triisopropylsilyl)acetylene (16 μL, 0.072 mmol) were coupled using $Pd_2(dba)_3$ (5.0 mg, 0.0055 mmol), and $P(o\text{-tol})_3$ (14 mg, 0.046 mmol) in toluene/triethylamine (5:1, 9 mL) at 60° C. under argon. After 20 h, (triisopropylsilyl)acetylene (16 μL, 0.072 mmol), $Pd_2(dba)_3$ (5.0 mg, 0.0055 mmol), and $P(o\text{-tol})_3$ (14 mg, 0.046 mmol) were added to the reaction mixture. After 32 h, the reaction mixture was concentrated under reduced pressure. The resulting residue was chromatographed [silica, hexanes/$CH_2Cl_2$ (2:1)], affording a green solid (24 mg, 75%): $^1$H NMR δ 1.38 (s, 18H), 1.40 (s, 24H), 1.86 (s, 6H), 2.03 (s, 6H), 2.61 (s, 3H), 4.52 (s, 2H), 7.24 (s, 2H), 8.34 (d, J=3.9 Hz, 1H), 8.50 (s, 1H), 8.56 (s, 1H), 8.80 (d, J=3.9 Hz, 1H), 8.83 (s, 1H), 8.99 (s, 1H), 9.81 (s, 1H); LD-MS obsd 880.4; FAB-MS obsd 880.4321, calcd 880.4274 ($C_{53}H_{68}N_4Si_2Zn$); $\lambda_{abs}$ 423, 646 nm.

Zn(I)-13-Acetyl-3-[2-(triisopropylsilyl)ethynyl]-17,18-dihydro-18,18-dimethyl-porphyrin (ZnC-E[3]A[13]). A solution of ZnC-E[3]Br[13] (8.0 mg, 0.012 mmol) in $CH_2Cl_2$ (0.2 mL) was treated dropwise with TFA (29 μL, 0.36 mmol) over 2 min. The solution was stirred at room temperature for 2 h. $CH_2Cl_2$ was added and the organic layer was washed (saturated aqueous $NaHCO_3$, water, brine) and then dried ($Na_2SO_4$). The crude mixture was concentrated and used in the next step. A mixture of the crude product, tributyl(1-ethoxyvinyl)tin (17 μL, 0.048 mmol) and $(PPh_3)_2PdCl_2$ (1.3 mg, 0.0018 mmol) was refluxed in THF (1.2 mL) for 20 h in a Schlenk line. The reaction mixture was treated with 10% aqueous HCl (0.5 mL) at room temperature for 2 h. $CH_2Cl_2$ was added and the organic layer was separated. The organic layer was washed (saturated aqueous $NaHCO_3$, water, brine), dried ($Na_2SO_4$), and concentrated. The resulting residue was dissolved in $CHCl_3$ (0.8 mL). The solution was treated with $Zn(OAc)_{2-2}$ $H_2O$ (40 mg, 0.18 mmol) in MeOH (0.2 mL) and the reaction mixture was stirred for 4 h at room temperature. Concentration followed by chromatography of the crude mixture [silica, $CH_2Cl_2$] gave a green solid (4.0 mg, 53%): $^1$H NMR (THF-$d_8$) δ 1.42 (s, 21H), 2.04 (s, 6H), 3.13 (s, 3H), 4.57 (s, 2H), 8.67 (s, 1H), 8.78 (s, 1H), 8.92 (s, 2H), 8.94 (d, J=4.4 Hz, 1H), 9.06 (d, J=4.4 Hz, 1H), 9.32 (s, 1H), 9.84 (s, 1H); LD-MS obsd 624.3; FAB-MS obsd 624.2256, calcd 624.2263 ($C_{35}H_{40}N_4OSiZn$); $\lambda_{abs}$ 428, 655 nm.

Zn(II)-13-Acetyl-3-[2-(triisopropylsilyl)ethynyl]-17,18-dihydro-10-mesityl-18,18-dimethylporphyrin (ZnC-E[3]M[10]A[13]). A solution of ZnC-E[3]M[10]Br[13] (19 mg, 0.024 mmol) in $CH_2Cl_2$ (0.25 mL) was treated dropwise with TFA (38 μL, 0.49 mmol) over 2 min. The solution was stirred at room temperature for 3 h. $CH_2Cl_2$ was added and the organic layer was washed (saturated aqueous $NaHCO_3$, water, brine) and then dried ($Na_2SO_4$). The crude mixture was concentrated and used in the next step. A mixture of the crude product, tributyl(1-ethoxyvinyl)tin (17 μL, 0.050 mmol) and $(PPh_3)_2PdCl_2$ (2.5 mg, 0.0036 mmol) was refluxed in THF (2.5 mL) for 20 h in a Schlenk line. The reaction mixture was treated with 10% aqueous HCl (1 mL) at room temperature for 2 h. $CH_2Cl_2$ was added and the organic layer was separated. The organic layer was washed (saturated aqueous $NaHCO_3$, water, brine), dried ($Na_2SO_4$), and concentrated. The resulting residue was dissolved in $CHCl_3$ (2 mL). The solution was treated with $Zn(OAc)_2 \cdot 2H_2O$ (53 mg, 0.24 mmol) in (0.5 mL) MeOH and the reaction mixture was stirred for 4 h at room temperature. Concentration followed by chromatography of the crude mixture [silica, $CH_2Cl_2$] gave a green solid (4.2 mg, 23%): $^1$H NMR δ 1.38 (s, 21H), 1.83 (s, 6H), 1.98 (s, 6H), 2.60 (s, 3H), 2.82 (s, 3H), 4.47 (s, 2H), 7.22 (s, 2H), 8.30 (d, J=4.4 Hz, 1H), 8.43 (s, 1H), 8.72 (d, J=4.4 Hz, 1H), 8.79 (s, 1H), 8.84 (s, 1H), 9.64 (s, 1H), 9.70 (s, 1H); LD-MS obsd 742.6; FAB-MS obsd 742.3022, calcd 742.3045 ($C_{45}H_{50}N_4OSiZn$); $\lambda_{abs}$ 428, 652 nm.

References (1) Strain, H. H.; Svec, W. A. in *The Chlorophylls*, Vernon, L. P.; Seely, G. R., Eds., Academic Press: New York, 1966, pp 21-66.
(2) Eisner, U.; Linstead, R. P. *J. Chem. Soc.* 1955, 3742-3749.
(3) Scheer, H. In Chlorophylls; Scheer, H. Ed.; CRC Press, Inc.: Boca Raton, Fla., USA, 1991; pp 3-30.
(4) Boldt, N. J.; Donohoe, R. J.; Birge, R. R.; Bocian, D. F. *J. Am. Chem. Soc.* 1987, 109, 2284-2298.
(5) Smith, K. M.; Goff, D. A.; Simpson, D. J. *J. Am. Chem. Soc.* 1985, 107, 4946-4954.
(6) Tamiaki, H.; Miyatake, T.; Tanikaga, R. *Tetrahedron Lett.* 1997, 38, 267-270.
(7) Abraham, R. J.; Rowan, A. E.; Smith, N. W.; Smith, K. M. *J. Chem. Soc. Perkin Trans.* 2 1993, 1047-1059.
(8) Pavlov, V. Y.; Ponomarev, G. V. *Chemistry of Heterocyclic Compounds* 2004, 40, 393-425.
(9) Strachan, J.-P.; O'Shea, D. F.; Balasubramanian, T.; Lindsey, J. S. *J. Org. Chem.* 2000, 65, 3160-3172.
(10) Taniguchi, M.; Ra, D.; Mo, G.; Balasubramanian, T.; Lindsey, J. S. *J. Org. Chem.* 2001, 66, 7342-7354.
(11) Balasubramanian, T.; Strachan, J. P.; Boyle, P. D.; Lindsey, J. S. *J. Org. Chem.* 2000, 65, 7919-7929.
(12) Taniguchi, M.; Kim, H.-J.; Ra, D.; Schwartz, J. K.; Kirmaier, C.; Hindin, E.; Diers, J. R.; Prathapan, S.; Bocian, D. F.; Holten, D.; Lindsey, J. S. *J. Org. Chem.* 2002, 67, 7329-7342.
(13) Taniguchi, M.; Kim, M. N.; Ra, D.; Lindsey, J. S. *J. Org. Chem.* 2005, 70, 275-285.
(14) Ptaszek, M.; McDowell, B. E.; Taniguchi, M.; Kim, H.-J.; Boyle, P. D.; Lindsey, J. S. *J. Org. Chem.* to be submitted.
(15) (a) Bailey, D. M.; Johnson, R. E. *J. Med. Chem.* 1973, 16, 1300-1302. (b) Bailey, D. M.; Johnson, R. E.; Salvador, U. J. *J. Med. Chem.* 1973, 16, 1298-1300. (c) Gilow, H. M.; Burton, D. E. *J. Org. Chem.* 1981, 46, 2221-2225. (d) Keifer, P. A.; Schwartz, R. E.; Koker, M. E. S.; Hughes, R. G. Jr.; Rittschof, D.; Rinehart, K. L. *J. Org. Chem.* 1991, 56, 2965-2975. (e) Matsuki, S.; Mizuno, A.; Annoura, H.; Tatsuoka, T. *J. Heterocyclic Chem.* 1997, 34, 87-91. (f) Olofson, A.; Yakushijin, K.; Home, D. A. *J. Org. Chem.* 1998, 63, 1248-2225. (g) He, R. H.-Y.; Jiang, X.-K. *J. Chem. Research (S)* 1998, 786-787. (h) Armitt, D. J.; Banwell, M. G.; Freeman, C.; Parish, C. R. *J. Chem. Soc., Perkin Trans.* 1, 2002, 1743-1745. (i) Hoffmann, H.; Lindel, T. *Synthesis* 2003, 1753-1783. (j) Patel, J.; Pelloux-Leon, N.; Minassian, F.; Vallee, Y. *J. Org. Chem.* 2005, 70, 9081-9084.
(16) Ptaszek, M.; McDowell, M. E.; Lindsey, J. S. ((1-Formyldipyrromethanes can be prepared from a dipyrromethane by statistical Vilsmeier formylation followed by selective removal of the unwanted 1,9-diformyldipyrromethane by dialkyltin complexation. The 1-formyldipyrromethane can be brominated with NBS in the standard way to give the 1-formyl-9-bromodipyrromethane, which serves as an Eastern half in chlorin formation. The 1-formyl-9-bromodipyrromethane undergoes condensation with a Western half upon treatment with an acid catalyst such as p-toluenesulfonic acid. The metal-mediated oxidative cyclization then proceeds in the standard way to give the corresponding 5-unsubstituted chlorin.).
(17) Anderson, J. H.; Lee, S.-F. *Can. J. Chem.* 1965, 43, 409-414.
(18) Tietze, L. F.; Kettschau, G.; Heitmann, K. *Synthesis* 1996, 851-857.
(19) Hamdan, A.; Wasley, J. W. F. *Synth. Commun.* 1985, 15, 71-74.
(20) Bahulayan, D.; Das, S. K.; Iqbal, J. *J. Org. Chem.* 2003, 68, 5735-5738.
(21) Ptaszek, M.; Bhaumik, J.; Kim, H.-J.; Taniguchi, M.; Lindsey, J. S. *Org. Process Res. Dev.* 2005, 9, 651-659.
(22) Baftersby, A. R.; Fookes, C. J. R.; Snow, R. J. *J. Chem. Soc., Perkin Trans.* 1 1984, 2725-2732.
(23) Yasuhara, A.; Sakamoto, T. *Tetrahedron Lett.* 1998, 39, 595-596.
(24) Eisch, J. J.; Behrooz, M.; Dua, S. K. *J. Organomet. Chem.* 1985, 285, 121-136.
(25) (a) Alvarez, A.; Guzman, A.; Ruiz, A.; Velarde, E. *J. Org. Chem.* 1992, 57, 1653-1656. (b) Bergauer, M.; Hubner, H.; Gmeiner, P. *Bioorg. Med. Chem. Lett.* 2002, 12, 1937-1940.
(26) Haskins, C. M.; Knight, D. W. *Tetrahedron Lett.* 2004, 45, 599-601.
(27) DiMagno, S. G.; Lin, V. S.-Y.; Therein, M. J. *J. Org. Chem.* 1993, 58, 5983-5993.
(28) Kosugi, M.; Sumiya, T.; Obara, Y.; Suzuki, M.; Sano, H.; Migita, T. *Bull. Chem. Soc. Jpn.* 1987, 60, 767-768.
(29) Jones, I. D.; White, R. C.; Gibbs, E.; Denard, C. D. *J. Agric. Food Chem.* 1968, 16, 80-83.
(30) Balaban, T. S.; Linke-Schaetzel, M.; Bhise, A. D.; Vanthuyne, N.; Roussel, C. *Eur. J. Org. Chem.* 2004, 3919-3930.
(31) Gouterman, M. In *The Porphyrins*; Dolphin, D., Ed.; Academic Press: New York, 1978; Vol. III, pp 1-165.
(32) Tamiaki, H.; Kouroba, M. *Tetrahedron* 1997, 53, 10677-10688.
(33) Lin, V. S.-Y.; DiMagno, S. G.; Therien, M. J. *Science* 1994, 264, 1105-1111.
(34) Hindin, E.; Kirmaier, C.; Diers, J. R.; Tomizaki, K.-Y.; Taniguchi, M.; Lindsey, J. S.; Bocian, D. F.; Holten, D. *J. Phys. Chem. B* 2004, 108, 8190-8200.

The foregoing is illustrative of the present invention, and is not to be construed as limiting thereof. The invention is defined by the following claims, with equivalents of the claims to be included therein.

That which is claimed is:

1. In a method of detecting a target compound, cell or particle by flow cytometry, wherein said target is labeled with a detectable luminescent compound, the improvement comprising utilizing as said detectable luminescent compound a compound comprising a porphyrinic macrocycle;
wherein said detectable luminescent compound is excited by light at an excitation wavelength band and detected by emitted light at an emission wavelength band;
and wherein said emission wavelength band has a full width at half maximum peak of not more than 30 nanometers:
and wherein said porphyrinic macrocycle is:
a bacteriochlorin of Formula AI:

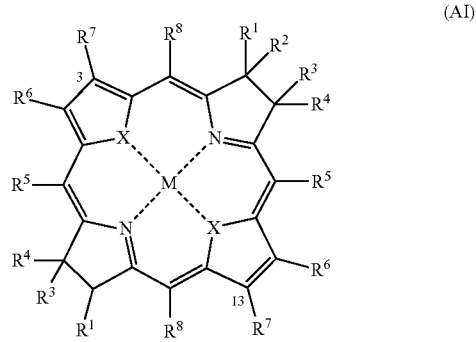

wherein:
M is a metal or is absent;
X is selected from the group consisting of Se, NH, $CH_2$, O and S;

$R^1$, $R^2$, $R^3$, $R^4$ $R^5$, $R^6$ $R^7$ and $R^8$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, protein, peptide, antibody, and polyalkylene oxide;

subject to the proviso that neither $R^1$ nor $R^2$ is H; or neither $R^3$ nor $R^4$ is H;

or $R^1$ and $R^2$ together are =O;

or $R^3$ and $R^4$ together form spiroalkyl, or $R^3$ and $R^4$ together are =O;

or a bacteriophorbine of Formula DIc or DIc':

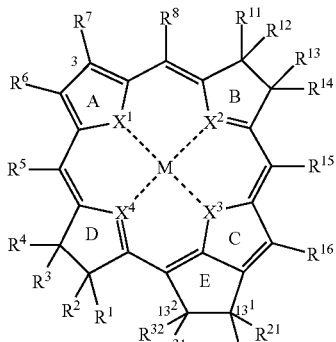

(DIc)

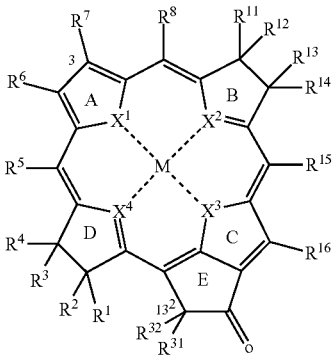

(DIc')

wherein:

M is a metal or is absent;

$X^1$, $X^2$, $X^3$ and $X^4$ are each independently selected from the group consisting of Se, NH, $CH_2$, O and S;

$R^1$, $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, $R^{21}$, $R^{22}$, $R^{31}$, and $R^{32}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, protein, peptide, antibody, and polyalkylene oxide;

wherein each pair of $R^1$ and $R^2$, $R^{11}$ and $R^{12}$, $R^{21}$ and $R^{22}$, or $R^{31}$ and $R^{32}$, can together form =O;

wherein each of $R^1$ and $R^2$, $R^3$ and $R^4$, $R^{11}$ and $R^{12}$, or $R^{13}$ and $R^{14}$, can together form spiroalkyl;

wherein $R^2$ and $R^3$ can together form a double bond; and wherein $R^{12}$ and $R^{13}$ can together form a double bond;

or a salt thereof.

2. The method of claim 1, wherein:

said excitation wavelength band has a peak between 350 and 900 nanometers; and said emission wavelength band has a peak between 550 and 1000 nanometers.

3. The method of claim 1, wherein:

said porphyrinic macrocycle is a bacteriochlorin;

said excitation wavelength band has a peak between 350 and 450 nanometers; and said emission wavelength band has a peak between 700 and 1000 nanometers.

4. The method of claim 1, wherein said detectable luminescent compound is excited by light at an excitation wavelength band and detected by emitted light at an emission wavelength band;

wherein said excitation wavelength band and said emission wavelength band each have peaks that are separated from one another by from 10 to 100 nanometers;

and wherein said emission wavelength band has a full width at half maximum peak of not more than 25 nanometers.

5. In a method of detecting and distinguishing first and second target compounds, cells or particles by flow cytometry, wherein said first target is labelled with a first detectable compound and said second target is labeled with a second detectable compound, the improvement comprising:

utilizing a compound comprising a first porphyrinic macrocycle as said first detectable compound and a compound comprising a second porphyrinic macrocycle as said second detectable compound;

wherein each of said first and second detectable compounds are excited at an excitation wavelength band;

and wherein:

(i) each of said first and second detectable compounds have a different emission wavelength band, said different emission wavelength bands characterized by peaks that are separated from one another by at least 5 nanometers; or (ii) said second compound has a lifetime at least 20 percent greater than said first compound;

and wherein said first and second porphyrinic macrocycles are each independently: a bacteriochlorin of Formula AI:

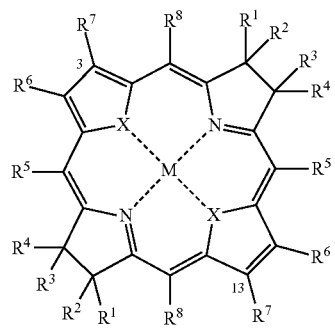

(AI)

wherein:

M is a metal or is absent;

X is selected from the group consisting of Se, NH, $CH_2$, O and S;

$R^1$, $R^2$, $R^3$, $R^4$ $R^5$, $R^6$ $R^7$ and $R^8$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, protein, peptide, antibody, and polyalkylene oxide;

subject to the proviso that neither $R^1$ nor $R^2$ is H; or neither $R^3$ nor $R^4$ is H;

or $R^1$ and $R^2$ together are =O;

or $R^3$ and $R^4$ together form spiroalkyl, or $R^3$ and $R^4$ together are =O;

or a bacteriophorbine of Formula DIc or DIc':

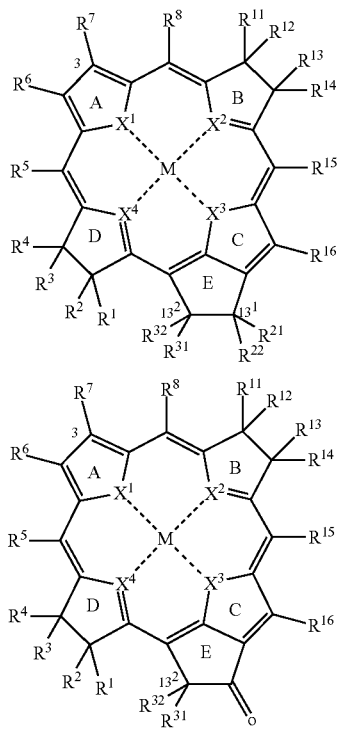

wherein:

M is a metal or is absent;

$X^1$, $X^2$, $X^3$ and $X^4$ are each independently selected from the group consisting of Se, NH, $CH_2$, O and S;

$R^1$, $R^2$, $R^3$, $R^4$, $R^5$, $R^6$, $R^7$, $R^8$, $R^{11}$, $R^{12}$, $R^{13}$, $R^{14}$, $R^{15}$, $R^{16}$, $R^{21}$, $R^{22}$, $R^{31}$ and $R^{32}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, acyl, formyl, carboxylic acid, acylamino, ester, amide, hydroxyl, nitro, alkylthio, amino, alkylamino, arylalkylamino, disubstituted amino, acyloxy, sulfoxyl, sulfonyl, sulfonate, sulfonic acid, sulfonamide, urea, alkoxylacylamino, aminoacyloxy, protein, peptide, antibody, and polyalkylene oxide;

wherein each pair of $R^1$ and $R^2$, $R^{11}$ and $R^{12}$, $R^{21}$ and $R^{22}$, or $R^{31}$ and $R^{32}$, can together form =O;

wherein each of $R^1$ and $R^2$, $R^3$ and $R^4$, $R^{11}$ and $R^{12}$, or $R^{13}$ and $R^{14}$, can together form spiroalkyl;

wherein $R^2$ and $R^3$ can together form a double bond; and wherein $R^{12}$ and $R^{13}$ can together form a double bond;

or a salt thereof.

6. The method of claim 5, wherein both of said excitation wavelength bands have a peak between 350 and 900 nanometers; and both of said emission wavelength bands have a peak between 550 and 1000 nanometers.

7. The method of claim 5, wherein said different emission wavelength bands are characterized by peaks that are separated from one another by at least 50 nanometers.

8. The method of claim 5, wherein said different emission wavelength bands are characterized by peaks that are separated from one another by 10 to 50 nanometers;

and wherein each of said different emission wavelength bands have a full width at half maximum peak of not more than 30 nanometers.

\* \* \* \* \*

UNITED STATES PATENT AND TRADEMARK OFFICE
CERTIFICATE OF CORRECTION

PATENT NO. : 8,187,824 B2
APPLICATION NO. : 12/095423
DATED : May 29, 2012
INVENTOR(S) : Lindsey It is certified that error appears in the above-identified patent and that said Letters Patent is hereby corrected as shown below:

In the Specifications:
Column 3, Line 56: Please correct "($Q_y$ at 641 nm." to read -- ($Q_y$ at 641 nm). --

Column 14, Item (AII), Line 8: Please correct

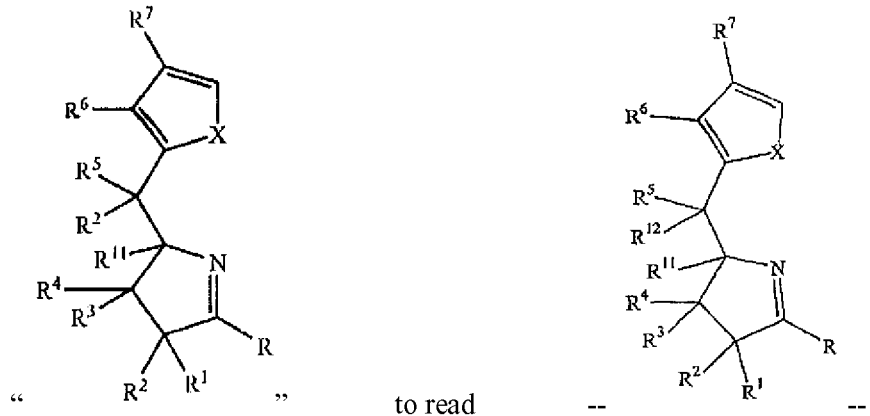

" " to read -- --

Column 14, Line 22: Please correct "and $R^9$ is H;" to read -- and $R^8$ is H; --

Column 18, Line 25: Please correct "$R^1$ is an iconic" to read -- $R^2$ is an iconic --

Column 21, Line 53: Please correct "is $Alk^{40}R^{41}$ wherein $Alk^{41}$"
to read -- is $Alk^{41}R^{41}$ wherein $Alk^{41}$ --

Signed and Sealed this
Twenty-third Day of April, 2013

Teresa Stanek Rea
*Acting Director of the United States Patent and Trademark Office*

CERTIFICATE OF CORRECTION (continued)
U.S. Pat. No. 8,187,824 B2

Column 32, Formula (DIb): Please correct

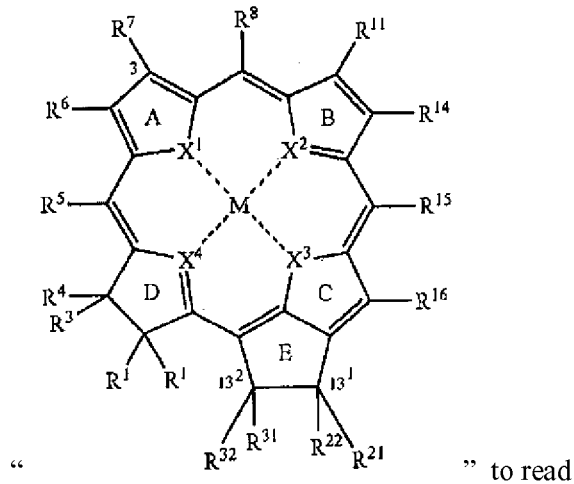

" to read

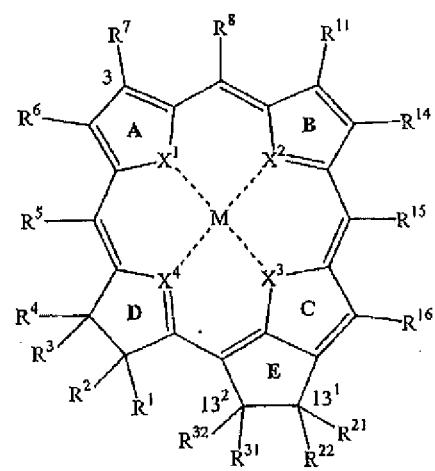

-- --

Formula (DIc): Please correct

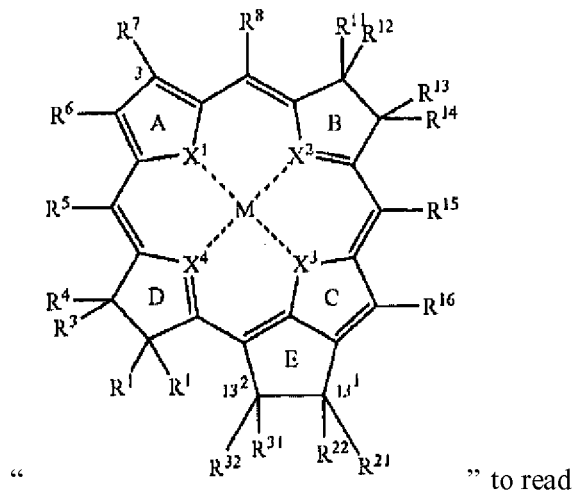

" to read

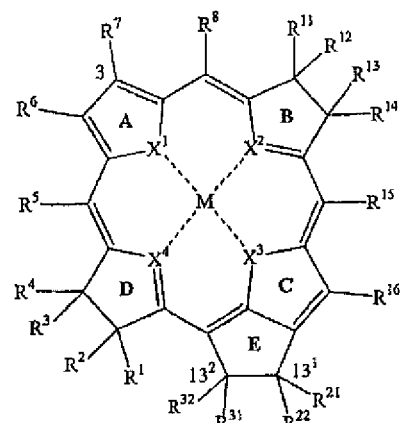

-- --

Column 53, Scheme 4: Please correct

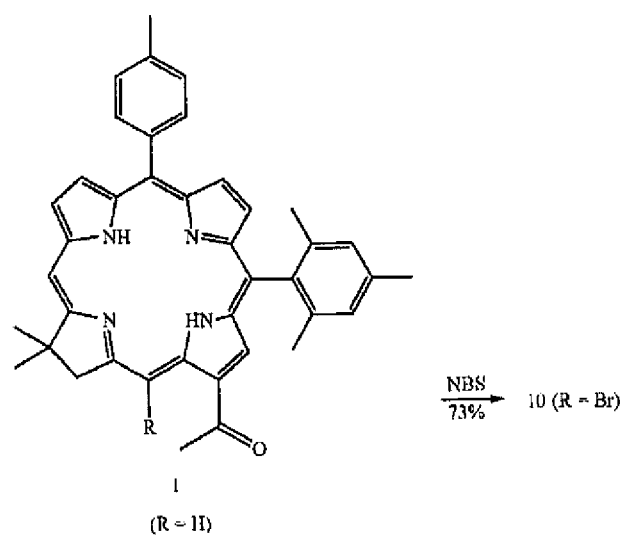

" to read

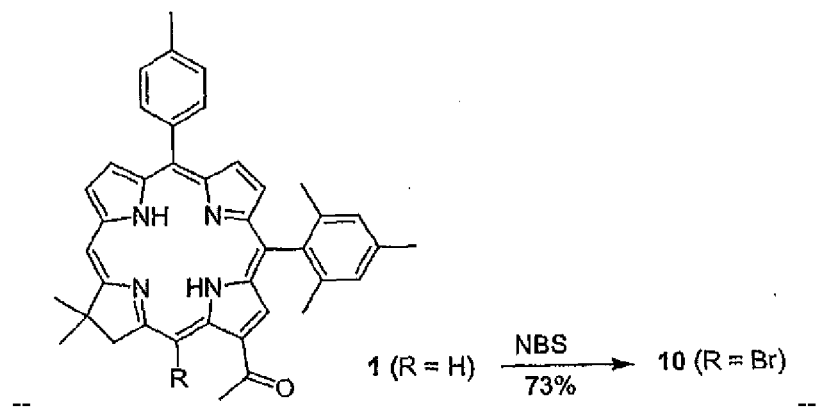
Column 75, Scheme 7, Lines 17-21: Please correct
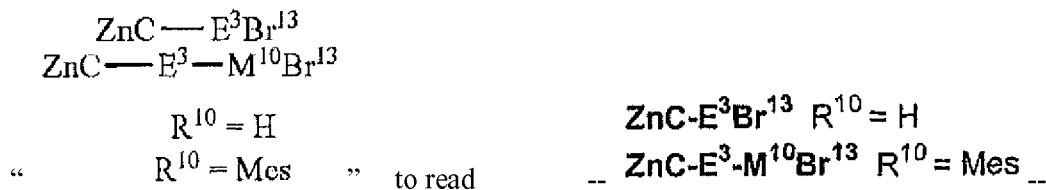
to read
Lines 46-51: Please correct
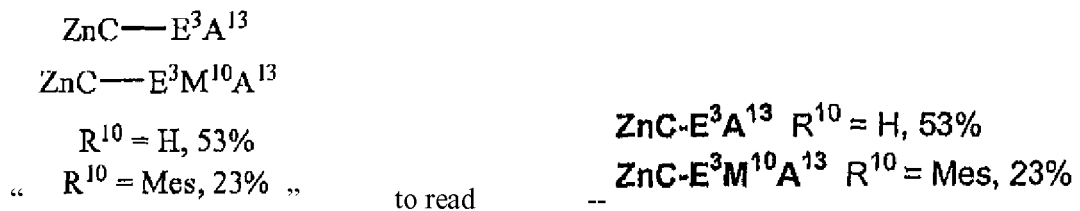
to read
Column 76, Lines 44-45:
    Please correct "from 621 to 655 Zone Name: A1, AMD Zone Name: A2,AMD" to read -- from 621 to 655nm. --
Column 88, Line 3: Please correct "Baftersby, A. R.;" to read -- Battersby, A. R.; --
In the Claims:
Column 88, Claim 1, Formula (AI): Please correct
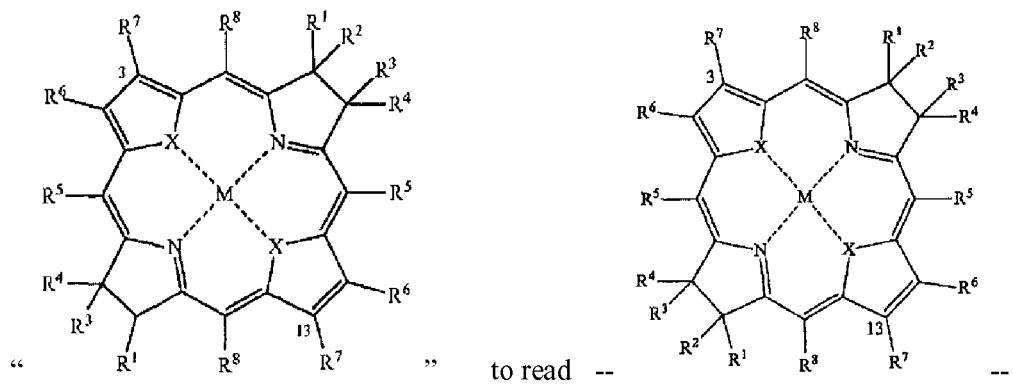
to read --

CERTIFICATE OF CORRECTION (continued) Page 4 of 4
U.S. Pat. No. 8,187,824 B2

Column 89, Claim 1, Formula (DIc'): Please correct

" 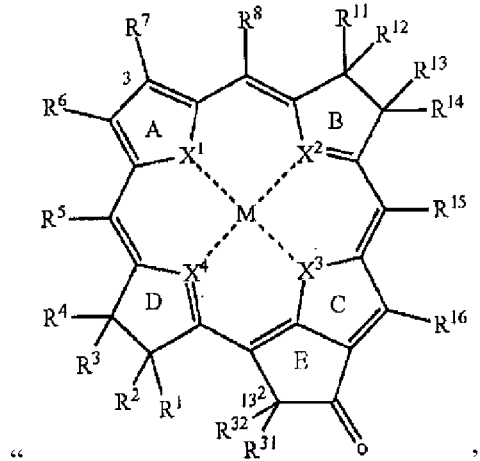 " to read -- 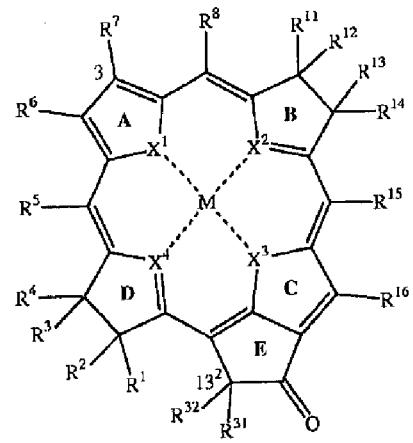 --

Column 91, Claim 5, Formula (DIc'): Please correct

" 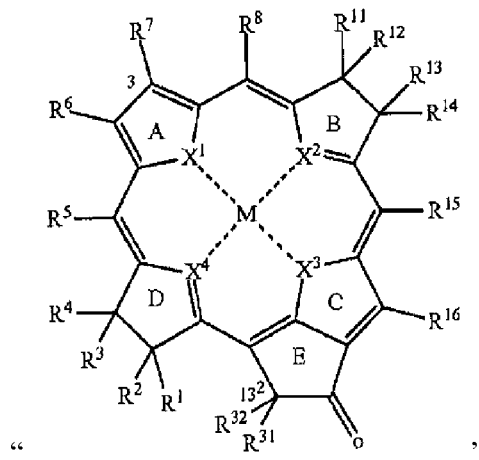 " to read -- 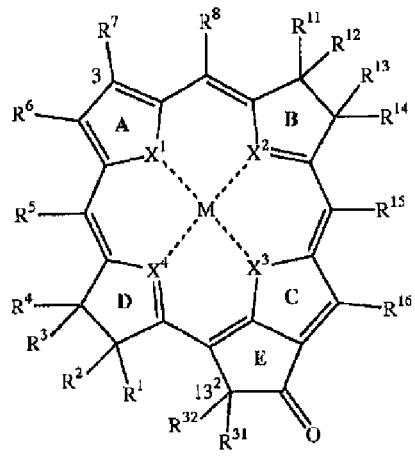 --